US007825155B2

(12) United States Patent
Tokunaga et al.

(10) Patent No.: US 7,825,155 B2
(45) Date of Patent: Nov. 2, 2010

(54) OXINDOLE DERIVATIVE AS FEEDING CONTROL AGENT

(75) Inventors: Teruhisa Tokunaga, Osaka (JP); Tsuyoshi Takasaki, Osaka (JP); Kozo Yoshida, Osaka (JP); Ryu Nagata, Suita (JP)

(73) Assignee: Dainippon Sumitomo Pharma Co., Ltd., Osaka-Shi, Osaka (JP)

( * ) Notice: Subject to any disclaimer, the term of this patent is extended or adjusted under 35 U.S.C. 154(b) by 83 days.

(21) Appl. No.: 12/066,251

(22) PCT Filed: Sep. 13, 2006

(86) PCT No.: PCT/JP2006/318128

§ 371 (c)(1), (2), (4) Date: Mar. 7, 2008

(87) PCT Pub. No.: WO2007/032371

PCT Pub. Date: Mar. 22, 2007

(65) Prior Publication Data

US 2009/0131398 A1 May 21, 2009

(30) Foreign Application Priority Data

Sep. 14, 2005 (JP) ............................ 2005-266310

(51) Int. Cl.

| | |
|---|---|
| ***C07D 403/06*** | (2006.01) |
| ***C07D 403/02*** | (2006.01) |
| ***C07D 405/04*** | (2006.01) |
| ***C07D 413/04*** | (2006.01) |
| ***C07D 403/04*** | (2006.01) |
| ***C07D 417/06*** | (2006.01) |
| ***C07D 417/02*** | (2006.01) |
| ***C07D 417/04*** | (2006.01) |
| ***C07D 401/12*** | (2006.01) |
| ***C07D 401/02*** | (2006.01) |
| ***C07D 401/06*** | (2006.01) |
| ***C07D 409/04*** | (2006.01) |
| ***C07D 413/02*** | (2006.01) |
| ***C07D 413/06*** | (2006.01) |
| ***C07D 209/34*** | (2006.01) |
| ***C07D 209/38*** | (2006.01) |
| ***A61K 31/541*** | (2006.01) |
| ***A61K 31/5377*** | (2006.01) |
| ***A61K 31/497*** | (2006.01) |
| ***A61K 31/496*** | (2006.01) |
| ***A61K 31/4439*** | (2006.01) |
| ***A61K 31/454*** | (2006.01) |
| ***A61K 31/427*** | (2006.01) |
| ***A61K 31/422*** | (2006.01) |
| ***A61K 31/4245*** | (2006.01) |
| ***A61K 31/4178*** | (2006.01) |
| ***A61K 31/4155*** | (2006.01) |
| ***A61K 31/404*** | (2006.01) |

(52) U.S. Cl. ....................... 514/418; 514/374; 514/376; 514/392; 514/365; 514/228.2; 514/339; 514/254.09; 514/235.2; 514/323; 514/397; 514/383; 514/406; 514/407; 514/369; 514/367; 514/375; 514/364; 514/256; 514/378; 514/255.05; 548/468; 548/466; 548/235; 548/485; 548/486; 548/229; 548/312.1; 548/200; 548/205; 548/266.4; 548/364.7; 548/217; 548/224; 548/159; 548/131; 548/249; 544/62; 544/373; 544/144; 544/333; 544/405; 546/277.7; 546/201

(58) Field of Classification Search ....................... None
See application file for complete search history.

(56) References Cited

U.S. PATENT DOCUMENTS 6,576,656 B1 6/2003 Tokunaga et al.
6,939,887 B2 9/2005 Okazaki et al.

FOREIGN PATENT DOCUMENTS

WO WO-2005/035498 4/2005

OTHER PUBLICATIONS

Jordan, V. C. Nature Reviews: Drug Discovery, 2, 2003, pp. 205-213.*

(Continued)

*Primary Examiner*—Rebecca L Anderson
*Assistant Examiner*—Matthew P Coughlin
(74) *Attorney, Agent, or Firm*—Birch, Stewart, Kolasch & Birch, LLP

(57) ABSTRACT

Disclosed is a compound represented by the formula (1) below, a prodrug thereof or a pharmaceutically acceptable salt of either, which is useful as a therapeutic, preventive or ameliorating agent for diabetes and the like.

(1)

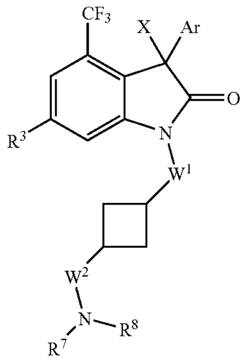

(In the formula, $R^3$ represents an optionally substituted carbamoyl group or the like; X represents a hydroxyl group or the like; $W^1$ and $W^2$ independently represent a single bond or methylene; $R^7$ and $R^8$ independently represent a hydrogen atom, an optionally substituted alkyl group or the like; and Ar represents an optionally substituted aryl group or the like.)

16 Claims, No Drawings

OTHER PUBLICATIONS

Dezaki et al. Pharmacology & Therapeutics 2008, 118, pp. 239-249.*
Rautio et al. Nature Reviews Drug Discovery 2008, 7, pp. 255-270.*
Wang et al. Drug Delivery: Principles and Applications, 2005 John Wiley & Sons, Inc. Publication, Section 8.3, pp. 136-137.*
Smith, D. A. Current Opinion in Drug Discovery & Development 2007, 10, 550-559.*
Testa, B. Current Opinion in Chemical Biology 2009, 13, pp. 338-344.*

* cited by examiner

OXINDOLE DERIVATIVE AS FEEDING CONTROL AGENT

This Application is the National Phase Under 35 U.S.C. §371 of PCT International Application No. PCT/JP2006/318128 which has an International filing date of Sep. 13, 2006, which claims priority to Japanese Application No. 2005-266310 filed on Sep. 14, 2005, the entire contents of all applications listed above are hereby incorporated by reference.

TECHNICAL FIELD

The present invention relates to oxindole derivatives with feeding control activities.

BACKGROUND ART

With the recent changes of diet and life style, adult diseases such as diabetes, hypertension and hyperlipidemia are increasing, which is becoming a social problem. Obesity is an important risk factor for adult diseases, and it is known that obesity is closely linked with feeding activity. Recently, psychogenic feeding disorders are also increased. These feeding disorders are classified by anorexia syndrome and bulimia nervosa, and subtypes associated with overeating exist in the anorexia syndrome. Accordingly, feeding control mechanism is attracting attention.

It has been found recently that a gastrointestinal hormone Ghrelin secreted by the stomach is a feeding control factor. Ghrelin has an energy metabolism regulation activity such as feeding increasing activity, fat accumulating activity and weight increasing activity, and it has been reported that feeding increased when it was administered to rodent or human. Additionally, a reduction of the feeding amount and an inhibition of weight gain have been observed when a peptidic Ghrelin antagonist was administered to animal model, and hence, it has been shown that an agent inhibiting action of Ghrelin has a possibility of using for treating such diseases as obesity and diabetes as a feeding control agent.

A feeding inhibitory agent affecting central nerve system such as mazindol or sibutramine is known as an agent which is effective for inhibition of feeding and is useful for the treatment or prevention of obesity. However, it cannot be satisfied in terms of concerns about habitation and side effects such as thirst or effects on blood pressure.

Patent Document 1 discloses use of an oxindole derivative as a feeding control agent.

Patent Document: WO2005/035498

DISCLOSURE OF INVENTION

Problems to be Resolved by the Invention

An effective feeding control agent as a medicament has been desired as described above. Specifically, the subject of the present invention is to provide an effective feeding control agent for treating, preventing or improving diabetes mellitus, etc.

Means of Solving the Problems

According to the intensive study by the present inventors, it has been found for feeding control agents that a compound of the formula (1) or its prodrug, or a pharmaceutically acceptable salt thereof is an oral feeding control agent applicable as a medicament on the basis of Ghrelin antagonism, and have accomplished the present invention.

The present invention relates to the following embodiments.

[1] A compound of the formula (1):

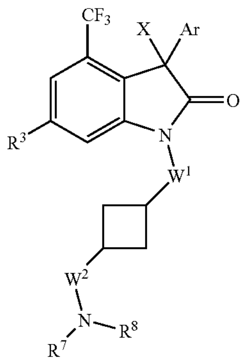

(1)

wherein $R^3$ is hydrogen atom, optionally substituted alkyl, optionally substituted alkenyl, optionally substituted alkynyl, optionally substituted aryl, optionally substituted heteroaryl, optionally substituted saturated heterocycle, halogen atom, cyano, nitro, carboxy, hydroxyl, optionally substituted amino, optionally substituted alkoxy, optionally substituted alkanoyl, optionally substituted alkoxycarbonyl, optionally substituted sulfamoyl, optionally substituted carbamoyl, optionally substituted ureido, optionally substituted alkylthio, optionally substituted alkylsulfinyl, optionally substituted alkylsulfonyl, optionally substituted alkylsulfonylamino, optionally substituted arylsulfonylamino, or optionally substituted alkanoylamino;

X is hydrogen atom, hydroxyl, halogen atom, $C_1$-$C_4$ alkoxy, $C_1$-$C_4$ alkanoyloxy optionally substituted by fluorine atom;

$W^1$ and $W^2$ are each independently a single bond or methylene;

$R^7$ and $R^8$ are each independently hydrogen atom, optionally substituted alkyl or optionally substituted cycloalkyl, or $R^7$ and $R^8$ are combined together with the adjacent nitrogen atom to form optionally substituted saturated heterocycle;

Ar is optionally substituted aryl or optionally substituted heteroaryl; or its prodrug, or a pharmaceutically acceptable salt thereof.

[2] The compound of [1], wherein Ar is phenyl substituted by 1 or more substituent(s) in which the substituent is selected from alkyl optionally substituted by fluorine atom, halogen atom or cyano; or its prodrug, or a pharmaceutically acceptable salt thereof.

[3] The compound of [2], wherein Ar is substituted phenyl in which at least one substituent is present at 2-position; or its prodrug, or a pharmaceutically acceptable salt thereof.

[4] The compound of [2], wherein Ar is substituted phenyl in which at least two substituents are present at 2- and 4-positions or 2- and 6-positions; or its prodrug, or a pharmaceutically acceptable salt thereof.

[5] The compound of [2], wherein Ar is substituted phenyl in which at least three substituents are present at 2-, 4- and 6-positions; or its prodrug, or a pharmaceutically acceptable salt thereof.

[6] The compound of [1], wherein $R^3$ is hydrogen atom, alkyl optionally substituted by halogen atom, optionally substituted carbamoyl, carboxy, halogen atom, alkoxy optionally substituted by halogen atom, optionally substituted heteroaryl, hydroxyl, optionally substituted amino, optionally substituted saturated heterocycle, alkylsulfonyl, sulfamoyl optionally substituted by alkyl, alkanoylamino, alkylsulfonylamino, or $-C{\equiv}C-(CH_2)_p-Q$ in which p is 1 or 2 and Q is hydroxyl, optionally substituted amino, optionally substituted carbamoyl, optionally substituted saturated heterocycle, alkylsulfonyl, alkanoylamino, alkylsulfonylamino or alkylureido; or its prodrug, or a pharmaceutically acceptable salt thereof.

[7] The compound of [1], wherein $R^3$ is optionally substituted 5-membered heteroaryl, optionally substituted 5-membered saturated heterocycle, optionally substituted carbamoyl or carboxy; or its prodrug, or a pharmaceutically acceptable salt thereof.

[8] The compound of [1], wherein $R^3$ is oxazolyl, substituted oxazolyl, thiazolyl, substituted thiazolyl, triazolyl, imidazolyl, carbamoyl, methylcarbamoyl, dimethylcarbamoyl or carboxy; or its prodrug, or a pharmaceutically acceptable salt thereof.

[9] The compound of any one of [1] to [8], wherein $W^1$ and $W^2$ are in trans position in a partial structural formula (Y) of the formula (1):

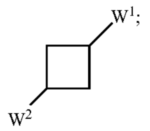

(Y)

or its prodrug, or a pharmaceutically acceptable salt thereof.

[10] The compound of [9], wherein $W^1$ is methylene and $W^2$ is a single bond; or its prodrug, or a pharmaceutically acceptable salt thereof.

[11] The compound of any one of [1] to [10], wherein $R^7$ and $R^8$ are each independently $C_1$-$C_4$ alkyl; or its prodrug, or a pharmaceutically acceptable salt thereof.

[12] The compound of any one of [1] to [10], wherein $R^7$ and $R^8$ are each independently cyclopropyl-substituted $C_1$-$C_4$ alkyl; or its prodrug, or a pharmaceutically acceptable salt thereof.

[13] The compound of any one of [1] to [10], wherein $R^7$ and $R^8$ are each independently $C_3$-$C_6$ cycloalkyl; or its prodrug, or a pharmaceutically acceptable salt thereof.

[14] An optically active isomer of the compound of any one of [1] to [13] in the configuration of the formula (2):

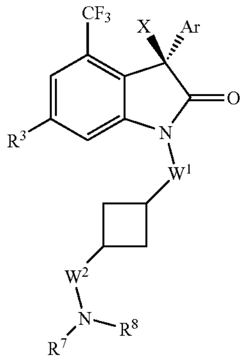

(2)

wherein $R^3$, $R^7$, $R^8$, X, Ar, $W^1$ and $W^2$ are the same as defined in claim 1; or its prodrug, or a pharmaceutically acceptable salt thereof.

[15] A pharmaceutical composition comprising as an active ingredient the compound of any one of [1] to [14] or its prodrug, or a pharmaceutically acceptable salt thereof.

[16] A therapeutic or preventive agent for diabetes comprising as an active ingredient, the compound of any one of [1] to [14] or its prodrug, or a pharmaceutically acceptable salt thereof.

[17] A feeding control agent comprising as an active ingredient the compound of any one of [1] to [14] or its prodrug, or a pharmaceutically acceptable salt thereof.

[18] A therapeutic or preventive agent for obesity comprising as an active ingredient, the compound of any one of [1] to [14] or its prodrug, or a pharmaceutically acceptable salt thereof.

[19] A therapeutic or preventive agent for hyperlipidemia comprising as an active ingredient, the compound of any one of [1] to [14] or its prodrug, or a pharmaceutically acceptable salt thereof.

[20] Use of the compound of any one of [1] to [14] or its prodrug, or a pharmaceutically acceptable salt thereof in the manufacture of a therapeutic agent for diabetes, obesity or hyperlipidemia, or a feeding control agent.

[21] A method for treating diabetes, obesity or hyperlipidemia or feed-controlling, comprising administering an effective amount of the compound of any one of [1] to [14] or its prodrug, or a pharmaceutically acceptable salt thereof to a patient in need of such treatment.

The compound of the formula (1) or its prodrug, or a pharmaceutically acceptable salt thereof is hereinafter referred to as "the present compound", if necessary.

Effect of the Invention

The present invention can provide an oxindole derivative or its prodrug, or a pharmaceutically acceptable salt thereof useful as a feeding control agent.

BEST MODE FOR CARRYING OUT THE INVENTION

The present invention is explained more particularly as follows.

The number of substituents on the groups defined by "optionally substituted" or "substituted" groups herein includes 1 or more, but is not limited thereto, if substitutable, Unless otherwise specified, explanation for each group also applies to the case that the group is a part of another group or a substituent thereof.

The "alkyl" includes, for example, straight chain or branched chain $C_1$-$C_6$ alkyl, particularly methyl, ethyl, propyl, 1-methylethyl, butyl, 1-methylpropyl, 2-methylpropyl, 1,1-dimethylethyl, pentyl, 1-methylbutyl, 2-methylbutyl, 1-ethylpropyl, hexyl, 1-methylpentyl, 2-methylpentyl or 1-ethylbutyl, etc. The alkyl in "alkylthio", "alkylsulfinyl", "alkylsulfonyl", "alkylsulfonylamino" and "alkylureido" includes the similar ones to the above. The preferable alkyl is, for example, straight chain or branched chain $C_1$-$C_4$ alkyl, etc.

The "alkenyl" includes, for example, straight chain or branched chain $C_2$-$C_6$ alkenyl, particularly vinyl, 1-propenyl, 2-propenyl, 1-butenyl, 2-butenyl, 3-butenyl or 1-pentenyl, etc.

The "alkynyl" includes, for example, straight chain or branched chain $C_2$-$C_6$ alkynyl, particularly ethynyl, 1-propynyl, 2-propynyl, 1-butynyl or 1-pentynyl, etc.

The "alkoxy" includes, for example, straight chain or branched chain $C_1$-$C_6$ alkoxy, particularly methoxy, ethoxy, propoxy, 1-methylethoxy, butoxy, 1-methylpropoxy, 2-methylpropoxy, pentoxy, 1-methylbutoxy, 2-methylbutoxy, 1-ethylpropoxy, hexoxy, 1-methylpentoxy, 2-methylpentoxy or 1-ethylbutoxy, etc. The alkoxy in "alkoxycarbonyl" includes the similar ones to the above. The preferable alkoxy is, for example, straight chain or branched chain $C_1$-$C_4$ alkoxy, etc.

The "alkanoyl" includes, for example, straight chain or branched chain $C_1$-$C_6$ alkanoyl, particularly formyl, acetyl, propionyl or butyryl, etc. The alkanoyl in "alkanoylamino" and "alkanoyloxy" includes the similar ones to the above. The preferable alkanoyl is, for example, straight chain or branched chain $C_1$-$C_4$ alkanoyl, etc.

The substituent in "substituted alkyl" includes, for example, halogen atom, optionally substituted amino, alkoxy, alkoxycarbonyl, optionally substituted cycloalkyl, aryl, hydroxyl, carboxy, optionally substituted carbamoyl, alkanoyl, arylcarbonyl, heteroarylcarbonyl, saturated heterocyclic carbonyl, alkanoylamino, alkylsulfonylamino, optionally substituted ureido, alkoxycarbonylamino, saturated heterocycle or optionally substituted sulfamoyl, etc.

The preferable substituted alkyl in $R^3$ is, for example, halogen-atom-substituted alkyl such as trifluoromethyl, pentafluoroethyl or 2-chloroethyl.

The substituent in "substituted alkenyl" and "substituted alkynyl" includes, for example, halogen atom, optionally substituted alkyl, optionally substituted amino, alkoxy, alkoxycarbonyl, aryl, hydroxyl, carboxy, optionally substituted carbamoyl, alkanoyl, arylcarbonyl, heteroarylcarbonyl, saturated heterocyclic carbonyl, alkylsulfonyl, alkanoylamino, alkylsulfonylamino, optionally substituted ureido, alkoxycarbonylamino, optionally substituted saturated heterocycle or optionally substituted sulfamoyl, etc.

The substituent in optionally substituted alkyl as the substituent in "substituted alkenyl" and "substituted alkynyl" includes, for example, hydroxyl, optionally substituted amino, optionally substituted carbamoyl, optionally substituted saturated heterocycle, alkylsulfonyl, alkanoylamino, alkylsulfonylamino or alkylureido, etc.

The substituent in "optionally substituted alkoxy", "optionally substituted alkanoyl", "optionally substituted alkoxycarbonyl", "optionally substituted alkylthio", "optionally substituted alkylsulfinyl", "optionally substituted alkylsulfonyl", "optionally substituted alkylsulfonylamino" and "optionally substituted alkanoylamino" includes, for example, halogen atom, alkoxy, optionally substituted cycloalkyl, aryl, heteroaryl or hydroxyl, etc.

The "aryl" includes, for example, $C_6$-$C_{10}$ aryl, particularly phenyl, 1-naphthyl or 2-naphthyl, etc. The aryl in "arylcarbonyl" includes the similar ones to the above.

The "heteroaryl" includes, for example, mono or bi-cyclic 5- to 10-membered heteroaryl containing 1 to 3 nitrogen, oxygen and/or sulfur atom(s), particularly monocyclic 5- to 7-membered heteroaryl containing 1 to 3 nitrogen, oxygen and/or sulfur atom(s) such as pyridyl, pyridazinyl, isothiazolyl, pyrrolyl, furyl, thienyl, thiazolyl, imidazolyl, pyrimidinyl, thiadiazolyl, pyrazolyl, oxazolyl, isoxazolyl, pyrazinyl, triazinyl, triazolyl, imidazolidinyl, oxadiazolyl, triazolyl or tetrazolyl, or bicyclic 9- to 10-membered heteroaryl containing 1 to 3 nitrogen, oxygen and/or sulfur atom(s) such as indolyl, indazolyl, chromenyl, quinolyl, isoquinolyl, benzofuranyl, benzothienyl, benzoxazolyl, benzothiazolyl, benzisoxazolyl, benzisothiazolyl, benzotriazolyl or benzimidazolyl, etc. The heteroaryl in "heteroarylcarbonyl" includes the similar ones to the above.

The "cycloalkyl" includes, for example, $C_3$-$C_8$ cycloalkyl, particularly cyclopropyl, cyclobutyl, cyclopentyl, cyclohexyl, cycloheptyl or cyclooctyl, etc.

The "saturated heterocycle" includes, for example, monocyclic 5- to 8-membered saturated heterocycle containing 1 to 3 nitrogen, oxygen and/or sulfur atom(s), particularly monocyclic 5-membered saturated heterocycle containing 1 to 3 nitrogen, oxygen and/or sulfur atom(s) such as tetrahydrofuranyl, pyrrolidinyl, dihydropyrrolyl, pyrazolinyl, pyrazolidinyl, imidazolidinyl, thiazolidinyl or oxazolidinyl, monocyclic 6-membered saturated heterocycle containing 1 to 3 nitrogen, oxygen and/or sulfur atom(s) such as piperidinyl, morpholinyl, thiomorpholinyl or piperazinyl, monocyclic 7-membered saturated heterocycle containing 1 to 3 nitrogen, oxygen and/or sulfur atom(s) such as perhydroazepine, etc. The saturated heterocycle also includes, for example, 7 to 9-membered bicyclic saturated heterocycle containing 1 nitrogen such as 7-azabicyclo[2.2.1]heptane, 3-azabicyclo[3.2.1]octane or 3-azabicyclo[3.2.2]nonane, etc.

The substituent in "optionally substituted aryl", "optionally substituted phenyl", "optionally substituted naphthyl", "Optionally substituted heteroaryl" and "optionally substituted saturated heterocycle" includes, for example, halogen atom, aryl, heteroaryl, optionally substituted alkyl, optionally substituted alkenyl, optionally substituted alkynyl, optionally substituted amino, cyano, nitro, hydroxyl, mercapto, optionally substituted alkoxy, alkanoyl, alkoxycarbonyl, carboxy, optionally substituted sulfamoyl, optionally substituted carbamoyl, alkylsulfamoylamino, alkylthio, alkylsulfinyl, alkylsulfonyl, alkylsulfonylamino or alkanoylamino, etc.

The substituent in "optionally substituted saturated heterocycle" also includes oxo. The "oxo-saturated heterocycle" includes, for example, oxo-5-membered saturated heterocycle such as pyrrolidinonyl, thiazolidinonyl, 2-oxo-1,3-oxazolinyl or 2-oxo-imidazolidinyl, oxo-6-membered saturated heterocycle such as piperidinonyl, or 5- to 6-membered saturated heterocyclic dioxide such as thiazolidinyl dioxide or thiomorpholinyl dioxide, etc.

The substituent in "optionally substituted cycloalkyl" includes, for example, halogen atom, aryl, heteroaryl, optionally substituted alkyl, alkenyl, alkynyl, optionally substituted amino, cyano, nitro, hydroxyl, mercapto, alkoxy, alkanoyl, alkoxycarbonyl, carboxy, optionally substituted sulfamoyl, optionally substituted carbamoyl, alkylsulfamoylamino, alkylthio, alkylsulfinyl, alkylsulfonyl, alkylsulfonylamino or alkanoylamino, etc.

The substituent in optionally substituted alkyl as the substituent in "optionally substituted cycloalkyl" includes, for example, halogen atom, alkyl optionally substituted amino, alkoxy, alkoxycarbonyl, aryl, hydroxyl, carboxy, alkyl optionally substituted carbamoyl, alkanoyl, arylcarbonyl, heteroarylcarbonyl, saturated heterocyclic carbonyl, alkanoylamino, alkylsulfonylamino, alkyl optionally substituted ureido, alkoxycarbonylamino, saturated heterocycle or optionally substituted sulfamoyl, etc.

The preferable substituent in "substituted aryl" and "substituted heteroaryl" in Ar includes, for example, halogen atom, alkyl, cyano, alkenyl, alkynyl, alkoxy or halogen-atom-substituted alkyl, particularly chlorine atom, fluorine atom, methyl, ethyl, methoxy or trifluoromethyl, etc.

The "halogen atom" includes, for example, fluorine atom, chlorine atom, bromine atom or iodine atom, etc.

The substituent in "optionally substituted amino" includes, for example, optionally substituted alkyl wherein the substituent includes, for example, hydroxyl, alkoxy or cycloalkyl, etc., and the amino may be optionally substituted by the same or different 2 substituents. In case that the amino is substituted by 2 substituents, the 2 substituents may be combined together with the adjacent nitrogen atom to form saturated heterocycle such as pyrrolidine, piperazine or morpholine.

The substituent in "optionally substituted sulfamoyl", "optionally substituted carbamoyl" and "optionally substituted ureido" includes, for example, optionally substituted alkyl wherein the substituent includes, for example, hydroxyl or alkoxy, etc., and the sulfamoyl, carbamoyl and ureido may be optionally substituted by the same or different 2 substituents. In case that sulfamoyl, carbamoyl or ureido is substituted by 2 substituents, the 2 substituents may be combined together with the adjacent nitrogen atom to form saturated heterocycle such as pyrrolidine, piperazine or morpholine.

Specifically, the optionally substituted sulfamoyl includes optionally substituted saturated heterocyclic sulfonyl, the optionally substituted carbamoyl includes optionally substituted saturated heterocyclic carbonyl, and the optionally substituted ureido includes optionally substituted saturated heterocyclic carbonylamino, respectively.

The halogen atom in X is preferably, for example, fluorine atom or chlorine atom, etc.

The $C_1$-$C_4$ alkoxy in X is preferably, for example, methoxy or ethoxy, etc.

The $C_1$-$C_4$ alkanoyloxy optionally substituted by fluorine atom in X is preferably, for example, trifluoroacetoxy, acetoxy or propanoyloxy, etc.

The halogen atom as the substituent of the substituted phenyl in Ar is preferably, for example, fluorine atom, chlorine atom or bromine atom, etc.

The alkyl optionally substituted by fluorine atom as the substituent of the substituted phenyl in Ar is preferably, for example, trifluoromethyl or methyl, etc.

The $C_1$-$C_4$ alkyl in $R^7$ and $R^8$ is preferably, for example, methyl, ethyl or isopropyl, etc.

The cycloalkyl-substituted $C_1$-$C_4$ alkyl in $R^7$ and $R^8$ is preferably, for example, cyclopropylmethyl, etc.

The $C_3$-$C_6$ cycloalkyl in $R^7$ and $R^8$ is preferably, for example, cyclobutyl, etc.

The substituent of the substituted oxazolyl and substituted thiazolyl in $R^3$ is preferably, for example, alkyl such as methyl, ethyl, propyl, isopropyl or t-butyl, or optionally substituted carbamoyl including dialkylaminocarbonyl such as carbamoyl, dimethylaminocarbonyl or diethylaminocarbonyl, saturated heterocyclic carbonyl such as pyrrolidinocarbonyl, piperidinocarbonyl or morpholinocarbonyl, etc.

The "prodrug" includes, for example, a prodrug described in Chemistry and Industry, 1980, 435 or Advanced Drug Discovery Reviews 3, 39 (1989). Particularly, the prodrug may be a biodegradable or hydrolyzable carboxy ester such as acyloxy methyl ester, glycolate, lactate and morpholino ethyl ester, phenolic hydroxyl glutaric acid monoester, N-morpholinomethylamide, N-acyloxymethylamine or N-acyloxyalkoxycarbonylamine.

The compound of the formula (1) or a prodrug thereof may be in the form of an isolated pure optical isomer, a partially purified optical isomer, a racemic mixture and a diastereomeric mixture, etc.

The preferable optical isomer is the optical isomer with the configuration of the formula (2):

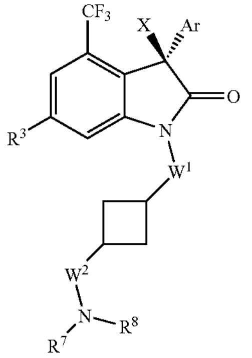

(2)

wherein $R^3$, $R^7$, $R^8$, X, Ar, $W^1$ and $W^2$ are the same as defined in [1]. These optical isomers can be usually differentiated by retention times in high performance liquid chromatography (Chiralcel OD-H™ (Daicel Chemical Industries, Ltd.), an eluent: 2-propanol/hexane), referred to as HPLC hereinafter. The preferable optical isomer usually elutes slower than other isomers.

The pharmaceutically acceptable salt of the compound of the formula (1) or a prodrug thereof includes, for example, a salt with an inorganic or an organic acid. The salt with an inorganic acid includes, for example, hydrochloride, hydrobromide, nitrate, sulfate or phosphate, etc. The salt with an organic acid includes, for example, formate, acetate, trifluoroacetate, propionate, lactate, tartrate, oxalate, fumarate, maleate, citrate, malonate, methanesulfonate or benzenesulfonate, etc.

When the compound of the formula (1) has an acidic functional group such as carboxy, the pharmaceutically acceptable salt may also include a salt with a base. The salt with a base includes, for example, a salt with an organic base such as arginine, lysine or triethyl ammonium, a salt with an inorganic base such as alkali metal (e.g., sodium or potassium) or alkali earth metal (e.g., calcium or barium), or ammonium salt, etc.

The compound of the formula (1) or its prodrug, or a pharmaceutically acceptable salt thereof may be in the form of a solvate such as hydrate.

The derivative of the formula (1) may be prepared according to the method described in, for example, WO2005/035498, more particularly the following methods.

Method A

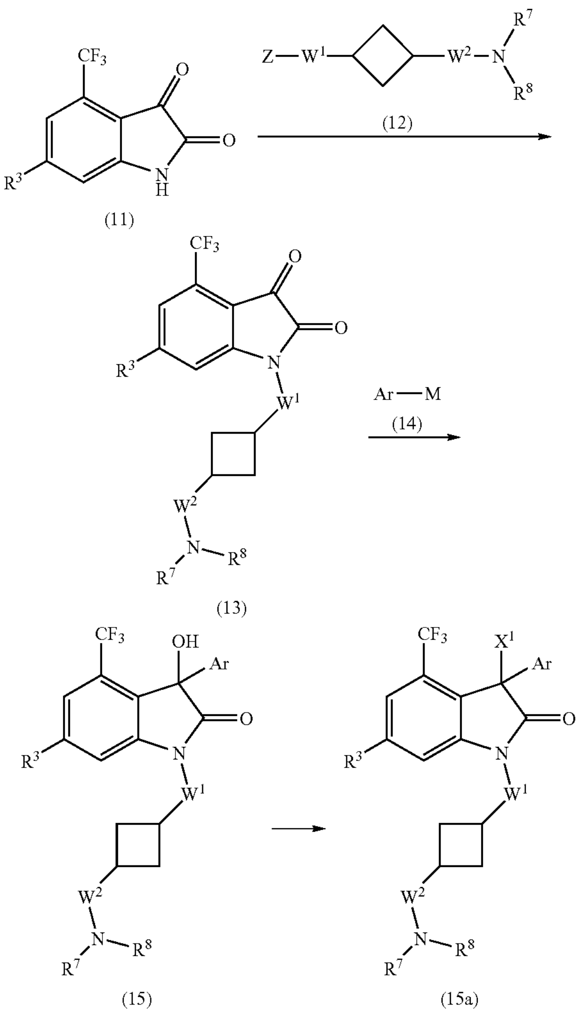

In the above scheme, $R^3$, $W^1$, $W^2$, Ar, $R^7$ and $R^8$ are the same as defined above. Z is chlorine atom, bromine atom, iodine atom, methanesulfonyloxy, toluenesulfonyloxy, trifluoromethanesulfonyloxy or hydroxyl, etc. M is lithium atom, magnesium bromide, magnesium iodide or magnesium chloride, etc. $X^1$ is the same as defined in the above X with the exception of hydroxyl.

Isatin derivative (11) may be reacted with compound (12) in the presence of a base to give compound (13). The reaction may be carried out according to conventional conditions of N-alkylation reaction. The base includes, for example, alkali hydride such as sodium hydride or potassium hydride, alkali amide such as sodium amide or lithium amide, or alkali alkoxide such as potassium t-butoxide or sodium methoxide. The amount of the base is usually in the range of 1 to 10 equivalent(s) to isatin derivative (11), preferably 1.5 to 5 equivalents, provided that, if a salt of compound (12) such as hydrochloride is used, the base may be added in excess amounts of the corresponding equivalents. The amount of compound (12) is usually in the range of 1 to 3 equivalent(s) to isatin derivative (11), preferably 1.2 to 2 equivalents. The reaction solvent includes, for example, an inactive organic solvent such as tetrahydrofuran, referred to as THF hereinafter, or N,N-dimethylformamide, referred to as DMF hereinafter. The reaction temperature is, for example, in the range of 0° C. to a boiling point of the reaction solvent, preferably in the range of room temperature to 80° C.

When Z is hydroxyl, compound (13) may be prepared by using an azo compound such as diethyl azodicarboxylate or diisopropyl azodicarboxylate, and a phosphoric reagent such as triphenylphosphine according to Mitsunobu method (see, for example, Synthesis, 1 (1981)). The reaction solvent includes, for example, an inactive solvent such as THF, and the reaction temperature includes, for example, in the range of 0° C. to a boiling point of the solvent.

Compound (13) may be reacted with compound (14) to give compound (15). The reaction of compound (13) with compound (14) may be carried out according to conventional reaction conditions. The amount of compound (14) is usually in the range of 1 to 2 equivalent(s) to compound (13). The reaction solvent includes, for example, ether solvents such as diethyl ether or THF. The reaction temperature is, for example, in the range of −78° C. to room temperature.

The hydroxyl of compound (15) may be converted into $C_1$-$C_4$ alkoxy, $C_1$-$C_4$ alkanoyloxy, chlorine atom or fluorine atom as necessary.

The compound (15) may be chlorinated using thionyl chloride to give compound (15a) wherein $X^1$ is chlorine atom. The chlorination is usually carried out in the range of room temperature to 50° C. in the absence of solvent.

The compound (15a) wherein $X^1$ is $C_1$-$C_4$ alkoxy, $C_1$-$C_4$ alkanoyloxy may be obtained by reacting compound (15) with the corresponding $C_1$-$C_4$ alkyl-$Z^1$ or $C_1$-$C_4$ alkanoyl-$Z^1$ wherein $Z^1$ is chlorine atom, bromine atom, iodine atom, methanesulfonyloxy or toluenesulfonyloxy in the presence of a base. The base includes, for example, alkali hydride such as sodium hydride or potassium hydride, alkali amide such as sodium amide or lithium amide, or an organic base such as triethylamine or ethyl diisopropylamine. The amount of the base is usually in the range of 1 to 10 equivalent(s) to compound (15) or the corresponding amine. The amount of $C_1$-$C_4$ alkyl-$Z^1$ or $C_1$-$C_4$ alkanoyl-$Z^1$ is usually in the range of 1 to 10 equivalent(s) to compound (15) or the corresponding amine. The reaction solvent includes, for example, an inactive solvent such as THF or DMF, etc. The reaction temperature is, for example, in the range of 0° C. to a boiling point of the reaction solvent, preferably in the range of room temperature to 80° C.

The conversion of hydroxyl group into fluorine atom in compound (15) may be carried out by reacting compound (15) with a fluorinating agent such as diethylaminosulfur trifluoride, tris-(dimethylamino)-sulfur-(trimethylsilyl)-difluoride or pyridium polyhydrofluoride. The hydroxyl group in compound (15) may be also converted into halogen atom such as chlorine atom, or sulfonate ester such as methanesulfonyl to react with metal fluoride such as silver fluoride or potassium fluoride. The amount of the fluorinating agent is usually in the range of 1 to 10 equivalent(s) to compound (15). The reaction solvent includes, for example, an inactive solvent such as dichloromethane or acetonitrile. The reaction temperature is, for example, in the range of −78° C. to 50° C., preferably in the range of room temperature to 80° C.

Method A-2

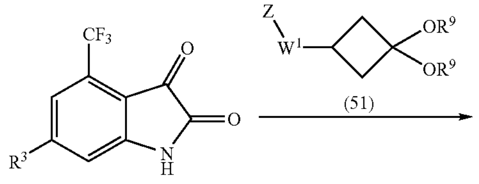

(11)

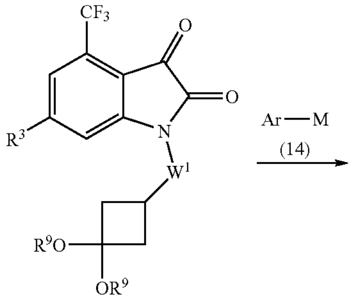

(52)

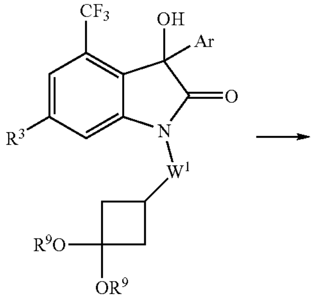

(53)

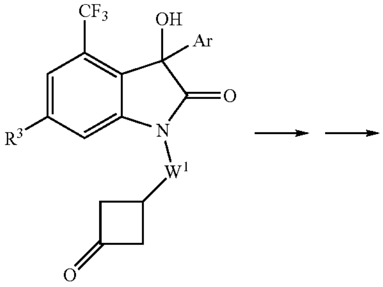

(54)

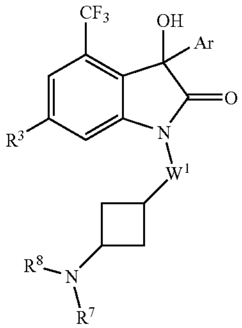

(55)

In the above scheme, $R^3$, $W^1$, Ar, $R^7$, $R^8$, Z and M are the same as defined above. $R^9$ is $C_1$-$C_4$ alkyl such as methyl, ethyl, t-butyl, or $C_7$-$C_{12}$ arylalkyl such as benzyl.

Cyclobutane derivative (51) may be reacted with isatin derivative (11) to give compound (52). Compound (52) may be reacted with compound (14) to give compound (53).

The method of synthesizing compound (53) from isatin derivative (11) may be carried out, for example, in a similar manner to the method of synthesizing compound (15) from compound (11) in the above Method A.

Compound (53) may be reacted in an inactive solvent such as acetone, water or a mixture thereof in the presence of a catalyst such as pyridinium p-toluenesulfonate to give compound (54).

Compound (54) may be reacted with the corresponding amine by a reductive amination to give compound (55). The reducing agent includes, for example, sodium cyanoborohydride, sodium borohydride or sodium triacetoxyborohydride. The reaction solvent includes, for example, an inactive organic solvent such as toluene, dichloromethane, methanol or DMF. The reaction temperature is, for example, in the range of 0° C. to a boiling point of the reaction solvent, preferably in the range of room temperature to 80° C.

Method B

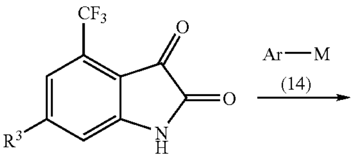

(11)

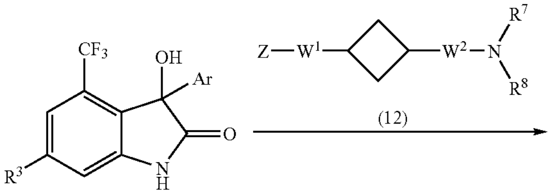

(18)

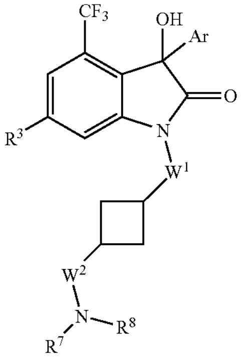

(15)

In the above scheme, $R^3$, $W^1$, $W^2$, Ar, $R^7$, $R^8$, Z and M are the same as defined above.

Isatin derivative (11) may be reacted with compound (14) in a similar manner to the reaction of compound (13) with compound (14) in Method A to give compound (18).

Then, compound (18) may be reacted with compound (12) in a similar manner to the reaction of isatin derivative (11) with compound (12) in Method A to give oxindole derivative (15).

In these reactions, protective and deprotective techniques may be used as necessary. The protective group of NH group at 1-position in isatin derivative (11) includes, for example, SEM (trimethylsilylethoxymethyl), etc. The protective group of hydroxyl group at 3-position in compound (18) includes, for example, TES (triethylsilyl), etc. The other protective groups, and introducing methods and deprotecting methods thereof may include the method described in Protective Groups in Organic Synthesis, T. W. Greene, A Wiley-Interscience Publication (1981), etc.

Method C

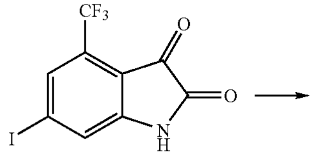

(16)

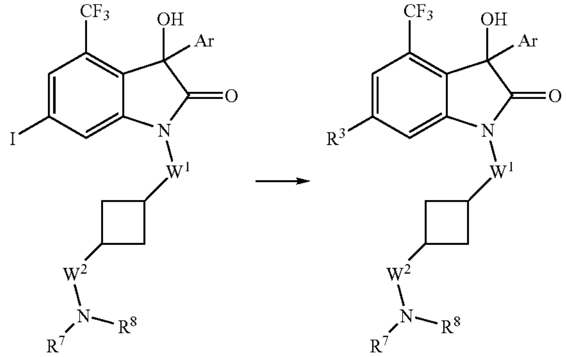

(17) (15)

In the above scheme, $R^3$, $W^1$, $W^2$, Ar, $R^7$ and $R^8$ are the same as defined above.

In Methods A and B, 6-iodo derivative (16) may be used as the isatin derivative to give compound (17).

Additionally, 6-iodo in the derivative may be converted into $R^3$ (except $R^3$=I) in a conventional manner to give compound (15). The conventional manner includes the reaction using a transition metal catalyst such as palladium including Heck reaction, Stille reaction, Kumada reaction, Suzuki reaction, Negishi reaction, Sonogashira reaction, etc.

The particular preparations may be, for example, the method described in Chemical Reviews, Vol. 105, pp. 2873 to 2920.

The racemic compound (17) may be optically resolved by the method using an optically active acid such as (R)- or (S)-methoxyphenylacetic acid, or the method using an optically active column to give an optically active compound.

The resulting optically active compound (17) may be treated in a similar manner to the above to give the optically active compound (15).

Method C-2

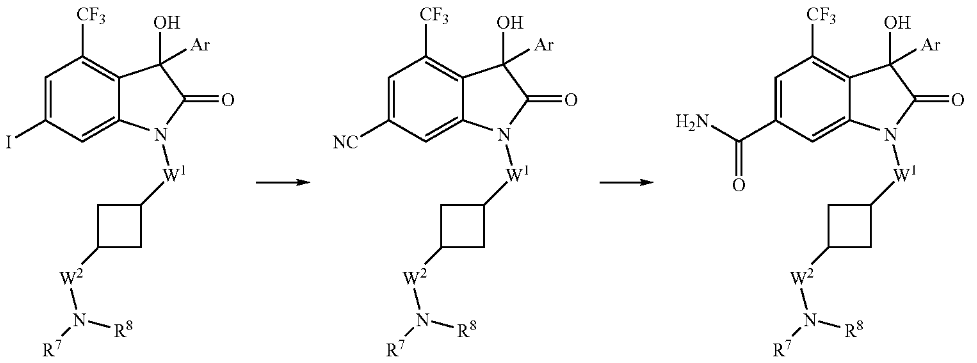

(17) (15a) (15b)

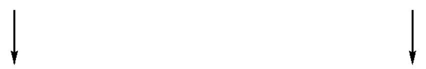

-continued

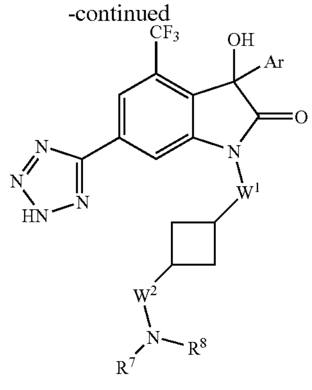

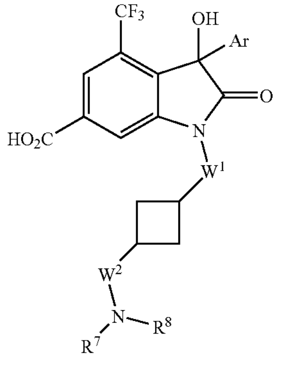

(15c) (15d)

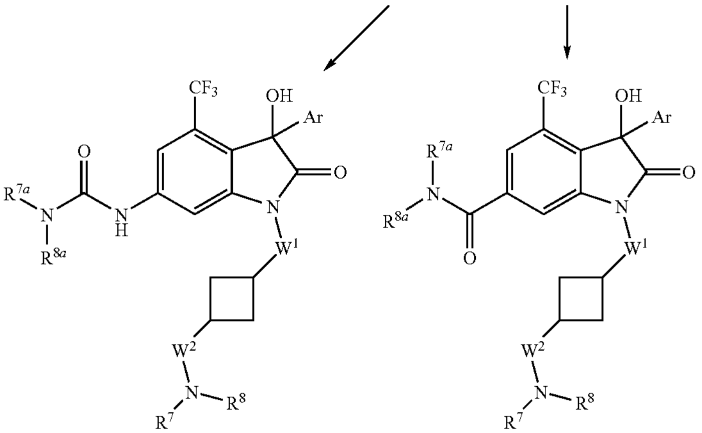

(15f) (15e)

In the above scheme, $W^1$, $W^2$, Ar, $R^7$ and $R^8$ are the same as defined above. $R^{7a}$ and $R^{8a}$ are the same as defined in $R^7$ and $R^8$.

For example, compound (17) may be reacted with a cyanide compound such as zinc cyanide in an inactive solvent such as DMF in the presence of a catalyst such as tetrakisphosphine palladium to give compound (15a).

For example, compound (15a) may be reacted with a base such as potassium hydroxide in an inactive solvent such as t-butyl alcohol to give compound (15b).

For example, compound (15a) may be reacted with sodium azide in an inactive solvent such as toluene in the presence of an additive such as triethylamine hydrochloride to give compound (15c).

For example, compound (15b) may be reacted with acid such as hydrobromic acid in a solvent such as acetic acid to give compound (15d).

For example, compound (15d) and amine compound may be reacted with a condensing agent such as bis-(2-oxo-3-oxazolidinyl)-phosphinic chloride in an inactive solvent such as DMF to give compound (15e).

Compound (15d) and diphenylphosphoryl azide may be reacted with a base such as triethylamine in an inactive solvent such as toluene, followed by reacting with the corresponding amine to give compound (15f).

Method C-3

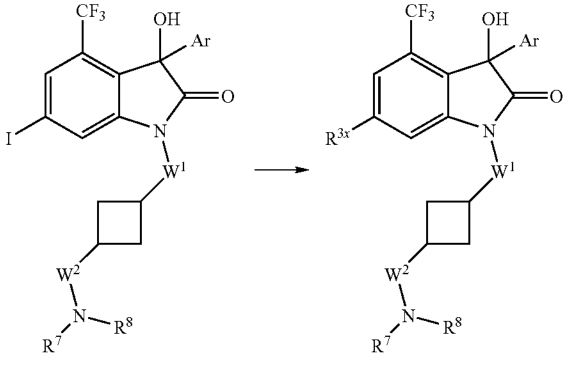

(17) (15g)

In the above scheme, $W^1$, $W^2$, Ar, $R^7$ and $R^8$ are the same as defined above. $R^{3x}$ is optionally substituted heteroaryl, optionally substituted saturated heterocycle, optionally substituted amino, optionally substituted alkylsulfonylamino, or optionally substituted arylsulfonylamino.

For example, compound (17) may be reacted with $R^{3x}$—H in the presence of a base such as n-butyl lithium, an additive such as zinc chloride, and a catalyst such as tetrakisphosphine palladium in an inactive solvent such as tetrahydrofuran to give compound (15g).

For example, compound (17) may be also reacted with $R^{3x}$-$M^1$ wherein $M^1$ is, for example, tributyltin, etc. in the presence of a catalyst such as tetrakisphosphine palladium in an inactive solvent such as toluene to give compound (15g).

For example, compound (17) may be also reacted with $R^{3x}$—H in the presence of a base such as potassium phosphate, dimethylethylenediamine, and copper (I) iodide in an inactive solvent such as DMF to give compound (15g).

Method C-4

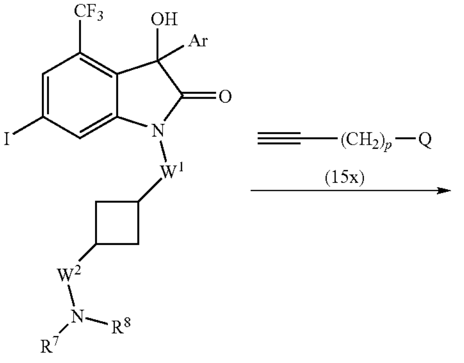

(17)

(15x)

-continued

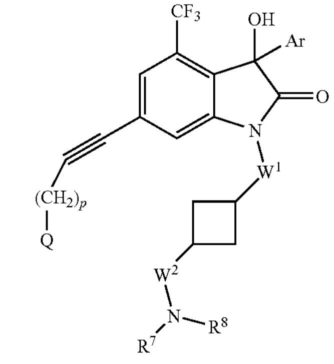

(15h)

In the above scheme, $W^1$, $W^2$, Ar, p, Q, $R^7$ and $R^8$ are the same as defined above.

Compound (17) may be reacted with compound (15x) in the presence of a base such as triethylamine, and a catalyst such as dichloro bistriphenylphosphine palladium and copper iodide to give compound (15h).

Isatin derivative (11) may be prepared according to the method described in, for example, WO2005/035498.

Among the compounds of the formula (12), the compounds of the formulae (21), (23) and (28) may be prepared according to, for example, the following method.

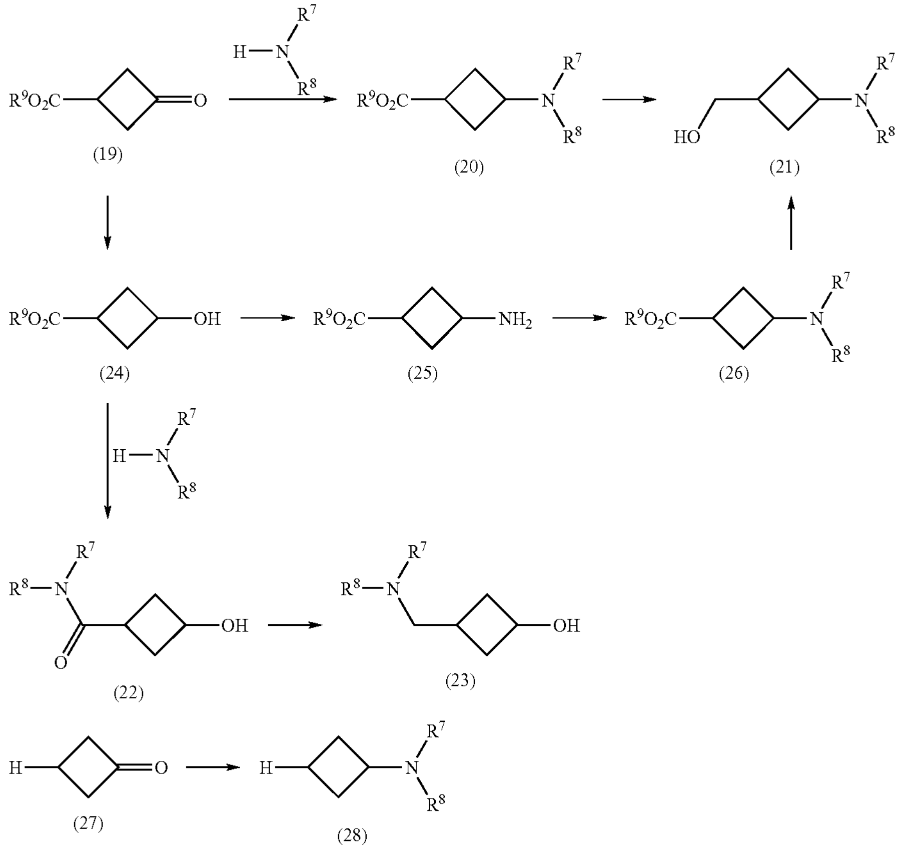

(19) (20) (21) (24) (25) (26) (22) (23) (27) (28)

In the above scheme, $R^7$ and $R^8$ are the same as defined above. $R^9$ is $C_1$-$C_4$ alkyl such as methyl, ethyl, t-butyl, or $C_7$-$C_{12}$ arylalkyl such as benzyl.

Compound (19) may be reacted with the corresponding amine by a reductive amination reaction to give compound (20). The reducing agent includes, for example, sodium cyanoborohydride, sodium borohydride or sodium triacetoxyborohydride, etc. The reaction solvent includes, for example, an inactive organic solvent such as toluene, methylene chloride, methanol or DMF, etc. The reaction temperature is, for example, in the range of 0° C. to a boiling point of the reaction solvent, preferably in the range of room temperature to 80° C.

Compound (20) may be reduced to give compound (21). The reducing agent includes, for example, lithium aluminum hydride, dibutylaluminum hydride or lithium borohydride, etc. The reaction solvent includes, for example, an inactive organic solvent such as toluene, methylene chloride, THF or diethyl ether, etc. The reaction temperature is, for example, in the range of −78° C. to a boiling point of the reaction solvent, preferably in the range of 0° C. to 80° C.

Alternatively, compound (19) may be treated with a reducing agent such as sodium borohydride to give compound (24), followed by converting the resulting compound into compound (25). By the conversion, for example, compound (24) may be chlorinated using thionyl chloride, or methanesulfonylated using methanesulfonyl chloride and base such as triethylamine, followed by an azidation, and subsequently reduced to give compound (25). The chlorination is usually carried out in neat in the range of room temperature to 50° C. The methanesulfonylation is carried out in an inactive solvent such as methylene chloride, toluene, THF, etc. in the range of 0° C. to 80° C. The azidation is, for example, carried out using an azidating agent such as sodium azide or trimethylsilyl azide in the presence of a base such as triethylamine in an inactive solvent such as THF or DMF in the range of room temperature to 80° C. The reducing agent includes, for example, tin (II) chloride, etc. The reaction solvent includes, for example, alcoholic solvent such as methanol or ethanol. The reaction temperature is in the range of room temperature to a boiling point of the solvent.

Compound (25) may be reductively aminated using the corresponding aldehyde or ketone to give compound (26), followed by reduction of compound (26) to give compound (21). The conditions of the reductive amination and reduction are those described in the above.

Compound (24) may be amidated with the corresponding amine to give compound (22). The reagent for amidation includes, for example, Lewis acid such as aluminum chloride or diethylaluminum chloride. The reaction solvent includes, for example, inactive solvent such as methylene chloride or toluene. The reaction temperature is in the range of room temperature to a boiling point of the solvent.

Compound (22) may be reduced to give compound (23). The reducing agent includes, for example, lithium aluminum hydride, dibutylaluminum hydride or lithium borohydride, etc. The reaction solvent includes, for example, an inactive organic solvent such as toluene, methylene chloride, THE or diethyl ether. The reaction temperature is, for example, in the range of −78° C. to a boiling point of the reaction solvent, preferably in the range of 0° C. to 80° C.

Compound (27) may be reductively aminated with the corresponding amine to give compound (28). The conditions of the reductive amination are those described in the above.

The compound of the formula (21) may be also synthesized according to, for example, the following method.

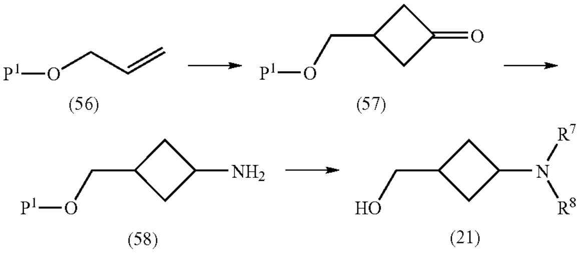

(56) (57) (58) (21)

In the above scheme, $R^7$ and $R^8$ are the same as defined above. $P^1$ is a protective group of hydroxyl group.

For example, compound (56) may be reacted with trichloroacetyl chloride, etc. in an inactive solvent such as ether in the presence of zinc, and the resulting compound may be reacted with zinc in a solvent such as acetic acid, pyridine to give compound (57).

For example, compound (57) may be treated in a similar manner to the above synthesis of compound (25) from compound (19) to give compound (58).

For example, compound (58) may be converted into compound (21) by a reductive amination, a reduction following synthesizing amide compound, an alkylation, etc.

The compounds of the formulae (21), (23) and (28) may be obtained in a mixture of cis- and trans-isomers depending on the reaction conditions and the kinds of substrates. These isomers may be isolated by a conventional column chromatography or a recrystallization.

The compound of the formula (29) represented by the compounds of the formulae (21), (23) and (28) may be induced to the compound of the formula (12a) according to, for example, the following method.

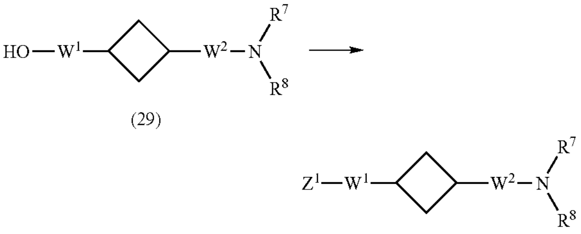

(29) (12a)

In the above scheme, $W^1$, $W^2$, $R^7$ and $R^8$ are the same as defined above, $Z^1$ is chlorine atom, bromine atom, iodine atom, methanesulfonyloxy, toluenesulfonyloxy, trifluoromethanesulfonyloxy, etc.

The hydroxyl group of compound (29) may be converted into chlorine atom, bromine atom, iodine atom, methanesulfonyloxy, toluenesulfonyloxy, trifluoromethanesulfonyloxy, etc. as necessary.

Among compounds (12a), the compound wherein $Z^1$ is methanesulfonyloxy, toluenesulfonyloxy or trifluoromethanesulfonyloxy may be obtained by reacting compound (29) with the corresponding sulfonyl chloride in the presence of a base such as triethylamine in an inactive solvent such as methylene chloride, toluene, THF in the range of 0° C. to 80° C.

Among compounds (12a), the compound wherein $Z^1$ is chlorine atom may be usually obtained by reacting compound (29) with thionyl chloride, etc. in neat in the range of room temperature to 50° C.

Among compounds (12a), the compound wherein $Z^1$ is bromine atom may be obtained by reacting compound (29) with triphenylphosphine and carbon tetrabromide or N-bromosuccinimide, etc. For example, the reaction is carried out in an inactive solvent such as methylene chloride, toluene, THF in the range of 0° C. to 80° C.

Among compounds (12a), the compound wherein $Z^1$ is iodine atom may be obtained by reacting compound (29) with triphenylphosphine, iodine atom, and imidazole, etc. For example, the reaction is carried out in an inactive solvent such as methylene chloride, toluene, THF in the range of 0° C. to 80° C.

In the above reactions, any functional group of each compound may be protected as necessary. The known protective groups (see, for example, Protective Groups in Organic Synthesis, T. W. Greene, A Wiley-Interscience Publication (1981)) may be used as the protective group.

Starting materials and reagents used in the above may be, unless otherwise specified, commercially available or may be prepared from known compounds using known methods.

Compound (1) prepared according to the above preparation may be obtained as a mixture of isomers. In this case, each isomer may be isolated in the final or intermediate step by an appropriate purification method such as silica gel column chromatography.

Compound (1), or particularly, compound (1) wherein $R^3$ is iodine atom may be also optically resolved by known methods such as a fractional recrystallization of an addition salt with an optically active acid such as α-methoxyphenylacetic acid, phenylacetic acid, tartaric acid, or high-performance liquid chromatography using an optically active column to give an optical isomer of compound (1).

A prodrug of compound (1) may be obtained according to the conventional method (e.g., Chemistry and Industry, 1980, 435; Advanced Drug Discovery Reviews 3, 39 (1989)).

A pharmaceutically acceptable salt of compound (1) or its prodrug may be prepared by mixing compound (1) or its prodrug with a pharmaceutically acceptable acid such as hydrochloric acid, citric acid or methanesulfonic acid in a solvent such as water, methanol, ethanol or acetone.

Particularly, preferable compounds (1) are the following:

4-trifluoromethyl-3-(2-chlorophenyl)-1-[3-(diethylamino)-cyclobutyl]-3-hydroxy-2-oxoindoline-6-carboxamide;

4-trifluoromethyl-3-(2-chlorophenyl)-1-{[3-(diethylamino)-cyclobutyl]-methyl}-3-hydroxy-2-oxoindoline-6-carboxamide.

The present compound may be used as a preventive and/or therapeutic agent for the following diseases by its feeding controlling activity: diabetes, diabetic complication such as diabetic nephropathy and diabetes, obesity, hyperlipidemia, arteriosclerosis, hypertension, feeding disorder (overeating), affective disorder, memory disorder, dementia, hormonal disorder, sexual dysfunction, gonarthritis, metabolic syndrome.

The present compound may be administered orally or parenterally (intramuscularly, intravenously, subcutaneously, transdermally, intranasally, by suppository, by eye drops, intracerebrally). A dosage form includes a commonly acceptable dosage form, for example, powders, granules, subtle granules, tablets, capsules, pills, syrups, suspensions, injections such as liquids, emulsions, rectal suppositories, transdermal formulations (e.g., ointments, creams, lotions), etc.

Formulation may be prepared by the conventional method using a conventional carrier or diluent. A solid formulation such as a tablet may be prepared by mixing an active compound with a conventional pharmaceutically acceptable carrier or excipient (e.g., lactose, sucrose, corn starch), binder (e.g., hydroxypropylcellulose, polyvinylpyrrolidone, hydroxypropylmethylcellulose), disintegrant (e.g., sodium carboxymethylcellulose, sodium starch glycolate), lubricant (e.g., stearic acid, magnesium stearate) or preservative, etc. The parenteral agent such as liquid, suspension may be prepared by dissolving or suspending an active compound in a physiologically acceptable carrier or diluent such as water, saline, oil, dextrose solution, and additionally adding thereto an adjuvant such as pH regulator, buffer, stabilizer, solubilizer, emulsifier, osmotic regulator as necessary.

The dose and the number of administration of the present compound generally depend on administration routes, degrees of conditions and weights of patients, etc. The present compound is usually administered in an amount of about 1 mg to about 1 g, preferably about 1 mg to about 200 mg, more preferably about 5 mg to about 50 mg at one or more times per day for adult (weight 60 kg). It may be administered one time during 2 days to 1 week. No toxicity has been observed in the dosage to be used in said treatment.

The present compound may be used in combination with other drugs such as an agent for diabetes, an agent for diabetic complication, an antihyperlipidemia agent, an antihypertensive agent, an antiobesity agent or a diuretic agent (which is referred to as "combined drug" hereinafter), for the purpose of enhancing the effect of the present compound. The present compound and the combined drug may be administered simultaneously or separately at an interval to the subject without any limitation for administration time. The dosage of the combined drug may be optionally selected on the basis of a clinically used dose. The ratio of the present compound and the combined drug may be optionally selected depending on subjects, administration routes, diseases, conditions of the subjects, or a combination thereof. For example, in case that the subject is human, the combined drug may be used in 0.01 to 100 parts by weight to 1 part by weight of the present compound.

The agent for diabetes includes an insulin formulation (e.g., animal insulin formulation obtained by extraction from the pancreas of bovine or swine; human insulin formulation prepared by genetic engineering technique using *Escherichia coli* or yeast, etc.), an insulin sensitizer (e.g., pioglitazone or hydrochloride thereof, troglitazone, rosiglitazone or maleate thereof, muraglitazar, tesaglitazar, naveglitazar, metaglitasen), an α-glucosidase inhibitor (e.g., voglibose, acarbose, miglitol, emiglitate), a biguanide preparation (e.g., metformin), an insulin secretagogue (e.g., sulfonylurea preparation such as tolbutamide, glibenclamide, gliclazide, chlorpropamide, tolazamide, acetohexamide, glyclopyramide, glimepiride; repaglinide, senaglinide, nateglinide, mitiglinide, etc.), a GLP-1, GLP-1 analog (e.g., exenatide, liraglutide, SUN-E7001, AVE010, BIM-51077, CJC1131, etc.), a protein tyrosine phosphatase inhibitor (e.g., vanadic acid), a β3 agonist (e.g., GW-427353B, N-5984).

The agent for diabetic complication includes an aldose reductase inhibitor (e.g., tolrestat, epalrestat, zenarestat, zopolrestat, minalrestat, fidarestat, SK860, CT-112), a neurotrophic factor (e.g., NGF, NT-3, BDNF), a PKC inhibitor (e.g., LY-333531), an AGE inhibitor (e.g., ALT946, pimagedin, piratoxatine, N-phenacylthiazolium bromide (ALT766)), an elimination agent for active oxygen (e.g., thioctic acid), a cerebral blood vessel dilator (e.g., tiapride, mexiletine). The antilipidemic agent includes a HMG-CoA reductase inhibitor (e.g., pravastatin, simvastatin, lovastatin, atorvastatin, fluvastatin, itavastatin or a sodium salt thereof), a squalene synthetase inhibitor, an ACAT inhibitor, etc. The antihypertensive agent includes an angiotensin-converting enzyme inhibitor (e.g., captopril, enalapril, alacepril, delapril, lisinopril, imidapril, benazepril, cilazapril, temokapril, trandrapril), an angiotensin II antagonist (e.g., candesartan cilexetil, losartan, eprosartan, valsartan, telmisartan, irbesartan, tasosartan), a calcium antagonist (e.g., nicardipine hydrochloride, manidipine hydrochloride, nisoldipine, nitrendipine, nilvadipine, amlodipine), etc.

The antiobesity agent includes, for example, a central anti-obesity agent (e.g., phentermine, sibutramine, amfepramone, dexamfetamine, mazindol, SR-141716A), a pancreatic lipase inhibitor (e.g., orlistat), a peptidic anorectic drug (e.g., leptin, CNTF (ciliary neurotrophic factor)), a cholecystokinin agonist (e.g., lintitript, FPL-15849), etc. The diuretic agent includes, for example, a xanthine derivative (e.g., theobromine sodium salicylate, theobromine calcium salicylate), a thiazide formulation (e.g., ethiazide, cyclopenthiazide, trichloromethiazide, hydrochlorothiazide, hydroflumethiazide, bentylhydrochlorothiazide, penflutizide, polythiazide, methylclothiazide), an antialdosterone formulation (e.g., spironolactone, triamterene), a carbonic anhydrase inhibitor (e.g., acetazolamide), a chlorobenzenesulfonamide formulation (e.g., chlorthalidone, mefruside, indapamide), azosemide, isosorbide, etacrynic acid, piretanide, bumetanide, furosemide, etc.

Preferable combined drugs are a GLP-1, GLP-1 analog, an α-glucosidase inhibitor, a biguanide preparation, an insulin secretagogue, an insulin sensitizer, etc. Two or more kinds of the combined drugs may be used in any combination ratio.

In case that the present compound is used in combination with the combined drugs, the dose of the drugs may be reduced into the safe range in view of side effects of the drugs. Particularly, the dose of the biguanide preparation can be reduced than the usual dosage. Therefore, side effects caused by the drugs may be prevented in safety. Moreover, dosages of a diabetic complication agent, an antihyperlipidemia agent, an antihypertensive agent may be reduced, and hence, side effects caused by these drugs may be effectively prevented.

The present invention is specifically illustrated by the following Examples, but it is not limited thereto. The following abbreviation may be used for the purpose of a simplification of the description herein.

Me: methyl

Et: ethyl

Bn: benzyl

Bz: benzoyl

Ms: methanesulfonyl

SEM: 2-(trimethylsilyl)-ethoxymethyl

TES: triethylsilyl

TBD MS: tert-butyldimethylsilyl

EXAMPLES

Reference Example 1-1

1-[2-(trimethylsilyl)-ethoxymethyl]-4-trifluoromethyl-6-iodo-1H-indole-2,3-dione

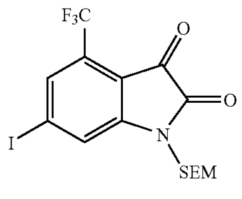

A solution of 4-trifluoromethyl-6-iodo-1H-indole-2,3-dione (12.0 g, 35.2 mmol) in N,N-dimethylformamide (120 mL) was cooled to 0° C. under nitrogen, and thereto was added 55% sodium hydride (1.70 g, 39.0 mmol) and the mixture was stirred for 30 minutes. Then, to the reaction solution was added dropwise 2-(trimethylsilyl)-ethoxymethyl chloride (7.00 mL, 39.6 mmol), and the mixture was stirred at room temperature for 5 minutes. To the reaction solution was added water, and the mixture was extracted with ethyl acetate-toluene (1:1) twice, washed with water twice, and then dried over magnesium sulfate, and filtered. The filtrate was evaporated and purified by silica gel column chromatography (hexane/ethyl acetate=5/1) to give the titled compound (13.7 g, 83%).

$^1H$ NMR ($CDCl_3$, 400 MHz) δ 7.80 (s, 1H,), 7.79 (s, 1H,), 5.19 (s, 2H,), 3.58-3.62 (m, 2H), 0.93-0.97 (m, 2H), 0.00 (s, 9H).

Reference Example 1-2

3-(2,4-dichlorophenyl)-1-[2-(trimethylsilyl)-ethoxymethyl]-4-trifluoromethyl-3-hydroxy-6-iodo-1,3-dihydro-2H-indol-2-one

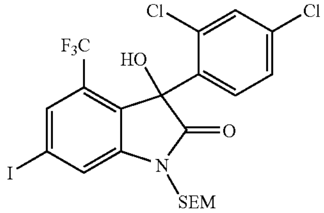

A solution of the compound of Reference example 1-1 (13.5 g, 28.6 mmol) in tetrahydrofuran (100 mL) was cooled to −78° C. under nitrogen, and thereto was added dropwise 0.482N 2,4-dichlorophenyl magnesium iodide ether solution (90 mL, 43.4 mmol) prepared separately, and the mixture was stirred for 30 minutes. To the reaction solution was added 5% aqueous sodium bisulfate solution, and the mixture was extracted with ethyl acetate twice, and washed with saturated saline, and then dried over magnesium sulfate, and filtered. The filtrate was evaporated and purified by silica gel column chromatography (hexane/ethyl acetate=10/1 to 5/1) to give the titled compound (15.3 g, 87%).

$^1H$ NMR ($CDCl_3$, 400 MHz) δ 7.98 (d, 1H, J=8.5 Hz), 7.71 (s, 1H,), 7.68 (s, 1H,), 7.40 (dd, 1H, J=2.1, 8.5 Hz), 7.29 (d, 1H, J=2.1 Hz), 5.23 (d, 1H, J=11.3 Hz), 5.18 (d, 1H, J=11.3 Hz), 3.62-3.70 (m, 2H), 0.93-0.98 (m, 2H), 0.00 (s, 9H).

Reference Example 1-3

3-(2,4-dichlorophenyl)-4-trifluoromethyl-3-hydroxy-6-iodo-1,3-dihydro-2H-indol-2-one

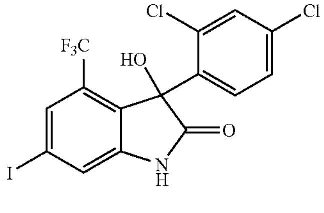

To a solution of the compound of Reference example 1-2 (14.7 g, 23.7 mmol) in tetrahydrofuran (100 mL) was added tetrabutyl ammonium fluoride (13.8 g, 52.8 mmol) under nitrogen, and the mixture was heated to reflux. Thereto was added additional tetrabutyl ammonium fluoride (10.5 g, 40.2 mmol), and the mixture was heated to reflux for a total of 64 hours. To the reaction solution was added 5% aqueous sodium bisulfate solution, and the mixture was extracted with ethyl acetate, washed with saturated saline, dried over magnesium sulfate, and filtered. The filtrate was evaporated and purified by silica gel column chromatography (hexane/ethyl acetate=3/1 to 1/1) to give the titled compound (9.04 g, 78%).

$^1$H NMR ($CDCl_3$, 400 MHz) δ 8.74 (brs, 1H), 7.96 (d, 1H, J=8.6 Hz), 7.62 (d, 1H, J=0.6 Hz), 7.40-7.42 (m, 2H), 7.30 (d, 1H, J=2.1 Hz), 3.77 (brs, 1H).

Reference Example 1-4

3-(2,4-dichlorophenyl)-4-trifluoromethyl-3-triethylsilyloxy-6-iodo-1,3-dihydro-2H-indol-2-one

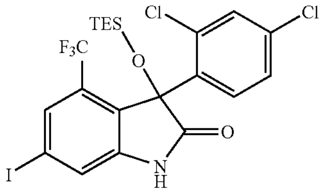

A solution of the compound of Reference example 1-3 (3.10 g, 6.35 mmol) in N,N-dimethylformamide (30 mL) was cooled to 0° C. under nitrogen, and thereto was added 55% sodium hydride (700 mg, 16.0 mmol) and the mixture was stirred for 30 minutes. Then, thereto was added dropwise chlorotriethylsilane (1.80 mL, 10.7 mmol), and the mixture was stirred at room temperature for 5 hours. To the reaction solution was added water, and the mixture was extracted with ethyl acetate-toluene (1:1), water and saturated saline sequentially, and then dried over magnesium sulfate, and filtered. The filtrate was evaporated and purified by silica gel column chromatography (hexane/ethyl acetate=10/1 to 5/1) to give the titled compound (3.58 g, 94%).

$^1$H NMR ($CDCl_3$, 400 MHz) δ 8.72 (brs, 1H), 8.04 (d, 1H, J=8.6 Hz), 7.60 (d, 1H, J=0.6 Hz), 7.45 (d, 1H, J=0.6 Hz), 7.39 (d, 1H, J=2.1, 8.6 Hz), 7.25 (d, 1H, J=2.1 Hz), 0.87 (t, 9H, J=7.8 Hz), 0.52 (q, 6H, J=7.8 Hz).

Reference Example 2-1

3-tert-butyldimethylsilyloxycyclobutanone

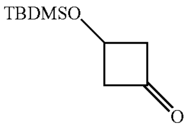

To a solution of 2,2-dichloro-3-tert-butyldimethylsilyloxy-cyclobutanone (see, for example, Journal of Organic Chemistry, 44, 2560 (1979)) (3.20 g, 11.9 mmol) in saturated ammonium chloride methanol (70 mL) was added zinc-copper couple (3.89 g, 59.5 mmol) under nitrogen, and the mixture was stirred at room temperature for 24 hours. The mixture was evaporated, and then thereto was added water and the mixture was extracted with ethyl acetate, washed with saturated ammonium chloride water, and then dried over magnesium sulfate, and filtered. The filtrate was evaporated and purified by silica gel column chromatography (hexane/ethyl acetate=5/1) to give the titled compound (914 mg, 38%) as a colorless oil.

$^1$H NMR ($CDCl_3$, 400 MHz) δ 4.58-4.63 (m, 1H), 3.22-3.33 (m, 2H), 3.04-3.12 (m, 2H), 0.91 (s, 9H), 0.10 (s, 6H).

Reference Example 2-2 cis-1-diethylamino-3-tert-butyldimethylsilyloxycyclobutane

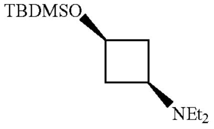

To a solution of the compound of Reference example 2-1 (500 mg, 2.50 mmol) in dichloromethane (5.0 mL) were successively added diethylamine (0.30 mL, 2.90 mmol) and acetic acid (0.15 mL, 2.62 mmol) under nitrogen, and the mixture was stirred at room temperature for 1 hour. Then, thereto was added sodium triacetoxyborohydride (700 mg, 3.30 mmol), and the mixture was stirred at room temperature for 24 hours. The reaction solution was poured into saturated aqueous sodium bicarbonate, and the mixture was extracted with ethyl acetate twice, dried over magnesium sulfate, and filtered. The filtrate was evaporated and purified by silica gel column chromatography (chloroform/methanol=20/1 to 10/1) to give the titled compound (224 mg, 35%) as a colorless solid.

$^1$H NMR ($CDCl_3$, 400 MHz) δ 3.91-3.98 (m, 1H), 2.54-2.63 (m, 5H), 2.40-2.46 (m, 2H), 1.89-1.91 (m, 2H), 1.00 (t, 6H, J=7.2 Hz), 0.87 (s, 9H), 0.02 (s, 6H).

Reference Example 2-3 cis-1-diethylamino-3-hydroxycyclobutane

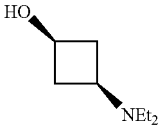

To a solution of the compound of Reference example 2-2 (195 mg, 0.757 mmol) in methanol (6.0 mL) was added an aqueous hydrochloric acid solution (1.00 mL) under nitrogen, and the mixture was stirred overnight. The mixture was evaporated, and thereto was added water and the aqueous layer was washed with diethyl ether three times. The aqueous layer was concentrated to dryness to give cis-1-diethylamino-3-hydroxycyclobutane hydrochloride (141 mg) as a colorless solid.

$^1$H NMR ($CD_3OD$, 400 MHz) δ 4.04-4.12 (m, 1H), 3.37-3.45 (m, 1H), 3.10-3.30 (m, 4H), 2.75-2.82 (m, 2H), 2.09-2.16 (m, 2H), 1.27 (t, 6H, J=7.4 Hz), 0.87 (s, 9H), 0.02 (s, 6H).

Cis-1-diethylamino-3-hydroxycyclobutane hydrochloride (100 mg, 0.557 mmol) was dissolved in methanol (3.0 ml), and thereto was added 1N aqueous sodium hydroxide solution (0.560 mL, 0.560 mmol). The mixture was evaporated, and thereto were added ethyl acetate and tetrahydrofuran, and the mixture was dried over sodium sulfate, and filtered. The filtrate was evaporated to give the titled compound (71.7 mg).

Reference Example 3-1 trans-1-diethylamino-3-benzoyloxycyclobutane

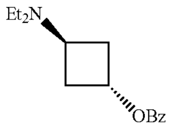

A solution of the compound of Reference example 2-3 (198 mg, 1.38 mmol) in tetrahydrofuran (7.0 mL) was cooled to 0° C. under nitrogen, and thereto were successively added triphenylphosphine (450 mg, 1.72 mmol), diisopropylazodicarboxylate (340 μL, 1.73 mmol), benzoic acid (190 mg, 1.56 mmol), and the mixture was stirred at 0° C. for 3 hours. The mixture was evaporated and purified by silica gel column chromatography (chloroform/methanol=30/1 to 20/1) to give the titled compound (524 mg).

$^1$H NMR ($CDCl_3$, 400 MHz) δ 7.40-7.72 (m, 5H), 5.27-5.31 (m, 1H), 3.59-3.62 (m, 1H), 2.68-2.77 (m, 6H), 2.38-2.43 (m, 2H), 1.10 (t, 6H, J=7.2 Hz).

Reference Example 3-2 trans-1-diethylamino-3-hydroxycyclobutane

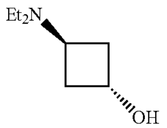

To the compound of Reference example 3-1 (470 mg) were added tetrahydrofuran (3.0 mL), methanol (3.0 mL) and 1N aqueous sodium hydroxide solution (3.00 mL, 3.00 mmol) at room temperature for 3 hours under nitrogen. The mixture was evaporated, and thereto was added 3N hydrochloric acid water (3.0 mL), and the mixture was washed with diethyl ether three times. The aqueous layer was evaporated, and thereto was added 1N aqueous sodium hydroxide solution (2.0 mL), and the mixture was extracted with diethyl ether four times, dried over sodium sulfate, and filtered. The filtrate was evaporated, and thereto was added 4N aqueous hydrochloric acid solution, and the mixture was evaporated. Thereto was added toluene, and the mixture was evaporated to give trans-1-diethylamino-3-hydroxycyclobutane hydrochloride (197 mg, 88%, 2 steps).

$^1$H NMR ($CD_3OD$, 400 MHz) δ 4.36-4.40 (m, 1H), 4.01-4.11 (m, 1H), 3.06-3.25 (m, 4H), 2.57-2.65 (m, 2H), 2.26-2.32 (m, 2H), 1.28 (t, 6H, J=7.4 Hz).

Trans-1-diethylamino-3-hydroxycyclobutane hydrochloride (197 mg, 1.10 mmol) was dissolved in methanol (3.0 mL), and thereto was added 1N aqueous sodium hydroxide solution (1.10 mL, 1.10 mmol). The mixture was evaporated, and thereto were added ethyl acetate and tetrahydrofuran, and the mixture was dried over sodium sulfate, and filtered. The filtrate was evaporated to give the titled compound.

Reference Example 4

3-(2,4-dichlorophenyl)-1-[3-oxocyclobutylmethyl]-4-trifluoromethyl-3-hydroxy-6-iodo-1,3-dihydro-2H-indol-2-one Reference Example 4-1

3,3-dimethoxycyclobutane Carboxylic Methyl Ester

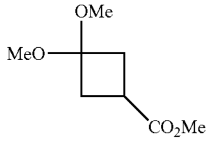

To a solution of 3-oxocyclobutane carboxylic benzyl ester (613 mg, 3 mmol) in toluene (6 mL) were added methanol (1.2 mL) and p-toluenesulfonic acid monohydrate (57 mg, 0.3 mmol), and the mixture was heated to reflux for 10 hours. The reaction solution was concentrated, and then thereto was added saturated aqueous sodium bicarbonate, and the mixture was extracted with ethyl acetate, dried over magnesium sulfate, and then filtered. The filtrate was evaporated and purified by silica gel column chromatography (n-hexane/ethyl acetate=20/1 to 3/1) to give the titled compound (378 mg, 72%).

$^1$H NMR ($CDCl_3$, 400 MHz) δ 3.70 (s, 3H), 3.17 (s, 3H), 3.15 (s, 3H), 2.94-2.84 (m, 1H), 2.48-2.34 (m, 4H).

Reference Example 4-2

(3,3-dimethoxycyclobutyl)-methanol

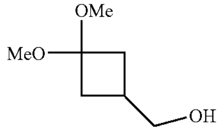

To a solution of lithium aluminum hydride (58 mg, 1.53 mmol) in tetrahydrofuran (4 mL) was added dropwise a solution of the compound of Reference example 4-1 (378 mg, 2.17 mmol) in tetrahydrofuran (3.6 mL) at 0° C., and the mixture was stirred for 30 minutes. To the reaction solution were successively added water (58 μL), 4M aqueous sodium hydroxide solution (58 μL), water (174 μL), and the mixture was filtered through celite. The filtrate was concentrated and purified by silica gel column chromatography (n-hexane/ethyl acetate=3/1 to 1/1) to give the titled compound (244 mg, 77%).

$^1$H NMR ($CDCl_3$, 400 MHz) δ 3.66 (dd, 2H, J=3.4, 7.1 Hz), 3.16 (s, 3H), 3.14 (s, 3H), 2.33-2.13 (m, 3H), 1.95-1.83 (m, 2H), 1.54 (t, 1H, J=3.4 Hz).

Reference Example 4-3

1-[3,3-dimethoxycyclobutylmethyl]-4-trifluoromethyl-6-iodo-1H-indole-2,3-dione

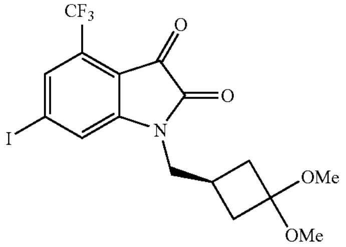

The compound of Reference example 4-2 (244 mg, 1.67 mmol) was used in a similar manner to Example 1-1 to give the titled compound (549 mg, 70%).

$^1$H NMR ($CDCl_3$, 400 MHz) δ 7.74 (s, 1H), 7.55 (s, 1H), 3.86 (d, 2H, J=8.0 Hz), 3.18 (s, 3H), 3.15 (s, 3H), 2.57-2.47 (m, 1H), 2.38-2.28 (m, 2H), 1.96 (dd, 2H, J=6.4, 12.8 Hz).

Reference Example 4-4

3-(2,4-dichlorophenyl)-1-[3,3-dimethoxycyclobutylmethyl]-4-trifluoromethyl-3-hydroxy-6-iodo-1,3-dihydro-2H-indol-2-one

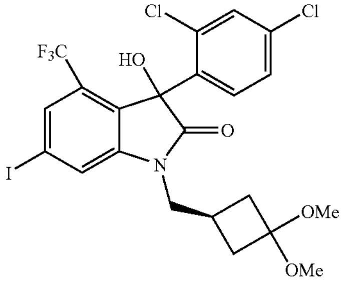

The compound of Reference example 4-3 (244 mg, 1.67 mmol) was used in a similar manner to Example 1-5 to give the titled compound (549 mg, 70%).

$^1$H NMR ($CDCl_3$, 400 MHz) δ 8.00 (d, 1H, J=8.4 Hz), 7.62 (s, 1H), 7.47 (s, 1H), 7.40 (dd, 1H, J=2.0, 8.4 Hz), 7.27 (d, 1H, J=2.0 Hz), 3.92 (dd, 1H, J=7.4, 14.3 Hz), 3.86 (dd, 1H, J=6.8, 14.3 Hz), 3.14 (s, 3H), 3.12 (s, 3H), 2.61-2.52 (s, 1H), 2.37-2.28 (m, 2H), 2.10-1.95 (m, 2H).

Reference Example 4-5

3(2,4-dichlorophenyl)-1-[3-oxocyclobutylmethyl]-4-trifluoromethyl-3-hydroxy-6-iodo-1,3-dihydro-2H-indol-2-one

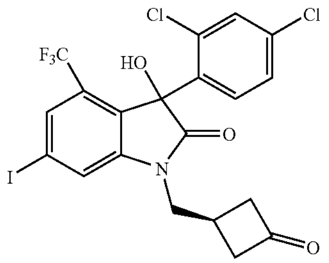

To a solution of the compound of Reference example 4-4 (308 mg, 0.5 mmol) in acetone (10 mL) were added water (30 μL) and pyridinium p-toluenesulfonate (12.6 mg, 0.05 mmol), and the mixture was heated to reflux for 8 hours. The reaction solution was concentrated, and thereto was added water, and the mixture was extracted with ethyl acetate, and then dried over anhydrous magnesium sulfate, and filtered, and then the filtrate was evaporated. The residue was recrystallized (n-hexane-toluene-ethyl acetate) to give the titled compound (208 mg, 73%).

$^1$H NMR ($CDCl_3$, 400 MHz) δ 8.01 (d, 1H, J=8.6 Hz), 7.69 (s, 1H), 7.54 (s, 1H), 7.44 (dd, 1H, J=2.1, 8.6 Hz), 7.30 (d, 1H, J=2.1 Hz), 4.10 (dd, 1H, J=7.9, 14.5 Hz), 3.99 (dd, 1H, J=6.8, 14.5 Hz), 3.32-2.92 (m, 6H).

Reference Example 5

(trans-3-diethylaminocyclobutyl)-methanol

Reference Example 5-1 cis-3-methanesulfonyloxycyclobutane Carboxylic Benzyl Ester

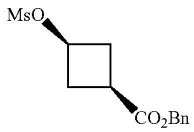

To a solution of cis-3-hydroxycyclobutane carboxylic benzyl ester (see WO03000657A1)(18.0 g, 87.5 mmol) in dichloromethane (155 m/L) was added triethylamine (18.3 mL, 131 mmol), and then thereto was added dropwise a solution of methanesulfonyl chloride (8.16 mL, 105 mmol) in dichloromethane (20 mL) at 0° C. for 15 minutes. The mixture was stirred for 1 hour, and then the reaction solution was washed with aqueous saturated sodium bicarbonate solution, dried over anhydrous magnesium sulfate, filtered, and concentrated to give the titled compound (24.9 g, quant.).

$^1$H NMR ($CDCl_3$, 400 MHz) δ 7.43-7.29 (m, 5H), 5.15 (s, 2H), 4.98-4.88 (m, 1H), 2.99 (s, 3H), 2.85-2.67 (m, 3H), 2.66-2.52 (m, 2H).

Reference Example 5-2 trans-3-diethylaminocyclobutane Carboxylic Benzyl Ester

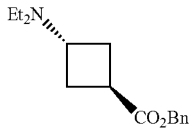

To a solution of the compound of Reference example 5-1 (20.34 g, 71.5 mmol) in N,N-dimethylformamide (72 mL) was added sodium azide (6.98 g, 107 mmol), and the mixture was heated to reflux at 120° C. for 8 hours. The reaction solution was cooled to room temperature, and then thereto was added ethyl acetate, and the mixture was washed with water twice. The organic layer was dried over anhydrous magnesium sulfate, filtered, and then concentrated.

The residue was dissolved in 2-propanol (100 mL), and thereto were added acetic acid (10 mL) and 5% rhodium-carbon (6.61 g), and the mixture was stirred at room temperature for 32 hours under normal pressure of hydrogen. The reaction solution was filtered and concentrated, and then thereto was added ethyl acetate, and the mixture was washed with 50% potassium carbonate. The organic layer was dried over anhydrous potassium carbonate, and filtered, and then the filtrate was evaporated.

The residue was dissolved in dichloromethane (143 mL), and thereto were successively added acetaldehyde (12.0 mL, 215 mmol) and sodium triacetoxyborohydride (33.3 g, 157 mmol). The mixture was stirred at room temperature for 4 hours, and thereto was added 1M hydrochloric acid. To the reaction solution was added anhydrous potassium carbonate, and then the mixture was extracted with chloroform. The organic layer was dried over anhydrous potassium carbonate, and filtered, and then the filtrate was evaporated and purified by silica gel column chromatography (chloroform methanol=1/0 to 10/1) to give the titled compound (8.58 g, 46%).

$^1$H NMR ($CDCl_3$, 400 MHz) δ 7.40-7.29 (m, 5H), 5.15 (s, 2H), 3.42-3.32 (m, 1H), 3.04-2.96 (m, 1H), 2.50 (q, 4H, J=7.2 Hz), 2.40-2.32 (m, 2H), 2.26-2.15 (m, 2H), 0.97 (t, 6H, J=7.2 Hz).

Reference Example 5-3

(trans-3-diethylaminocyclobutyl)-methanol

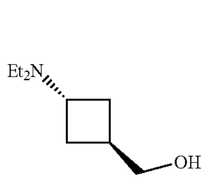

To a solution of lithium aluminum hydride (1.25 g, 32.8 mmol) in tetrahydrofuran (124 mL) was added the compound of Reference example 5-2 (8.58 g, 32.8 mmol) at 0° C., and the mixture was stirred for 1 hour. To the reaction solution were successively added water (1.25 mL), 4M aqueous sodium hydroxide solution (1.25 mL) and water (3.75 mL), and the mixture was filtered through celite. The filtrate was concentrated and purified by silica gel column chromatography (chloroform/methanol/ammonia water=20/1/0 to 10/1/0 to 100/10/1 to 100/20/1) to give the titled compound (3.41 g, 66%).

$^1$H NMR ($CDCl_3$, 400 MHz) δ 3.69 (d, 2H, J=7.4 Hz), 3.22-3.12 (m, 1H), 2.50 (q, 4H, J=7.2 Hz), 2.35-2.25 (m, 1H), 2.11-2.01 (m, 2H), 1.93-1.85 (m, 2H), 0.97 (t, 6H, J=7.4 Hz).

Reference Example 6

(trans-3-(1-pyrrolidinyl)-cyclobutyl)-methanol

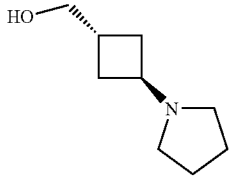

The titled compound was synthesized in a similar manner to Reference example 5.

$^1$H NMR ($CDCl_3$, 400 MHz) δ 3.69 (d, 2H, J=7.2 Hz), 2.97-2.89 (m, 1H), 2.47-2.40 (m, 5H), 2.18-1.98 (m, 2H), 2.05-1.87 (m, 2H), 1.82-1.76 (m, 4H).

Reference Example 7

(trans-3-ethylmethylaminocyclobutyl-methanol

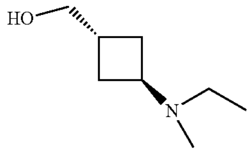

Reference Example 7-1

Synthesis of 3-benzoyloxymethyl-2,2-dichlorocyclobutanone

To a suspension of benzoic acid allyl ester (100 g, 0.617 mol) and zinc (activated Zn) (161 g, 2.47 mol) in diethyl ether (1.23 L) was added dropwise a solution of trichloroacetyl chloride (223 g, 1.23 mol) and dimethoxyethane (110 g, 1.23 mol) in diethyl ether (1.23 L, 2 L/mol) over 40 minutes under nitrogen with vigorously stirring, and then the mixture was stirred at room temperature (internal temperature: 30° C.) for 29 hours. During the stirring, additional zinc (activated Zn) (respectively, 150 g (2.29 mol) and 100 g (1.53 mol)) was added at 7 and 24 hours after the beginning of the stirring. To the reaction mixture was added hexane (1 L), and the mixture was stirred for 10 minutes, and then the solid was removed by decantation and the supernatant was washed with water (1 L), aqueous saturated sodium bicarbonate solution (3×1 L) and saturated saline (500 mL), and dried over magnesium sulfate. The mixture was evaporated and the precipitated white solid was collected by filtration and washed with hexane (500 mL) to give the titled compound (62.5 g, 37%).

$^1$H NMR ($CDCl_3$, 400 MHz) δ 8.03 (dd, 2H, J=8, 1 Hz), 7.60 (ddd, 1H, J=8, 8, 1 Hz), 7.47 (dd, 2H, J=8, 1 Hz), 4.70 (dd, 1H, J=12, 7 Hz), 4.63 (dd, 1H, J=12, 7 Hz), 3.55 (dd, 1H, J=17, 10 Hz), 3.41 (m, 1H), 3.24 (dd, 1H, J=17, 10 Hz).

Reference Example 7-2

Synthesis of 3-benzoyloxymethylcyclobutanone

To a suspension of zinc (144 g, 2.2 mol), acetic acid (452 mL) and pyridine (66 mL) was added the compound of Reference example 7-1 (98.9 g, 362 mmol) over 40 minutes under nitrogen with stirring under an ice-cooled bath, and then the mixture was stirred at 40° C. for 3 hours. To the reaction mixture was added diethyl ether (1 L), and the mixture was filtered and washed with diethyl ether (1 L). The filtrate was neutralized by adding water (200 mL) and sodium bicarbonate, and then filtered and washed with diethyl ether (1 L), water (500 mL), 1N hydrochloric acid (2×500 mL) and saturated saline (200 mL), and dried over magnesium sulfate. The mixture was evaporated to give a yellow oil (108 g). The oil was washed with aqueous saturated sodium bicarbonate solution (1 L) and saturated saline in order to remove the remaining acetic acid from the oil, and dried over magnesium sulfate. The oil was evaporated to give the titled compound (73.76 g, 99%).

$^1$H NMR ($CDCl_3$, 400 MHz) δ 8.03 (dd, 2H, J=8, 1 Hz), 7.59 (ddd, 1H, J=8, 8, 1 Hz), 7.46 (dd, 2H, J=8, 1 Hz), 4.50 (d, 2H, J=6 Hz), 3.26 (m, 2H), 3.00 (m, 3H).

Reference Example 7-3

Synthesis of 3-benzoyloxymethyl-1-cyclobutanol

A suspension of sodium borohydride (6.82 g, 180 mmol) in methanol (300 mL) was cooled with dry ice-acetone bath under nitrogen, and thereto was added dropwise a solution of the compound of Reference example 7-2 (61.28 g, 300 mmol) in THF (300 mL) over 1 hour, and then the mixture was stirred for 4 hours. Additional sodium borohydride (680 mg, 18 mmol) was added 3 hours after the beginning of the stirring. To the reaction solution was added aqueous ammonium chloride (1 L), and the mixture was extracted with ethyl acetate (1 L, 500 mL), washed with saturated saline (200 mL), and dried over magnesium sulfate. The mixture was evaporated to give a yellow oil (70.13 g, cis:trans=8:1).

$^1$H NMR ($CDCl_3$, 400 MHz) δ 8.03 (d, 2H, J=8 Hz), 7.58 (dd, 1H, J=8, 8 Hz), 7.43 (dd, 2H, J=8 Hz), 4.30 (d, 2H, J=6 Hz), 4.22 (m, 1H), 2.50 (m, 2H), 2.22 (m, 1H), 1.81 (m, 2H).

Reference Example 7-4

Synthesis of 3-benzoyloxymethyl-1-methanesulfonyloxycyclobutane

To a solution of the compound of Reference example 7-3 (crude 70.13 g, <300 mmol) and triethylamine (63 mL, 450 mol) in dichloromethane (150 mL) was added dropwise a solution of methanesulfonyl chloride (43 g, 375 mmol) in dichloromethane (150 mL) over 30 minutes under nitrogen, and the mixture was stirred at room temperature for 4 hours and at 35° C. for 1 hour. During the reaction, additional methanesulfonyl chloride (6 mL) and triethylamine (6 mL) were added once every 3 hours. The reaction solution was poured into water (1 L), extracted with chloroform (2×1 L), washed with aqueous saturated sodium bicarbonate solution (2×700 mL), and dried over magnesium sulfate. The mixture was evaporated to give a brown oil (92.63 g).

$^1$H NMR ($CDCl_3$, 400 MHz) δ 8.03 (d, 2H, J=8 Hz), 7.58 (dd, 1H, J=8, 8 Hz), 7.43 (dd, 2H, J=8 Hz), 4.95 (m, 1H), 4.33 (d, 2H, J=6 Hz), 3.00 (s, 3H), 2.62 (m, 2H), 2.40 (m, 1H), 2.25 (m, 2H).

Reference Example 7-5

Synthesis of 3-benzoyloxymethyl-1-azidocyclobutane

A suspension of the compound of Reference example 7-4 (crude 92.63 g, <300 mmol) and sodium azide (30.2 g, 450 mmol) in DMF (200 mL) was stirred at 120° C. for 5 hours under nitrogen. To the reaction solution was added water (1 L), and the mixture was extracted with ethyl acetate/toluene (½, 1 L), washed with water (1 L), aqueous saturated sodium bicarbonate solution (500 mL) and saturated saline (300 mL), and dried over magnesium sulfate. The solvent was replaced with THF.

$^1$H NMR ($CDCl_3$, 400 MHz) δ 8.03 (d, 2H, J=8 Hz), 7.58 (dd, 1H, J=8, 8 Hz), 7.43 (dd, 2H, J=8 Hz), 4.35 (d, 2H, J=7 Hz, 4.08 (m, 1H), 2.79 (m, 1H), 2.30 (m, 4H).

Reference Example 7-6

Synthesis of trans-3-benzoyloxymethyl-1-aminocyclobutane Hydrochloride

To a solution of the compound of the above Reference example 7-5 in THF (300 mL) were added water (8.1 g 450 mmol) and triphenylphosphine (94.4 g, 360 mmol) under an ice-cooled bath, and the mixture was stirred at room temperature for 3 hours. The mixture was evaporated, and then thereto were added diethyl ether (1 L) and 1N hydrochloric acid (300 mL). The aqueous layer was washed with ethyl acetate (2×1 L) and poured into 50% aqueous sodium carbonate solution. The mixture was extracted with ethyl acetate (2×1 L), and dried over magnesium sulfate. The mixture was evaporated to give a mixture of a brown oil and white solid. The resulting mixture was filtered by using ethyl acetate and evaporated. To the resulting brown oil (50.31 g) were added acetonitrile (200 mL) and 4N hydrochloric acid/dioxane (60 mL), and the mixture was evaporated to give a brown solid. The solid was recrystallized from a mixture of acetonitrile (700 mL) and 2-propanol (30 mL) to give the titled compound (35.62 g, 4 Steps 49%, cis:trans=1:50).

$^1$H NMR (d-DMSO, 400 MHz) δ 8.38 (br, 1H), 7.98 (dd, 2H, J=8, 1 Hz), 7.58 (ddd, 1H, J=8, 8, 1 Hz), 7.53 (dd, 2H, J=8, 1 Hz), 4.33 (d, 2H, J=7 Hz), 3.80 (m, 1H), 2.79 (m, 1H), 2.30 (m, 2H), 2.18 (m, 2H)

Reference Example 7-7

Synthesis of trans-3-benzoyloxymethyl-1-acetylaminocyclobutane

To a solution of the compound of Reference example 7-6 (51.3 g, 212 mmol) in tetrahydrofuran (1 L) were added anhydrous acetic acid (22 mL, 233 mmol) and triethylamine (65 mL, 466 mmol), and the mixture was stirred at room temperature for 5 hours. To the reaction solution was added water, and the mixture was extracted with ethyl acetate, dried over anhydrous magnesium sulfate, and then filtered and concentrated to give a white solid (50.34 g).

Reference Example 7-8

Synthesis of (trans-3-ethylmethylaminocyclobutyl)-methanol

To a solution of the compound of Reference example 7-7 (247 mg, 1.00 mmol) in dimethylformamide (1 mL) were added sodium hydride (55%, 52 mg, 1.2 mmol) and iodomethane (0.07 mL, 1.2 mmol), and the mixture was stirred at room temperature for 1 day. To the reaction solution was added ethyl acetate, and the mixture was washed with saturated aqueous sodium bicarbonate. The mixture was dried over anhydrous magnesium sulfate, and then filtered and concentrated to give a colorless oil (215 mg).

To a solution of lithium aluminum hydride (68 mg, 1.65 mmol) in tetrahydrofuran (5 mL) was added a solution of the resulting oil (215 mg) in tetrahydrofuran (5 mL) at 60° C., and the mixture was heated to reflux for 3 hours. The reaction solution was cooled to room temperature, and then thereto were successively added water (0.03 mL), 4M aqueous sodium hydroxide solution (0.03 mL) and water (0.09 mL), and the mixture was filtered through celite and concentrated. Thereto was added 1N-hydrochloric acid (3 mL), and the mixture was washed with ethyl acetate (2×20 mL), and then thereto was added 50% aqueous potassium carbonate solution (1 mL), and the mixture was extracted with ethyl acetate to give the titled compound (69 mg).

$^1$H NMR ($CDCl_3$, 400 MHz) δ 3.69 (d, 2H, J=7.1 Hz), 2.94-2.85 (m, 1H), 2.35 (q, 2H, J=7.3 Hz), 2.13 (s, 3H), 2.15-2.05 (m, 2H), 1.95-1.90 (m, 2H), 1.04 (t, 3H, J=7.2 Hz).

Reference Example 8

(trans-3-ethyl-n-propylaminocyclobutyl)-methanol

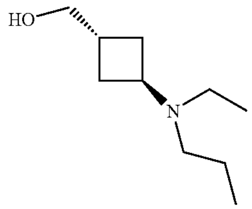

Reference Example 8-1

Synthesis of (trans-3-ethylaminocyclobutyl)-methanol

To a solution of lithium aluminum hydride (117 mg, 2.83 mmol) in tetrahydrofuran (11 mL) was added a solution of the compound of Reference example 7-7 (350 mg) in tetrahydrofuran (7 mL) at 60° C., and the mixture was heated to reflux for 6 hours. The reaction solution was cooled to room temperature, and then thereto were successively added water (0.1 mL), 4M aqueous sodium hydroxide solution (0.1 mL) and water (0.3 mL), and the mixture was filtered through celite and concentrated to give a 1:1 mixture of the titled compound and benzyl alcohol (314 mg).

$^1$H NMR ($CDCl_3$, 400 MHz) δ 3.67 (d, 2H, J=7.3 Hz), 3.40-3.32 (m, 1H), 2.56 (q, 2H, J=7.1 Hz), 2.44-2.33 (m, 1H), 2.10-2.02 (m, 2H), 1.90-1.82 (m, 2H), 1.09 (t, 3H, J=7.1 Hz).

Reference Example 8-2

Synthesis of (trans-3-ethyl-n-propylaminocyclobutyl)-methanol

To a solution of a mixture of the compound of Reference example 8-1 and benzyl alcohol (152 mg) in tetrahydrofuran (2.5 mL) were added propionyl chloride (51 mg, 0.55 mmol) and triethylamine (0.08 mL, 0.6 mmol), and the mixture was stirred at room temperature for 3 hours. To the reaction solution was added ethyl acetate, and the mixture was dried over anhydrous magnesium sulfate, and then filtered and concentrated to give a colorless oil.

To a solution of lithium aluminum hydride (41 mg, 1.0 mmol) in tetrahydrofuran (5 mL) was added a solution of the resulting oil in tetrahydrofuran (5 mL) at 60° C., and the mixture was heated to reflux for 3 hours. The reaction solution was cooled to room temperature, and then thereto were successively added water (0.03 mL), 4M aqueous sodium hydroxide solution (0.03 ml) and water (0.09 mL), and the mixture was filtered through celite and concentrated. Thereto was added 1N-hydrochloric acid (3 mL), and the mixture was washed with ethyl acetate (2×20 mL), and then thereto was added 50% aqueous potassium carbonate solution (1 mL), and the mixture was extracted with ethyl acetate to give the titled compound (42 mg).

$^1$H NMR($CDCl_3$, 400 MHz) δ 3.69 (d, 2H, J=7.1 Hz), 3.30-3.18 (m, 1H), 2.60 (br, 2H), 2.40-2.23 (m, 3H), 2.15 (br, 2H), 1.95-1.85 (m, 2H), 1.50-1.35 (m, 2H), 1.00 (t, 3H, J=7.0 Hz), 0.88 (t, 3H, J=7.2 Hz).

Reference Example 9

(trans-3-ethylcyclobutylmethylaminocyclobutyl)-methanol

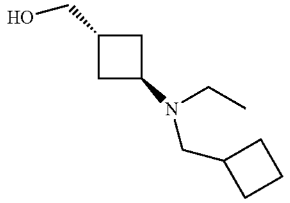

To a solution of the compound of Reference example 8-1 (130 mg, 0.55 mmol) in dimethylformamide (1.0 mL) were added cyclobutylmethyl bromide (98 mg, 0.66 mmol) and potassium carbonate (152 mg, 1.1 μmol), and the mixture was stirred at 100° C. for 3 hours. To the reaction solution was added chloroform, and the mixture was washed with water, and then dried over anhydrous magnesium sulfate, and then filtered and concentrated to give the titled compound (59 mg).

$^1$H NMR ($CDCl_3$, 400 MHz) δ 3.68 (d, 2H, J=7.1 Hz), 3.20-3.05 (m, 1H), 2.52-2.40 (m, 5H), 2.31-2.23 (m, 1H), 2.10-1.98 (m, 4H), 1.92-1.72 (m, 3H), 1.70-1.60 (m, 2H), 0.95 (t, 3H, J=7.2 Hz).

Reference Example 10

(trans-3-dicyclobutylmethylaminocyclobutyl)-methanol

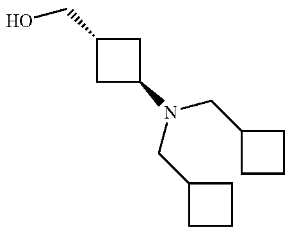

The titled compound was synthesized in a similar manner to Reference example 5.

$^1$H NMR ($CDCl_3$, 400 MHz) δ 3.66 (d, 2H, J=7.2 Hz), 3.19-3.11 (m, 1H), 2.52-2.38 (m, 6H), 2.33-2.23 (m, 1H), 2.08-1.98 (m, 6H), 1.92-1.83 (m, 4H), 1.82-1.72 (m, 2H), 1.68-58 (m, 4H).

Reference Example 11

(trans-3-cyclobutylmethylcyclopropylmethylmethylaminocyclobutyl)-methanol

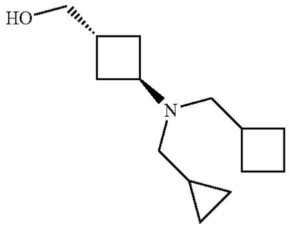

The titled compound was synthesized in a similar manner to Reference example 5.

$^1$H NMR ($CDCl_3$, 400 MHz) δ 3.68 (d, 2H, J=7.1 Hz), 3.33-3.21 (m, 1H), 2.64-2.48 (br, 2H), 2.40-2.22 (br, 2H), 2.12-1.98 (br, 3H), 1.97-1.75 (m, 4H), 1.75-1.50 (m, 5H), 0.90-0.78 (br, 1H), 0.57-0.43 (br, 2H) 0.15-0.01 (br, 2H).

Reference Example 12

(trans-3-ethyl-iso-butylaminocyclobutyl)-methanol

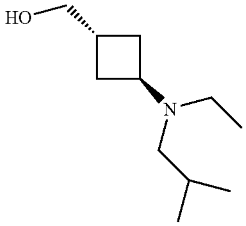

The titled compound was synthesized in a similar manner to Reference example 9.

$^1$H NMR ($CDCl_3$, 400 MHz) δ 3.68 (d, 2H, J=7.5 Hz), 3.22-3.15 (m, 1H), 2.51 (q, 2H, J=7.5 Hz), 2.32-2.21 (m, 1H), 2.10-1.96 (m, 4H), 1.89-1.82 (m, 2H), 1.75-1.65 (m, 1H), 0.93 (t, 3H, J=7.5 Hz), 0.88 (d, 6H, J=6.6 Hz).

Reference Example 13

(trans-3-cyclopropyl-(ethylamino)-cyclobutyl)-methanol

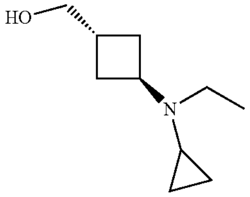

To a solution of the compound of Reference example 8-1 (220 mg, 0.93 mmol) in methanol (9.0 mL) were added acetic acid (558 mg, 9.3 mmol), (1-ethoxycyclopropoxy)-trimethylsilane (732 mg, 4.2 mmol) and sodium cyanoboronide (233 mg, 3.7 mmol), and the mixture was heated to reflux for 5 hours. To the reaction solution was added 1N-hydrochloric acid (10 mL), and washed with ethyl acetate (2×40 mL), and then thereto was added 50% aqueous potassium carbonate solution (5 mL), and the mixture was extracted with chloroform to give the titled compound (129 mg, 82%).

LC-MS m/z 170 (M+H+).

Reference Example 14

((trans-3-tert-butylamino)-cyclobutyl)-methanol

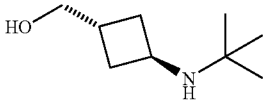

Reference Example 14-1

Synthesis of trans-1-benzoyloxymethyl-3-tert-butylaminocyclobutane

To a solution of the compound of Reference example 7-6 (170 mg, 0.83 mmol) in dimethylformamide (1 mL) were added 2-iodo-2-methylpropane (458 mg, 2.49 mmol) and potassium carbonate (458 mg, 3.32 mmol), and the mixture was stirred at 100° C. for 3 hours. To the reaction solution was added water, and the mixture was extracted with ethyl acetate, and the organic layer was dried over magnesium sulfate, filtered, and then evaporated and purified by silica gel column chromatography (chloroform/methanol 20/1 to 10/1) to give the titled compound (549 mg, 46%).

Reference Example 14-2

Synthesis of ((trans-3-tert-butylamino)-cyclobutyl)-methanol

To a solution of the compound of Reference example 14-1 (300 mg, 1.15 mmol) in tetrahydrofuran-methanol (2 mL-2 mL) was added 4N aqueous sodium hydroxide solution (0.43 mL, 1.72 mmol), and the mixture was stirred at 50° C. for 3 hours. Thereto was added 1N-hydrochloric acid (3 mL), and the mixture was washed with ethyl acetate (2×20 mL), and then thereto was added 50% aqueous potassium carbonate solution (1 mL), and the mixture was extracted with ethyl acetate. Thus, the titled compound was obtained (90 mg, 50%).

$^1$H NMR ($CDCl_3$, 400 MHz) δ 3.68 (d, 2H, J=7.5 Hz), 3.54-3.47 (m, 1H), 2.32-2.24 (m, 1H), 2.17-2.09 (m, 2H), 1.92-1.83 (m, 2H), 1.07 (s, 9H).

Reference Example 15

((trans-(3-tert-butyl)-methylamino)-cyclobutyl)-methanol

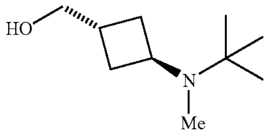

Reference Example 15-1

Synthesis of ((trans-(3-tert-butyl)-methylamino)-cyclobutyl)-methyl Benzoate

To a solution of the compound of Reference example 14-1 (100 mg, 0.38 mmol) in acetonitrile (3.8 mL) were added iodomethane (0.026 mL, 0.42 mmol) and potassium carbonate (79 mg, 0.57 mmol), and the mixture was stirred at room temperature for 3 hours. To the reaction solution was added water, and the mixture was extracted with ethyl acetate, dried over anhydrous magnesium sulfate, and then filtered and evaporated. The residue was purified by silica gel column chromatography (chloroform/methanol=20/1 to 10/1) to give the titled compound (78 mg, 75%).

Reference Example 15-2

Synthesis of ((trans-(3-tert-butyl)-methylamino)-cyclobutyl)-methanol

The titled compound was obtained in a similar manner to Reference example 14-2.

$^1$H NMR ($CDCl_3$, 400 MHz) δ 3.70 (d, 2H, J=7.5 Hz), 3.68-3.58 (m, 1H), 2.38-2.28 (m, 2H), 2.24 (s, 3H), 2.17-2.09 (m, 1H), 1.92-1.83 (m, 2H), 1.09 (s, 9H).

Reference Example 16

(trans-3-ethyl-(2,2-dimethylpropyl)-aminocyclobutyl)-methanol

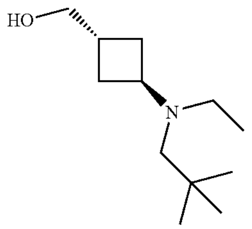

The titled compound was synthesized in a similar manner to Reference example 9.

LC-MS m/z 200 (M+H+).

Reference Example 17

(trans-3-ethyl-((1-methylcyclopropyl)-methyl)-aminocyclobutyl)-methanol

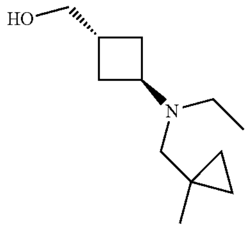

The titled compound was synthesized in a similar manner to Reference example 9.

$^1$H NMR ($CDCl_3$, 400 MHz) δ 3.52-3.44 (m, 2H), 3.25-3.17 (m, 1H), 2.68-2.60 (m, 2H), 2.32-2.21 (m, 1H), 2.08 (s, 2H), 2.12-2.01 (m, 2H), 1.89-1.81 (m, 2H), 1.07 (s, 3H), 0.91 (t, 3H, J=7.5 Hz), 0.30-0.24 (m, 4H).

Reference Example 18

1-(2-propynyl)-imidazolidin-2-one

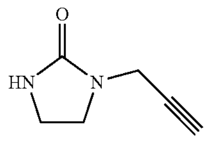

To a suspension of ethylene urea (592 mg, 6.88 mmol) in tetrahydrofuran (15 mL) was added dropwise butyl lithium/hexane solution (2.7 mL, 13.6 mmol) at 0° C. under nitrogen. Thereto was added 3-bromopropyne (410 mg, 6.88 mmol), and the mixture was stirred at 60° C. for 3 hours. Thereto was added 5% aqueous potassium bisulfate solution, and the mixture was extracted with ethyl acetate, dried over magnesium sulfate, and filtered. The filtrate was concentrated in vacuo and the residue was purified by silica gel chromatography (ethyl acetate/hexane 1/1) to give the titled compound (202 mg, 24%).

$^1$H NMR ($CDCl_3$, 400 MHz) δ4.74 (bs, 1H), 4.02 (d, 2H, J=2.4 Hz), 3.41-3.57 (m, 4H), 2.24 (t, 1H, J=2.4 Hz).

Example 1

3-(2,4-dichlorophenyl)-1-[trans-3-(diethylamino)-cyclobutylmethyl]-4-trifluoromethyl-3-hydroxy-2-oxoindoline-6-carboxamide Hydrochloride Example 1-1

1-[trans-3-(diethylamino)-cyclobutylmethyl]-4-trifluoromethyl-6-iodo-1H-indole-2,3-dione

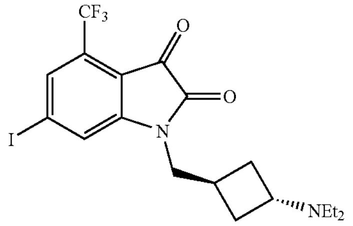

To a solution of the compound of Reference example 5 (2.62 g, 16.6 mmol) in dichloromethane (28 mL) was added triethylamine (3.48 mL, 25.0 mmol) and added dropwise a solution of methanesulfonyl chloride (1.55 mL, 20.0 mmol) in dichloromethane (5 mL) at 0° C. The mixture was stirred at 0° C. for 1 hour, and then to the reaction solution was added saturated aqueous sodium bicarbonate, and the mixture was extracted with chloroform. The organic layer was dried over magnesium sulfate and filtered, and then evaporated to give a crude mesylate.

To a solution of 60% sodium hydride (733 mg, 18.3 mmol) in N,N-dimethylformamide (28 mL) were added 4-trifluoromethyl-6-iodo-1H-indole-2,3-dione (6.25 g, 18.3 mmol) and the crude mesylate, and the mixture was stirred at 100° C. for 3 hours. The mixture was cooled to room temperature, and to the reaction solution was added saturated aqueous sodium bicarbonate, and the mixture was extracted with ethyl acetate-toluene (1:1). The organic layer was dried over magnesium sulfate and filtered, and then evaporated and purified by silica gel column chromatography (chloroform/methanol/triethylamine=100/1/0 to 20/1/0 to 5/1/0 to 250/50/1) to give the titled compound (3.13 g, 39%).

$^1$H NMR ($CDCl_3$, 400 MHz) δ 7.75 (s, 1H), 7.49 (s, 1H), 3.88 (d, 2H, J=8.4 Hz), 3.46-3.36 (m, 1H), 2.61-2.47 (m, 1H), 2.52 (q, 4H, J=7.1 Hz), 2.18-2.05 (m, 2H), 2.00-1.90 (m, 2H), 0.99 (t, 6H, J=7.1 Hz).

Example 1-2

3-(2,4-dichlorophenyl)-1-[trans-3-(diethylamino)cyclobutylmethyl]-4-trifluoromethyl-3-hydroxy-6-iodo-1,3-dihydro-2H-indol-2-one

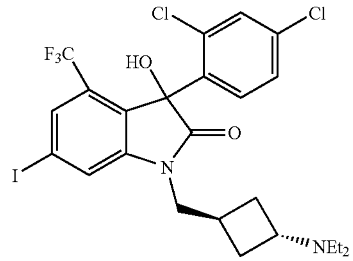

To a solution of the compound of Example 1-1 (3.13 g, 6.52 mmol) in tetrahydrofuran (65 mL) was added dropwise a solution of 2,4-dichlorophenylmagnesium iodide (9.78 mmol) in ether (19.6 mL) at −78° C. The mixture was stirred for 1 hour, and to the reaction solution was added saturated aqueous sodium bicarbonate, and the mixture was extracted with ethyl acetate. The organic layer was dried over anhydrous magnesium sulfate and filtered, and then evaporated. The residue was purified by silica gel column chromatography (chloroform/methanol=1/0 to 20/1 to 10/1 to 5/1) to give the titled compound (2.95 g, 86%).

$^1$H NMR ($CDCl_3$, 400 MHz) δ 8.00 (d, 1H, J=8.6 Hz), 7.74 (s, 1H), 7.41 (s, 1H), 7.39 (dd, 1H, J=2.1, 8.6 Hz), 7.27 (d, 1H, J=2.1 Hz), 3.94 (dd, 1H, J=8.6, 14.3 Hz), 3.84 (dd, 1H, J=8.0, 14.3 Hz), 3.48-3.34 (m, 1H), 2.80-2.57 (m, 1H), 2.53 (q, 4H, J=7.2 Hz), 2.23-2.07 (m, 2H), 2.07-1.74 (m, 2H), 0.99 (t, 6H, J=7.2 Hz).

Example 1-3

3-(2,4-dichlorophenyl)-1-[trans-3-(diethylamino)-cyclobutylmethyl]-4-trifluoromethyl-3-hydroxy-6-cyano-1,3-dihydro-2H-indol-2-one

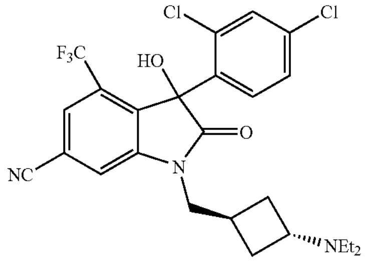

To a solution of the compound of Example 1-2 (68 mg, 0.11 mmol) in N,N-dimethylformamide (1.1 mL) were added zinc cyanide (15 mg, 0.13 mmol) and tetrakistriphenylphosphine palladium (25 mg, 0.02 mmol), and the reaction was carried out at 80° C. for 2 hours. To the reaction solution was added saturated aqueous sodium bicarbonate, and the mixture was extracted with toluene-ethyl acetate (1:1). The organic layer was dried over magnesium sulfate and filtered, and then evaporated and purified by silica gel column chromatography (chloroform/methanol/ammonia water=50/1/0 to 10/1/0 to 100/10/1) to give the titled compound (54 mg, 94%).

$^1$H NMR ($CDCl_3$, 400 MHz) δ 8.00 (d, 1H, J=8.6 Hz), 7.59 (s, 1H), 7.43 (dd, 1H, J=2.1, 8.6 Hz), 7.31 (s, 1H), 7.29 (d, 1H, J=2.1 Hz), 4.01 (dd, 1H, J=8.7, 14.3 Hz), 3.88 (dd, 1H, J=7.7, 14.3 Hz), 3.46-3.34 (m, 1H), 2.69-2.55 (m, 1H), 2.50 (q, 4H, J=7.2 Hz), 2.18-1.90 (m, 4H), 0.97 (t, 6H, J=7.2 Hz).

Example 1-4

3-(2,4-dichlorophenyl)-1-[trans-3-(diethylamino)-cyclobutylmethyl]-4-trifluoromethyl-3-hydroxy-2-oxoindoline-6-carboxamide hydrochloride

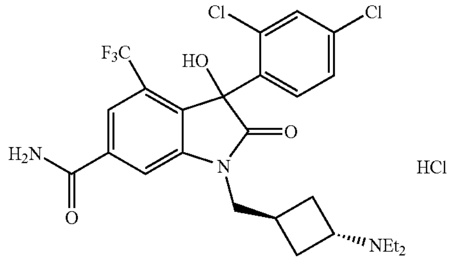

To a solution of the compound of Example 1-3 (1.76 g, 3.34 mmol) in tert-butyl alcohol (34 mL) was added potassium hydroxide (1.76 g, 31.4 mmol), and the mixture was stirred at 50° C. for 1.5 hours. To the reaction solution were added ethyl acetate (100 mL) and water (2 mL), and then the mixture was dried over magnesium sulfate and filtered. The mixture was evaporated, and then dissolved in ethyl acetate again and filtered. The filtrate was evaporated, and then thereto were added tetrahydrofuran (100 mL) and 1M hydrochloric acid (5 mL), and the mixture was evaporated, and then the residual water was removed by azeotropic distillation with toluene. The resulting solid was washed with diethyl ether, and then dried to give the titled compound (1.89 g, 97%).

$^1$H NMR (DMSO-$d_6$, 400 MHz) δ 10.76 (brs, 1H), 8.43 (s, 1H), 8.08 (d, 1H, J=8.7 Hz), 8.04 (s, 1H), 7.82 (s, 1H), 7.76 (s, 1H), 7.59 (dd, 1H, J=2.2, 8.7 Hz), 7.51 (d, 1H, J=2.2 Hz), 7.46 (s, 1H), 4.25-4.10 (m, 1H), 4.10-3.95 (m, 2H), 3.13-2.98 (m, 2H), 2.98-2.86 (m, 2H), 2.78-2.65 (m, 1H), 2.64-2.46 (m, 2H), 2.21-2.00 (m, 2H), 1.17 (t, 3H, J=7.2 Hz), 1.17 (t, 3H, J=7.2 Hz).

Example 2

3-(2,4-dichlorophenyl)-1-[(trans-3-(diethylamino)-cyclobutylmethyl]-4-trifluoromethyl-3-hydroxy-2-oxoindoline-6-carboxamide Hydrochloride Example 2-1

3-(2-chlorophenyl)-1-[trans-3-(diethylamino)-cyclobutylmethyl]-4-trifluoromethyl-3-hydroxy-6-iodo-1,3-dihydro-2H-indol-2-one

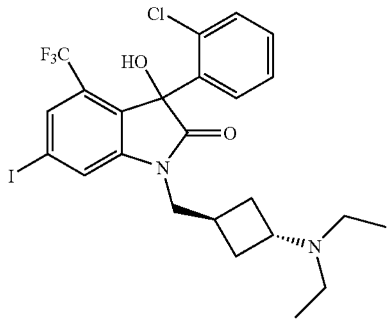

2-chlorophenylmagnesium bromide (0.35 mmol) and the compound of Example 1-1 were reacted in a similar manner to Example 1-2 to give the titled compound (50.4 mg, 74%).

$^1$H NMR ($CDCl_3$, 400 MHz) δ 8.05 (d, 1H, J=7.8 Hz), 7.61 (s, 1H), 7.42 (dd, 1H, J=7.6, 7.8 Hz), 7.41 (s, 1H), 7.32 (dd, 1H, J=7.6, 7.6 Hz), 7.25 (d, 1H, J=7.6 Hz), 3.97 (dd, 1H, J=8.6, 14.2 Hz), 3.86 (dd, 1H, J=7.8, 14.2 Hz), 3.48-3.32 (m, 1H), 2.72-2.58 (m, 1H), 2.53 (q, 4H, J=7.0 Hz, 2.22-1.92 (m, 4H), 0.98 (t, 6H, J=7.0 Hz).

Example 2-2

3-(2-chlorophenyl)-1-[trans-3-(diethylamino)-cyclobutylmethyl]-4-trifluoromethyl-3-hydroxy-6-cyano-1,3-dihydro-2H-indol-2-one

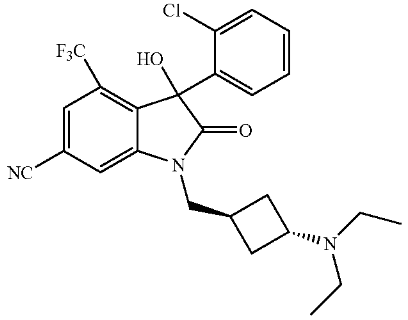

The compound of Example 2-1 (50.4 mg, 0.09 mmol) was used in a similar manner to Example 1-3 to give the titled compound (27.5 mg, 66%).

$^1$H NMR ($CDCl_3$, 400 MHz) δ 8.05 (dd, 1H, J=1.4, 7.7 Hz), 7.58 (s, 1H), 7.45 (ddd, 1H, J=1.4, 7.7, 7.7 Hz), 7.35 (ddd, 1H, J=1.4, 7.7, 7.7 Hz), 7.31 (s, 1H), 7.26 (dd, 1H, J=1.4, 7.7 Hz), 4.02 (dd, 1H, J=8.7, 14.3 Hz), 3.90 (dd, 1H, J=7.7, 14.3 Hz), 3.48-3.36 (m, 1H), 2.72-2.57 (m, 1H), 2.52 (q, 4H, J=7.2 Hz), 2.22-1.92 (m, 4H), 0.98 (t, 6H, J=7.2 Hz).

Example 2-3

3-(2-chlorophenyl)-1-[trans-3-(diethylamino)-cyclobutylmethyl]-4-trifluoromethyl-3-hydroxy-2-oxoindoline-6-carboxamide Hydrochloride

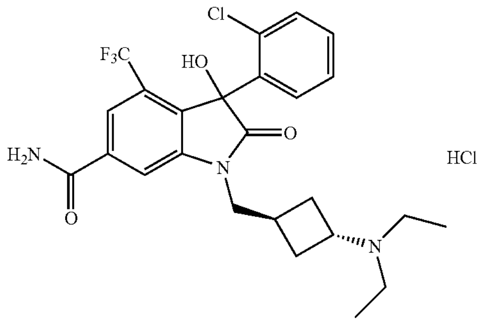

The compound of Example 2-2 (27.5 mg, 0.06 mmol) was used in a similar manner to Example 1-4 to give the titled compound (25.2 mg, 83%).

$^1$H NMR (DMSO-$d_6$, 400 MHz) δ 10.16 (brs, 1H), 8.36 (s, 1H), 8.08 (dd, 1H, J=1.4, 7.6 Hz), 7.96 (s, 1H), 7.81 (s, 1H), 7.77 (s, 1H), 7.48 (ddd, 1H, J=1.4, 7.6, 7.6 Hz), 7.37 (ddd, 1H, J=1.4, 7.6, 7.6 Hz), 7.32 (s, 1H), 7.30 (dd, 1H, J=1.4, 7.6 Hz), 4.20-4.10 (m, 1H), 4.06 (dd, 1H, J=8.6, 14.3 Hz), 3.98 (dd, 1H, J=7.3, 14.3 Hz), 3.15-2.97 (m, 4H), 2.78-2.64 (m, 1H), 2.55-2.39 (m, 2H), 2.20-2.05 (m, 2H), 1.16 (t, 3H, J=7.2 Hz), 1.16 (t, 3H, J=7.2 Hz).

Example 3

3-(2,4-dichlorophenyl)-1-[trans-3-(diethylaminomethyl)-cyclobutyl]-4-trifluoromethyl-3-hydroxy-2-oxoindoline-6-carboxamide Hydrochloride Example 3-1

N,N-diethyl-cis-3-hydroxycyclobutane carboxamide

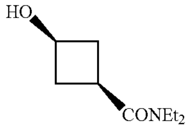

To a solution of aluminum trichloride (533 mg, 4 mmol) in dichloromethane (4 mL) were added diethylamine (1.67 mL, 16 mmol) and benzyl cis-3-hydroxycyclobutane carboxylate (413 mg, 2.0 mmol) at 0° C., and then the mixture was stirred at room temperature for 24 hours. To the reaction solution was added saturated aqueous sodium bicarbonate, and the mixture was filtered through celite, and then extracted with ethyl acetate, dried over magnesium sulfate and filtered. The filtrate was evaporated and purified by silica gel column chromatography (n-hexane/ethyl acetate=3/1 to 0/1, ethyl acetate/methanol=9/1) to give the titled compound (321 mg, 94%).

$^1$H NMR ($CDCl_3$, 400 MHz) δ 4.22-4.11 (m, 1H), 3.36 (q, 2H, J=7.1 Hz), 3.25 (q, 2H, J=7.1 Hz), 3.06 (brs, 1H), 2.81-2.72 (m, 1H), 2.59-2.51 (m, 2H), 2.26-2.18 (m, 2H), 1.14 (t, 3H, J=7.1 Hz), 1.10 (t, 3H, J=7.1 Hz).

Example 3-2

(cis-3-hydroxycyclobutylmethyl)-diethylamine

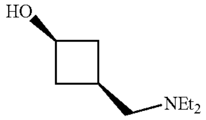

To a solution of lithium aluminum hydride (78.4 mg, 2.07 mmol) in tetrahydrofuran (3.8 mL) was added the compound of Example 3-1 (322 mg, 1.88 mmol), and the mixture was heated to reflux for 3 hours. To the reaction solution were successively added water (79 μL), 4M aqueous sodium hydroxide solution (79 μL) and water (237 μL) at room temperature, and the mixture was filtered through celite. The filtrate was concentrated to give the titled compound (282 mg, 96%).

$^1$H NMR ($CDCl_3$, 400 MHz) δ 4.16-4.08 (m, 1H), 2.49 (q, 4H, J=7.2 Hz), 2.49-2.42 (m, 3H), 2.25-2.05 (m, 1H), 1.98-1.89 (m, 1H), 1.80-1.65 (m, 1H), 1.59-1.51 (m, 2H), 1.00 (t, 6H, J=7.2 Hz).

Example 3-3

3-(2,4-dichlorophenyl)-1-[trans-3-(diethylaminomethyl)-cyclobutyl]-4-trifluoromethyl-3-hydroxy-6-iodo-1,3-dihydro-2H-indol-2-one

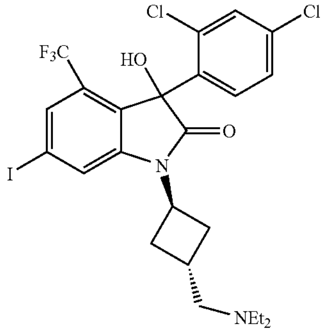

To a solution of the compound of Example 3-2 (86.5 mg, 0.55 mmol) in tetrahydrofuran (2.5 mL) were added triphenylphosphine (262 mg, 1 mmol), diisopropyl azodicarboxylate (202 mg, 1 mmol) and the compound of Reference example 1-4 (301 mg, 0.5 mmol), and the mixture was stirred at room temperature for 24 hours. The reaction solution was concentrated and purified by silica gel column chromatography (chloroform/methanol=40/1 to 20/1). The purified substance was dissolved in tetrahydrofuran (3.1 mL), and thereto was added tetra-n-butylammonium fluoride (97 mg, 0.37 mmol) at room temperature, and the mixture was stirred for 2 hours. The reaction solution was concentrated and purified by silica gel column (chloroform/methanol/ammonia water=20/1/0 to 5/1/0 to 100/20/1) to give the titled compound (76 mg, 24%).

$^1$H NMR ($CDCl_3$, 400 MHz) δ 7.98 (d, 1H, J=8.5 Hz), 7.62 (s, 1H), 7.54 (s, 1H), 7.38 (d, 1H, J=8.5 Hz), 7.26 (s, 1H), 4.68-4.78 (m, 1H), 3.02-2.87 (m, 2H), 2.70-2.56 (m, 3H), 2.56 (q, 4H, J=7.1 Hz), 2.30-2.17 (m, 2H), 1.04 (t, 6H, J=7.1 Hz).

Example 3-4

3-(2,4-dichlorophenyl)-1-[trans-3-(diethylaminomethyl)-cyclobutyl]-4-trifluoromethyl-3-hydroxy-6-cyano-1,3-dihydro-2H-indol-2-one

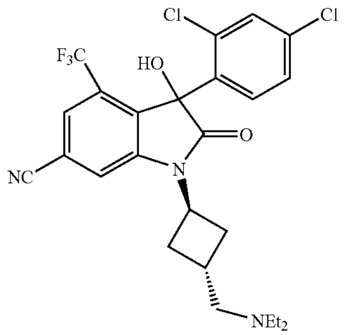

The compound of Example 3-3 (68 mg, 0.11 mmol) was used in a similar manner to Example 1-3 to give the titled compound (54 mg, 94%).

$^1$H NMR ($CDCl_3$, 400 MHz) δ 7.99 (d, 1H, J=8.9 Hz), 7.59 (d, 1H, J=0.4 Hz), 7.44 (d, 1H, J=0.4 Hz), 7.41 (dd, 1H, J=2.0, 8.6 Hz), 7.28 (d, 1H, J=2.0 Hz), 4.83-4.74 (m, 1H), 3.01-2.86 (m, 2H), 2.74-2.60 (m, 3H), 2.57 (q, 4H, J=7.1 Hz), 2.32-2.21 (m, 2H), 1.04 (t, 6H, J=7.1 Hz).

Example 3-5

3-(2,4-dichlorophenyl)-1-[trans-3-(diethylaminomethyl)-cyclobutyl]-4-trifluoromethyl-3-hydroxy-2-oxoindoline-6-carboxamide hydrochloride

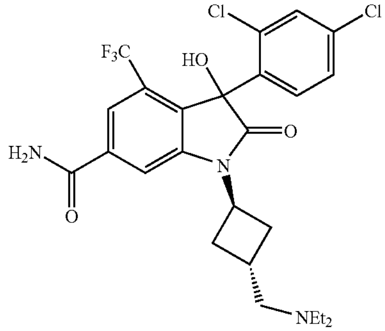

HCl

The compound of Example 3-4 (54 mg, 0.10 mmol) was used in a similar manner to Example 1-4 to give the titled compound (55 mg, 92%).

$^1$H NMR (DMSO-$d_6$, 400 MHz) δ 9.82 (brs, 1H), 8.40 (s, 1H), 8.06 (d, 1H, J=8.6 Hz), 8.05 (s, 1H), 7.82 (s, 1H), 7.74 (s, 1H), 7.58 (dd, 1H, J=2.1, 8.6 Hz), 7.49 (d, 1H, J=2.1 Hz), 7.45 (s, 1H), 5.12-5.00 (m, 1H), 3.45-2.92 (m, 8H), 2.88-2.77 (m, 1H), 2.40-2.29 (m, 2H), 1.24 (t, 6H, J=7.2 Hz).

Example 4

3-(2,4-dichlorophenyl)-1-[cis-3-(dicyclopropylamino) cyclobutylmethyl]-4-trifluoromethyl-3-hydroxy-2-oxoindoline-6-carboxamide Hydrochloride Example 4-1

N-cyclopropylmethylcyclopropanecarboxamide

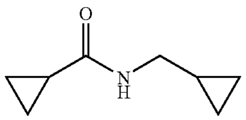

To a solution of cyclopropane carboxylic acid (1.72 g, 20 mmol) and cyclopropylmethylamine (1.42 g, 20 mmol) in N,N-dimethylformamide (20 mL) were added 1-(3-dimethylaminopropyl)-3-ethylcarbodiimide hydrochloride (4.22 g, 22 mmol) and 1-hydroxybenzotriazole (4.05 mmol, 30 mmol), and the mixture was stirred at room temperature for 20 hours. To the reaction solution was added ethyl acetate, and the mixture was washed with 1M hydrochloric acid and saturated aqueous sodium bicarbonate. The organic layer was dried over anhydrous magnesium sulfate, and then filtered and concentrated. The resulting residue was recrystallized (diethyl ether-n-hexane) to give the titled compound (1.16 g, 42%).

$^1$H NMR ($CDCl_3$, 400 MHz) δ 5.74 (brs, 1H), 3.13 (dd, 2H, J=5.6, 7.2 Hz), 1.37-0.98 (m, 1H), 0.99-0.93 (m, 3H), 0.76-0.69 (m, 2H), 0.53-0.48 (m, 2H), 0.22-0.18 (m, 2H).

Example 4-2

Dicyclopropylmethylamine

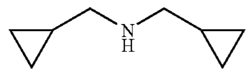

To a solution of lithium aluminum hydride (209 mg, 5.5 mmol) in tetrahydrofuran (3 mL) was added the compound of Example 4-1 (696 mg, 5 mmol) in tetrahydrofuran (2 mL) at 0° C. The reaction solution was heated to reflux for 5 hours, and then allowed to cool to room temperature, and thereto were successively added water (0.21 mL), 4M aqueous sodium hydroxide solution (0.21 mL) and water (0.63 ml). The suspension was filtered through celite, and then concentrated to give the titled compound (361 mg, 58%).

$^1$H NMR ($CDCl_3$, 400 MHz) δ 2.47 (d, 4H, J=6.9 Hz), 6.0 (brs, 1H), 1.02-0.90 (m, 2H), 0.49-0.44 (m, 4H), 0.12-0.08 (m, 4H).

Example 4-3

3-(2,4-dichlorophenyl)-1-[cis-3-(dicyclopropylamino)-cyclobutylmethyl]-4-trifluoromethyl-3-hydroxy-6-iodo-1,3-dihydro-2H-indol-2-one, 3-(2,4-dichlorophenyl)-1-[trans-3-(dicyclopropylamino)-cyclobutylmethyl]-4-trifluoromethyl-3-hydroxy-6-iodo-1,3-dihydro-2H-indol-2-one

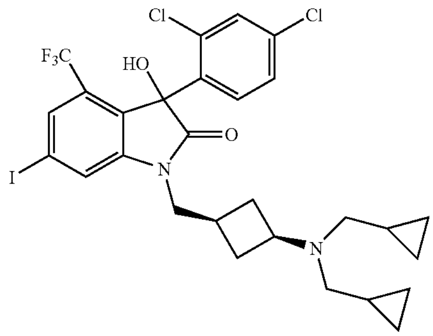

-continued

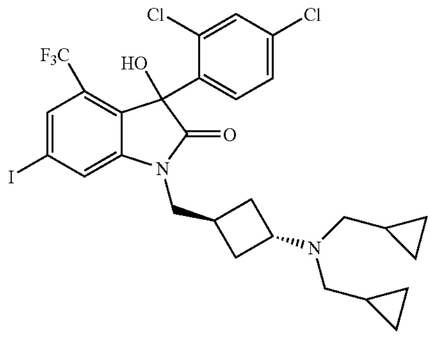

To a solution of the compound of Reference example 4-5 (50 mg, 0.09 mmol) in dichloromethane were successively added dicyclopropylmethylamine (16.5 mg, 0.13 mmol) and sodium triacetoxyborohydride (22.4 mg, 0.11 mmol), and the mixture was stirred at room temperature for 6.5 hours. To the reaction solution was added 1M hydrochloric acid, and then added anhydrous potassium carbonate, and the mixture was extracted with ethyl acetate. The organic layer was dried over anhydrous potassium carbonate and filtered, and then concentrated and purified by silica gel column chromatography (chloroform/methanol=50/1 to 20/1) to give the titled compound (cis: 29 mg, 48%, trans: 15 mg, 26%).

Example 4-4

3-(2,4-dichlorophenyl)-1-[cis-3-(dicyclopropylamino)-cyclobutylmethyl]-4-trifluoromethyl-3-hydroxy-6-cyano-1,3-dihydro-2H-indol-2-one

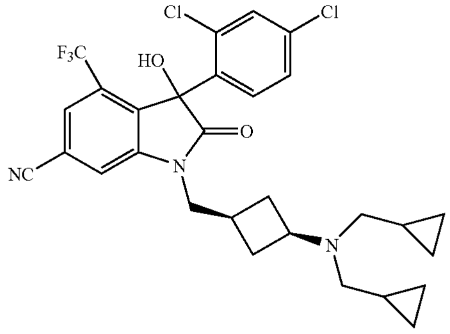

3-(2,4-dichlorophenyl)-1-[cis-3-(dicyclopropylamino)-cyclobutylmethyl]-4-trifluoromethyl-3-hydroxy-6-iodo-1,3-dihydro-2H-indol-2-one (64 mg, 0.09 mmol) was used in a similar manner to Example 1-3 to give the titled compound (51 mg, 94%).

$^1$H NMR($CDCl_3$, 400 MHz) δ 8.14 (d, 1H, J=8.4 Hz), 7.56 (d, 1H, J=0.8 Hz), 7.41 (dd, 1H, J=2.0, 8.4 Hz), 7.25 (d, 1H, J=2.0 Hz), 7.21 (d, 1H, J=0.8 Hz), 4.12 (dd, 1H, J=3.6, 14.8 Hz), 3.54 (dd, 1H, J=4.0, 14.8 Hz), 3.11-3.01 (m, 1H), 2.52-2.40 (m, 2H), 2.32 (d, 4H, J=5.6 Hz), 2.30-2.17 (m, 2H), 1.85-1.75 (m, 1H), 1.70-1.59 (m, 1H), 0.81-0.72 (m, 2H), 0.51-0.42 (m, 4H), 0.10-0.00 (m, 4H).

Example 4-5

3-(2,4-dichlorophenyl)-1-[cis-3-(dicyclopropylamino)-cyclobutylmethyl]-4-trifluoromethyl-3-hydroxy-2-oxoindoline-6-carboxamide Hydrochloride

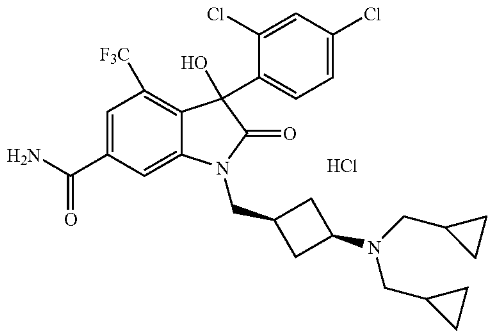

The compound of Example 4-4 (51 mg, 0.09 mmol) was used in a similar manner to Example 1-4 to give the titled compound (56 mg, 49%).

$^1$H NMR (DMSO-$d_6$, 400 MHz) δ 9.94 (brs, 1H), 8.40 (s, 1H), 8.09 (s, 1H), 8.07 (d, 1H, J=8.7 Hz), 7.83 (s, 1H), 7.78 (s, 1H), 7.58 (dd, 1H, J=2.2, 8.7 HZ), 7.49 (d, 1H, J=2.2 Hz), 7.44 (s, 1H), 4.00-3.85 (m, 2H), 3.82-3.68 (m, 1H), 3.05-2.97 (m, 4H), 2.58-2.45 (m, 1H), 2.44-2.23 (m, 4H), 1.12-1.00 (m, 2H), 0.70-0.52 (m, 4H), 0.48-0.32 (m, 4H).

Example 5

3-(2,4-dichlorophenyl)-1-[trans-3-(dicyclopropylamino)-cyclobutylmethyl]-4-trifluoromethyl-3-hydroxy-2-oxoindoline-6-carboxamide Hydrochloride Example 5-1

3-(2,4-dichlorophenyl)-1-[trans-3-(dicyclopropylamino)-cyclobutylmethyl]-4-trifluoromethyl-3-hydroxy-6-cyano-1,3-dihydro-2H-indol-2-one

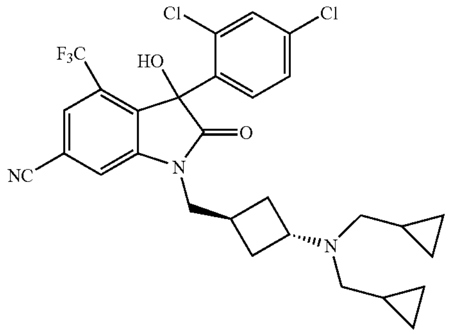

3-(2,4-dichlorophenyl)-1-[trans-3-(dicyclopropylamino)-cyclobutylmethyl]-4-trifluoromethyl-3-hydroxy-6-iodo-1,3-dihydro-2H-indol-2-one (30 mg, 0.04 mmol) was used in a similar manner to Example 1-3 to give the titled compound (21 mg, 84%).

$^1$H NMR ($CDCl_3$, 400 MHz) δ 8.00 (d, 1H, J=8.6 Hz), 7.59 (s, 1H), 7.43 (dd, 1H, J=2.0, 8.6 Hz), 7.32 (s, 1H), 7.28 (d, 1H,

J=2.0 Hz), 4.00 (dd, 1H, J=8.8, 14.2 Hz), 3.89 (dd, 1H, J=7.8, 14.2 Hz), 3.62-3.52 (m, 1H), 2.68-2.57 (m, 1H), 2.42 (d, 4H, J=6.4 Hz), 2.20-1.92 (m, 4H), 0.90-0.80 (m, 2H), 0.54-0.47 (m, 4H), 0.10-0.06 (m, 4H)[0186]

Example 5-2

3-(2,4-dichlorophenyl)-1-[trans-3-(dicyclopropylamino)-cyclobutylmethyl]-4-trifluoromethyl-3-hydroxy-2-oxoindoline-6-carboxamide hydrochloride

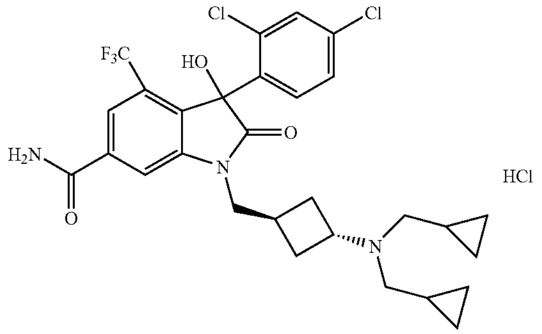

The compound of Example 5-1 (21 mg, 0.04 mmol) was used in a similar manner to Example 1-4 to give the titled compound (22 mg, 95%).

$^1$H NMR (DMSO-$d_6$, 400 MHz) δ 9.95 (brs, 1H), 8.36 (s, 1H), 8.07 (d, 1H, J=8.7 Hz), 7.98 (s, 1H), 7.82 (s, 1H), 7.76 (s, 1H), 7.59 (dd, 1H, J=2.1, 8.7 Hz), 7.55 (d, 11, J=2.1 Hz), 7.45 (s, 1H), 4.32-4.17 (m, 1H), 4.09-3.92 (m, 2H), 3.06-2.88 (m, 4H), 2.78-2.63 (m, 1H), 2.60-2.42 (m, 2H), 2.24-2.07 (m, 2H), 1.04-1.00 (m, 2H), 0.70-0.56 (m, 4H), 0.50-0.31 (m, 4H).

Example 6

3-(2,4-dichlorophenyl)-1-[cis-3-(dimethylamino)-cyclobutylmethyl]-4-trifluoromethyl-3-hydroxy-2-oxoindoline-6-carboxamide Hydrochloride Example 6-1

3-(2,4-dichlorophenyl)-1-[cis-3-(dimethylamino)-cyclobutylmethyl]-4-trifluoromethyl-3-hydroxy-6-iodo-1,3-dihydro-2H-indol-2-one

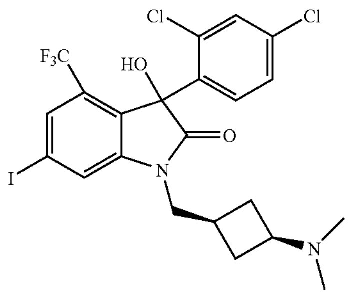

The compound of Reference example 4-5 (50 mg, 0.09 mmol) and dimethylamine hydrochloride were reacted in a similar manner to Example 4-3 to give the titled compound (33.5 mg, 64%).

$^1$H NMR ($CDCl_3$, 400 MHz) δ 8.10 (d, 1H, J=8.8 Hz), 7.59 (s, 1H), 7.38 (dd, 1H, J=2.0, 8.8 Hz), 7.37 (s, 1H), 7.24 (d, 1H, J=2.0 Hz), 4.02-3.89 (m, 1H), 3.67-3.55 (m, 1H), 2.51-2.37 (m, 2H), 2.31-2.15 (m, 2H), 2.01 (s, 6H), 1.87-1.75 (m, 1H), 1.72-1.60 (m, 1H).

Example 6-2

3-(2,4-dichlorophenyl)-1-[cis-3-(dimethylamino)-cyclobutylmethyl]-4-trifluoromethyl-3-hydroxy-6-cyano-1,3-dihydro-2H-indol-2-one

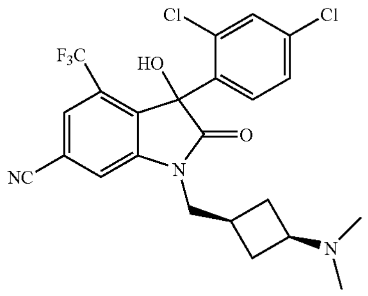

The compound of Example 6-1 (33.5 mg, 0.06 mmol) was used in a similar manner to Example 1-3 to give the titled compound (23.4 mg, 84%).

$^1$H NMR ($CDCl_3$, 400 MHz) δ 8.12 (d, 1H, J=8.6 Hz), 7.57 (s, 1H), 7.41 (dd, 1H, J=2.2, 8.6 Hz), 7.25 (d, 1H, J=2.2 Hz), 7.24 (s, 1H), 4.09 (dd, 1H, J=4.0, 14.4 Hz), 3.60 (dd, 1H, J=4.8, 14.4 Hz), 2.58-2.43 (m, 2H), 2.38-2.17 (m, 2H), 2.00 (S 6H), 1.89-1.79 (m, 1H) 1.67-1.57 (m, 1H).

Example 6-3

3(2,4-dichlorophenyl)-1-[cis-3-(dimethylamino)-cyclobutylmethyl]-4-trifluoromethyl-3-hydroxy-2-oxoindoline-6-carboxamide Hydrochloride

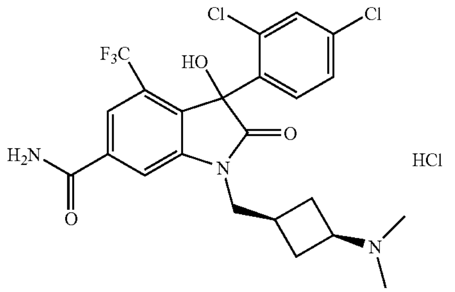

The compound of Example 6-2 was used in a similar manner to Example 1-4 to give the titled compound (35.5 mg, quant.).

$^1$H NMR (DMSO-$d_6$, 400 MHz) δ 9.96 (brs, 1H), 8.33 (s, 1H), 8.07 (d, 1H, J=8.7 Hz), 7.93 (s, 1H), 7.82 (s, 1H), 7.77 (s, 1H), 7.58 (dd, 1H, J=2.2, 8.7 Hz), 7.50 (d, 1H, J=2.2 Hz), 7.42 (s, 1H), 3.89 (d, 2H, J=6.8 Hz), 3.60-3.40 (m, 1H), 2.72-2.55 (m, 1H), 2.63 (s, 6H), 2.45-2.30 (m, 2H), 2.15-2.00 (m, 2H).

Example 7

3-(2,4-dichlorophenyl)-1-[cis-3-(diethylamino)-cyclobutylmethyl]-4-trifluoromethyl-3-hydroxy-2-oxoindoline-6-carboxamide Hydrochloride Example 7-1 cis-3-diethylaminocyclobutane Carboxylic Benzyl Ester

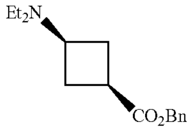

To a solution of 3-oxocyclobutane carboxylic benzyl ester (88.1 mg, 0.43 mmol) in dichloromethane (4.3 mL) were successively added diethylamine (0.18 mL, 1.73 mmol) and sodium triacetoxyborohydride (137.0 mg, 0.65 mmol). The mixture was stirred at room temperature for 5 hours, and then to the reaction solution was added saturated aqueous ammonium chloride solution, and the mixture was extracted with ethyl acetate. The organic layer was dried over anhydrous magnesium sulfate and filtered, and then evaporated. The resulting residue was purified by silica gel column chromatography (chloroform/methanol 20/1 to 5/1) to give the titled compound (66.3 mg, 59%).

$^1$H NMR ($CDCl_3$, 400 MHz) δ 7.42-7.30 (m, 5H), 5.10 (s, 2H), 3.10-3.00 (m, 1H), 2.80-2.72 (m, 1H), 2.51 (q, 4H, J=7.1 Hz), 2.38-2.28 (m, 2H), 2.23-2.10 (m, 2H), 0.97 (t, 6H, J=7.1 Hz).

Example 7-2

(cis-3-diethylaminocyclobutyl)-methanol

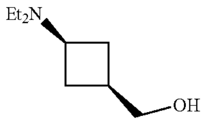

The compound of Example 7-1 (36.5 mg, 0.14 mmol) was used in a similar manner to Example 1-3 to give the titled compound (22.0 mg, quant.).

$^1$H NMR ($CDCl_3$, 400 MHz) δ 3.57 (d, 2H, J=4.5 Hz), 3.00-2.90 (m, 1H), 3.01-2.91 (m, 1H), 2.52 (q, 4H, J=7.2 Hz), 2.32-2.27 (m, 3H), 1.73-1.61 (m, 2H), 0.97 (t, 6H, J=7.2 Hz).

Example 7-3

3-(2,4-dichlorophenyl)-1-[cis-3-(diethylamino) cyclobutylmethyl]-4-trifluoromethyl-3-hydroxy-6-iodo-1,3-dihydro-2H-indol-2-one

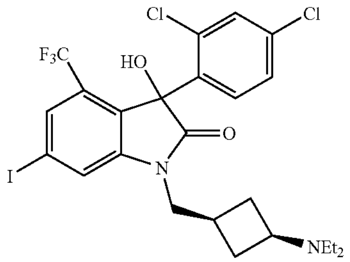

The compound of Example 7-2 (47.2 mg, 0.30 mmol) and the compound of Reference example 1-4 were reacted in a similar manner to Example 3-3 to give the titled compound (98.8 mg, 70%).

$^1$H NMR ($CDCl_3$, 400 MHz) δ 8.07 (d, 1H, J=7.2 Hz), 7.60 (s, 1H), 7.38 (s, 1H), 7.37 (dd, 1H, J=2.4, 7.2 Hz), 7.23 (d, 1H, J=2.4 Hz), 4.00-3.80 (m, 1H), 3.70-3.58 (m, 1H), 2.95-2.83 (m, 1H), 2.50-2.33 (m, 5H), 2.30-2.14 (m, 2H), 1.85-1.75 (m, 1H), 1.75-1.63 (m, 1H), 0.92 (t, 6H, J=6.6 Hz).

Example 7-4

3-(2,4-dichlorophenyl)-1-[cis-3-(diethylamino)-cyclobutylmethyl]-4-trifluoromethyl-3-hydroxy-6-cyano-1,3-dihydro-2H-indol-2-one

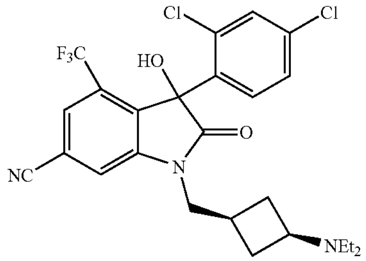

The compound of Example 7-3 (98.8 mg, 0.16 mmol) was used in a similar manner to Example 1-3 to give the titled compound (73.8 mg, 89%).

$^1$H NMR ($CDCl_3$, 400 MHz) δ 8.16 (d, 1H, J=8.6 Hz), 7.55 (s, 1H), 7.39 (dd, 1H, J=2.1, 8.6 Hz), 7.23 (d, 1H, J=2.1 Hz), 7.20 (s, 1H), 4.10 (dd, 1H, J=2.2, 14.7 Hz), 3.55 (dd, 1H, J=3.8, 14.7 Hz), 3.10-2.88 (m, 1H), 2.68-2.35 (m, 5H), 2.35-2.18 (m, 2H), 2.10-1.60 (m, 2H), 1.06-0.77 (m, 6H).

Example 7-5

3-(2,4-dichlorophenyl)-1-[cis-3-(diethylamino)-cyclobutylmethyl]-4-trifluoromethyl-3-hydroxy-2-oxoindoline-6-carboxamide Hydrochloride

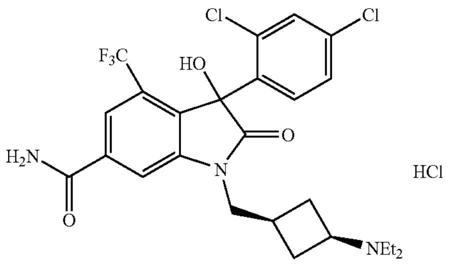

The compound of Example 7-4 (73.8 mg, 0.14 mmol) was used in a similar manner to Example 1-4 to give the titled compound (69.1 mg, 85%).

$^1$H NMR (DMSO-$d_6$, 400 MHz) δ 10.20 (brs, 1H), 8.38 (s, 1H), 8.07 (d, 1H, J=8.7 Hz), 8.04 (s, 1H), 7.83 (s, 1H), 7.78 (s, 1H), 7.58 (dd, 1H, J=2.2, 8.7 Hz), 7.50 (d, 1H, J=2.2 Hz), 7.45 (s, 1H), 3.93 (dd, 1H, J=5.8, 14.4 Hz), 3.88 (dd, 1H, J=6.8, 14.4 Hz), 3.70-3.58 (m, 1H), 3.11-2.98 (m, 2H), 2.98-2.85 (m, 2H), 2.50-2.42 (m, 1H), 2.42-2.30 (m, 2H), 2.30-2.18 (m, 2H), 1.14 (t, 6H, J=7.2 Hz).

Example 8

3-(2,4-dichlorophenyl)-1-[trans-3-(diethylamino)-cyclobutylmethyl]-4-trifluoromethyl-3-hydroxy-2-oxoindoline-6-carboxylic Acid Hydrobromide

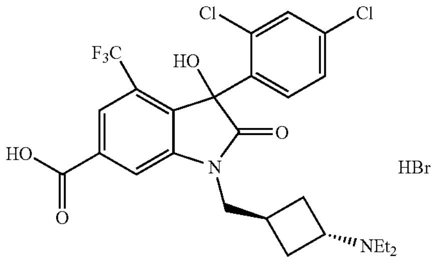

To a solution of the compound of Example 1-4 (400.0 mg, 0.69 mmol) in acetic acid (2.5 mL) was added 47% hydrobromic acid (7.5 mL), and the mixture was stirred at 100° C. for 2 hours. The reaction solution was concentrated, and then recrystallized (methanol-diethyl ether) to give the titled compound (420.5 mg, 98%).

$^1$H NMR (DMSO-$d_6$, 400 MHz) δ 13.75 (1H, brs), 9.46 (brs, 1H), 8.07 (d, 1H, J=8.5 Hz), 7.95 (d, 1H, J=0.7 Hz), 7.80 (d, 1H, J=0.7 Hz), 7.60 (dd, 1H, J=2.0, 8.6 Hz), 7.52 (s, 1H), 7.51 (d, 1H, J=2.0 Hz), 4.20-4.11 (m, 1H), 4.11-4.00 (m, 2H), 3.15-2.90 (m, 4H), 2.73-2.60 (m, 1H), 2.48-2.32 (m, 2H), 2.22-2.07 (m, 2H), 1.15 (t, 6H, J=7.2 Hz).

Example 9

N,N-dimethyl-3-(2,4-dichlorophenyl)-1-[trans-3-(diethylamino)-cyclobutylmethyl]-4-trifluoromethyl-3-hydroxy-2-oxoindoline-6-carboxamide Hydrochloride

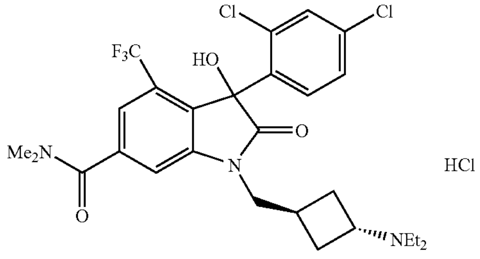

To a solution of the compound of Example 8 (200 mg, 0.32 mmol) in dichloromethane (5 mL) and N,N-dimethylformamide (5 mL) were added excess amount of dimethylamine and bis-(2-oxo-3-oxazolidinyl)-phosphinic chloride (325.2 mg, 1.27 mmol), and the mixture was stirred at room temperature for 28 hours. To the reaction solution was added saturated aqueous sodium bicarbonate, and the mixture was extracted with ethyl acetate-toluene (1:1). The organic layer was dried over anhydrous magnesium sulfate, and then filtered and concentrated, and the resulting residue was purified by silica gel column chromatography (chloroform/methanol/ammonia water=20/1/0 to 10/1/0 to 200/10/1 to 100/10/1). To the purified substance were added tetrahydrofuran and 1M hydrochloric acid (1 mL), and the mixture was concentrated. The resulting solid was suspended in diethyl ether, and then filtered to give the titled compound (139.0 mg, 72%).

$^1$H NMR (DMSO-$d_6$, 400 MHz) δ 10.24 (brs, 1H), 8.07 (d, 1H, J=8.6 Hz), 7.64 (s, 1H), 7.58 (dd, 1H, J=2.3, 8.6 Hz), 7.51 (d, 1H, J=2.3 Hz), 7.41 (s, 1H), 7.28 (s, 1H), 4.18-3.92 (m, 3H), 3.10-3.00 (m, 2H), 3.02 (s, 3H), 3.00-2.88 (m, 2H), 2.91 (s, 3H), 2.69-2.56 (m, 1H), 2.55-2.39 (m, 2H), 2.15-2.00 (m, 2H), 1.15 (t, 6H, J=7.0 Hz).

Example 10

N-methyl-3-(2,4-dichlorophenyl)-1-[trans-3-(diethylamino)-cyclobutylmethyl]-4-trifluoromethyl-3-hydroxy-2-oxoindoline-6-carboxamide hydrochloride

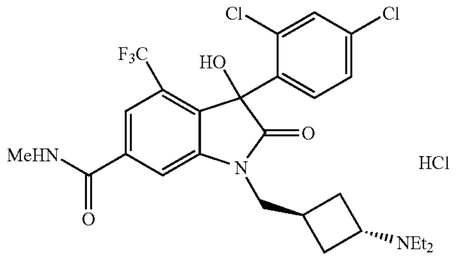

The compound of Example 8 (200 mg, 0.32 mmol) and excess amount of methylamine were reacted in a similar manner to Example 9 to give the titled compound (75.0 mg, 40%).

$^1$H NMR (DMSO-$d_6$, 400 MHz) δ 10.39 (brs, 1H), 8.92 (q, 1H, J=4.4 Hz), 8.07 (d, 1H, J=8.6 Hz), 8.00 (s, 1H), 7.77 (s, 1H), 7.58 (dd, 1H, J=2.0, 8.6 Hz), 7.49 (d, 1H, J=2.0 Hz), 7.46 (s, 1H), 4.12-3.95 (m, 3H), 3.12-2.88 (m, 4H), 2.83 (d, 3H, J=4.4 Hz), 2.77-2.65 (m, 1H), 2.57-2.43 (m, 2H), 2.18-2.05 (m, 2H), 1.16 (t, 6H, J=7.2 Hz).

Example 11

3-(2,4-dichlorophenyl)-1-[trans-3-(diethylamino)-cyclobutylmethyl]-4-trifluoromethyl-3-fluoro-2-oxoindoline-6-carboxamide Hydrochloride

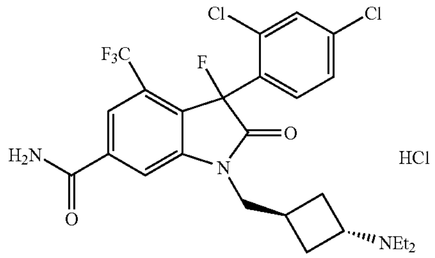

To the compound of Example 1-4 (150.0 mg, 0.26 mmol) was added saturated aqueous sodium bicarbonate, and the mixture was extracted with ethyl acetate, dried over anhydrous magnesium sulfate, filtered and concentrated. The residue was dissolved in dichloromethane (2.6 mL), and thereto was added diethylaminosulfur trifluoride (207.9 mg, 1.29 mmol) at −78° C., and the mixture was allowed to warm to room temperature and stirred for 24 hours. To the reaction solution was added saturated aqueous sodium bicarbonate, and the mixture was extracted with ethyl acetate. The organic layer was dried over anhydrous magnesium sulfate, filtered and concentrated, and then purified by silica gel column chromatography (chloroform/methanol/ammonia water 20/1/0 to 10/1/0 to 100/10/1), and then by preparative liquid chromatography. To the purified substance were added tetrahydrofuran and 1M hydrochloric acid (0.5 mL), and the mixture was concentrated. The resulting solid was suspended in diethyl ether and filtered to give the titled compound (65.0 mg, 43%).

$^1$H NMR (DMSO-$d_6$, 400 MHz) δ 10.48 (brs, 1H), 8.47 (s, 1H), 8.16 (s, 1H), 7.92 (s, 1H), 7.88 (d, 1H, J=8.0 Hz), 7.87 (s, 1H), 7.69 (s, 1H), 7.68 (d, 1H, J=8.0 Hz), 4.21-4.01 (m, 3H), 3.10-2.88 (m, 4H), 2.78-2.68 (m, 1H), 2.60-2.46 (m, 2H), 2.15-2.03 (m, 2H), 1.16 (t, 3H, J=7.2 Hz), 1.15 (t, 3H, J=7.4 Hz).

Example 12

3-(2,4-dichlorophenyl)-1-[trans-3-(diethylamino)-cyclobutyl]-4-trifluoromethyl-3-hydroxy-2-oxoindoline-6-carboxamide Hydrochloride Example 12-1

3-(2,4-dichlorophenyl)-1-[cis-3-(diethylamino)-cyclobutylmethyl]-4-trifluoromethyl-3-hydroxy-6-iodo-1,3-dihydro-2H-indol-2-one

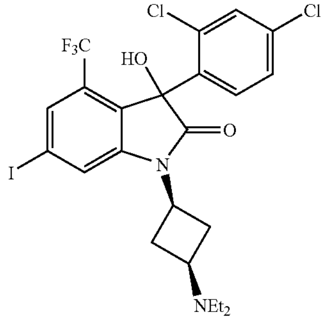

The compound of Reference example 1-4 (360 mg, 0.598 mmol) and the compound of Reference example 3-2 (85.7 mg, 0.598 mmol) were reacted in a similar manner to Example 3-3 to give the titled compound (113 mg, 31%).

$^1$H NMR ($CDCl_3$, 400 MHz) δ 8.07 (s, 1H), 7.98 (d, 1H, J=8.6 Hz), 7.62 (s, 1H), 7.37 (dd, 1H, J=2.1, 8.6 Hz), 7.25 (d, 1H, J=2.1 Hz), 4.36-4.45 (m, 1H), 3.51 (brs, 1H), 3.01-3.08 (m, 1H), 2.58-2.71 (m, 4H), 2.57 (q, 4H, J=7.2 Hz), 1.03 (t, 6H, J=7.2 Hz).

Example 12-2

3-(2,4-dichlorophenyl)-1-[cis-3-(diethylamino)-cyclobutylmethyl]-4-trifluoromethyl-3-hydroxy-6-cyano-1,3-dihydro-2H-indol-2-one

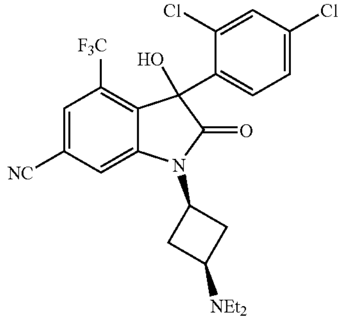

The compound of Example 12-1 (99.1 mg, 0.162 mmol) was treated in a similar manner to Example 1-3 to give the titled compound (86.4 mg, quant.).

LC-MS m/z 512, 514 ($M+H^+$).

$^1$H NMR ($CDCl_3$, 400 MHz) δ 8.08 (s, 1H), 7.98 (d, 1H, J=8.5 Hz), 7.58 (s, 1H), 7.39 (dd, 1H, J=2.1, 8.5 Hz), 7.26 (d, 1H, J=2.1 Hz), 4.43-4.51 (m, 1H), 3.03-3.10 (m, 1H), 2.51-2.75 (m, 4H), 2.56 (q, 4H, J=7.1 HZ), 1.02 (t, 6H, J=7.1 Hz).

Example 12-3

3-(2,4-dichlorophenyl)-1-[(trans-3-(diethylamino)-cyclobutyl]-4-trifluoromethyl-3-hydroxy-2-oxoindoline-6-carboxamide hydrochloride

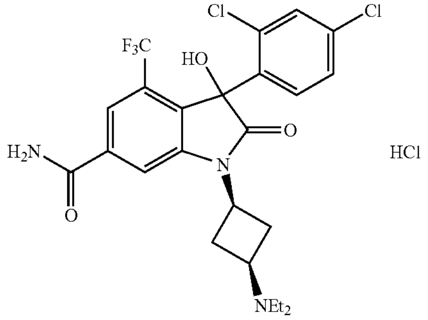

The compound of Example 12-2 (64.4 mg, 0.126 mmol) was treated in a similar manner to Example 1-4 to give the titled compound (34.3 mg, 48%).

LC-MS m/z 530, 532 ($M+H^+$).

$^1$H NMR (DMSO-$d_6$, 400 MHz) δ 10.60 (brs, 1H), 8.51 (brs, 1H), 8.06 (d, 1H, J=8.6 Hz), 7.93 (s, 1H), 7.87 (s, 1H), 7.77 (brs, 1H), 7.58 (dd, 1H, J=1.7, 8.6 Hz), 7.50 (d, 1H, J=1.7

Hz), 7.45 (br, 1H), 4.37-4.55 (m, 1H), 3.61-3.67 (m, 1H), 2.99-3.18 (m, 6H), 2.85-2.89 (m, 2H), 1.20 (t, 6H, J=7.1 Hz).

Example 13

3-(2,4,6-trifluorophenyl)-1-[trans-3-(diethylamino)-cyclobutyl]-4-trifluoromethyl-3-hydroxy-2-oxoindoline-6-carboxamide Hydrochloride Example 13-1

3-(2,4,6-trifluorophenyl)-1-[trans-3-(diethylamino)-cyclobutylmethyl]-4-trifluoromethyl-3-hydroxy-6-iodo-1,3-dihydro-2H-indol-2-one

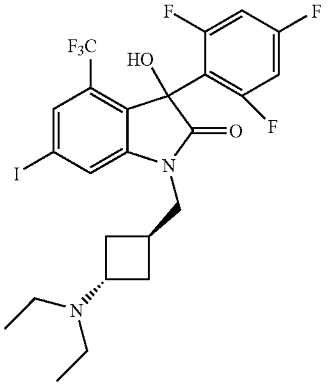

A solution of 1,3,5-trifluorobenzene (318 mg, 2.41 mmol) in tetrahydrofuran (6.0 mL) was cooled to 78° C. under nitrogen, and thereto was added dropwise 2N lithium diisopropylamide (1.53 mL, 3.06 mmol), and the mixture was stirred for 30 minutes, Then, thereto was added dropwise a solution of the compound of Example 1-1 (650 mg, 1.34 mmol) in tetrahydrofuran (16 mL), and the mixture was stirred at −78° C. for 3 hours. To the reaction solution was added saturated aqueous sodium bicarbonate, and the mixture was extracted with ethyl acetate, dried over magnesium sulfate and filtered. The filtrate was evaporated and purified by silica gel column chromatography (hexane/ethyl acetate/ammonia water=50/1/0.25 to 30/1/0.16 to 20/1/0.1) to give the titled compound (223 mg, 27%).

LC-MS m/z 613 ($M+H^+$).

$^1$H NMR ($CDCl_3$, 400 MHz) δ 7.63 (s, 1H), 7.40 (s, 1H), 6.63-6.67 (m, 2H), 3.89 (dd, 1H, J=8.5, 14.2 Hz), 3.80 (dd, 1H, J=7.9, 14.2 Hz), 3.35-3.40 (m, 1H), 2.61-2.63 (m, 1H), 2.50 (q, 4H, J=7.1 Hz), 2.07-2.15 (m, 2H), 1.94-1.96 (m, 2H), 0.97 (t, 6H, J=7.1 Hz).

Example 13-2

3-(2,4,6-trifluorophenyl)-1-[trans-3-(diethylamino)-cyclobutylmethyl]-4-trifluoromethyl-3-hydroxy-6-cyano-1,3-dihydro-2H-indol-2-one

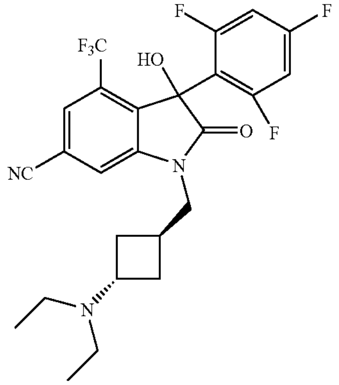

The compound of Example 13-1 (218 mg, 0.358 mmol) was treated in a similar manner to Example 1-3 to give the titled compound (120 mg, 66%).

LC-MS m/z 512 ($M+H^+$).

$^1$H NMR ($CDCl_3$, 400 MHz) δ 7.60 (d, 1H, J=0.5 Hz), 7.30 (d, 1H, J=0.5 Hz), 6.65-6.70 (m, 2H), 3.98 (dd, 1H, J=8.6, 14.3 Hz), 3.84 (dd, 1H, J=7.9, 14.3 Hz), 3.34-3.42 (m, 1H), 2.57-2.64 (m, 1H), 2.49 (q, 4H, J=7.2 Hz), 2.07-2.15 (m, 2H), 1.88-1.98 (m, 2H), 0.96 (t, 6H, J=7.2 Hz).

Example 13-3

3-(2,4,6-trifluorophenyl)-1-[trans-3-(diethylamino)-cyclobutyl]-4-trifluoromethyl-3-hydroxy-2-oxoindoline-6-carboxamide Hydrochloride

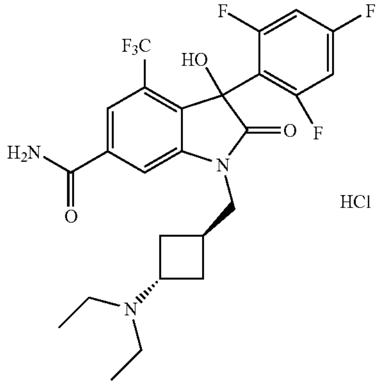

The compound of Example 13-2 (105 mg, 0.205 mmol) was treated in a similar manner to Example 1-4 to give the titled compound (58.5 mg, 50%). The purification was carried out by preparative liquid chromatography.

$^1$H NMR (DMSO-$d_6$, 400 MHz) δ 10.29 (brs, 1H), 8.34 (brs, 1H), 7.98 (s, 1H), 7.83 (s, 1H), 7.76 (brs, 1H), 7.14-7.18 (m, 3H), 4.08-4.14 (m, 1H), 3.93-4.06 (m, 2H), 2.96-3.07 (m, 4H), 2.67-2.72 (m, 1H), 2.43-2.50 (m, 2H), 1.91-2.10 (m, 2H), 1.16 (t, 6H, J=7.2 Hz)

LC-MS m/z 530 ($M+H^+$). .

Example 14

3-(2,4-dichlorophenyl)-1-[trans-3-(diethylamino)-cyclobutylmethyl]-4-trifluoromethyl-3-hydroxy-6-(2-oxazolyl)-1,3-dihydro-2H-indol-2-one Example 14-1

3-(2,4-dichlorophenyl)-1-[trans-3-(diethylamino)-cyclobutylmethyl]-4-trifluoromethyl-3-triethylsilyloxy-6-iodo-1,3-dihydro-2H-indol-2-one

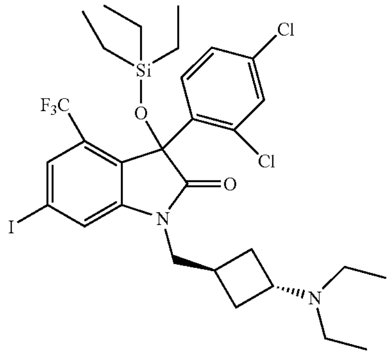

To a solution of the compound of Reference example 1-4 (2.00 g, 3.32 mmol), the compound of Reference example 5-3 (530 mg, 3.37 mmol) and triphenylphosphine (1.00 g, 3.80 mmol) in tetrahydrofuran (30 mL) was added diisopropyl diazocarboxylate (780 mg, 3.85 mmol) under nitrogen under an ice-cooled bath, and the mixture was stirred at room temperature for 12 hours. To the reaction solution was added water (50 mL), and the mixture was extracted with ethyl acetate (50 mL), and then the organic layer was washed with saturated saline (50 mL), dried over magnesium sulfate and filtered. The filtrate was concentrated in vacuo and the residue was purified by silica gel chromatography (chloroform/methanol=20/1) to give the titled compound (2.00 g, 81%).

$^1$H NMR ($CDCl_3$, 400 MHz) δ 8.02 (d, 1H, J=8.6 Hz) 7.59 (s, 1H), 7.36 (dd, 1H, J=2.1 and 8.6 Hz), 7.35 (s, 1H), 7.21 (d, 1H, J=2.1 Hz), 4.13-4.06 (m, 1H), 3.68-3.62 (m, 1H), 3.48-3.39 (m, 1H), 2.66-2.48 (m, 5H), 2.31-1.99 (m, 4H), 1.01 (t, 6H, J=7.0 Hz), 0.84 (t, 9H, J=7.9 Hz), 0.44 (q, 6H, J=7.9 Hz).

Example 14-2

3-(2,4-dichlorophenyl)-1-[trans-3-(diethylamino)-cyclobutylmethyl]-4-trifluoromethyl-3-triethylsilyloxy-6-(2-oxazolyl)-1,3-dihydro-2H-indol-2-one

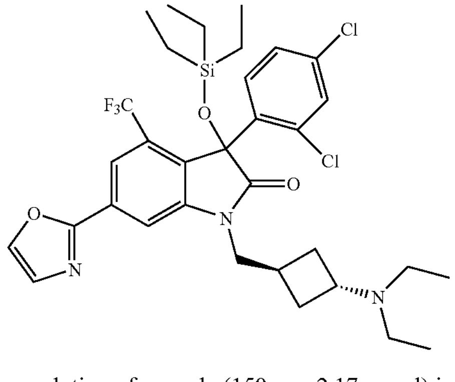

To a solution of oxazole (150 mg, 2.17 mmol) in tetrahydrofuran (4 mL) was added 2.67 M n-butyl lithium hexane solution (0.8 mL, 2.14 mmol) at −78° C. under nitrogen, and the mixture was stirred for 15 minutes. To the reaction solution was added 1.0M zinc chloride diethyl ether solution (2.2 mL, 2.2 mmol) at −78° C., and the mixture was stirred for 15 minutes. The reaction solution was allowed to warm to 0° C., and then thereto was added a solution of the compound of Example 14-1 (310 mg, 0.418 mmol) and tetrakistriphenylphosphine palladium (20 mg, 0.017 mmol) in tetrahydrofuran (5 mL), and the mixture was stirred at room temperature for 1 hour, and then the mixture was heated to stir at 60° C. for 3 hours. To the reaction solution was added water, and the mixture was extracted with ethyl acetate, and then the organic layer was washed with saturated saline, dried over magnesium sulfate and filtered. The filtrate was concentrated in vacuo and the residue was purified by silica gel chromatography (chloroform/methanol=20/1) to give the titled compound (160 mg, 56%).

$^1$H NMR ($CDCl_3$, 400 MHz) δ 8.06 (d, 1H, J=8.6 Hz), 7.95 (s, 1H), 7.80 (d, 1H, J=0.7 Hz), 7.72 (s, 1H), 7.38 (dd, 1H, J=2.1 and 8.6 Hz), 7.32 (d, 1H, J=0.7 Hz), 7.21 (d, 1H, J=2.1 Hz), 4.23-4.16 (m, 1H), 3.81-3.75 (m, 1H), 3.47-3.42 (m, 1H), 2.71-2.65 (m, 1H), 2.51 (q, 4H, J=7.1 Hz), 2.19-1.99 (m, 4H), 0.98 (t, 6H, J=7.0 Hz), 0.84 (t, 9H, J=7.9 Hz), 0.44 (q, 6H, J=7.9 Hz).

Example 14-3

3-(2,4-dichlorophenyl)-1-[trans-3-(diethylamino)-cyclobutylmethyl]-4-trifluoromethyl-3-hydroxy-6-(2-oxazolyl)-1,3-dihydro-2H-indol-2-one

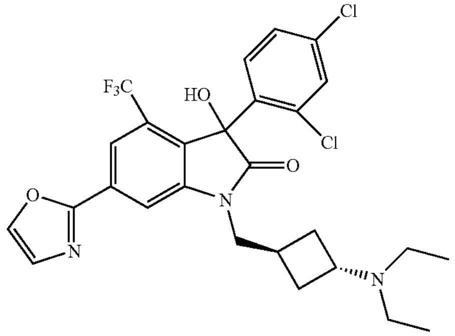

To a solution of the compound of Example 14-2 (160 mg, 0.234 mmol) in tetrahydrofuran (6 mL) was added tetra-n-butylammonium fluoride (100 mg, 0.383 mmol) under nitrogen, and the mixture was stirred at room temperature for 2 hours. To the reaction solution was added, and the mixture was extracted with ethyl acetate, and then the organic layer was washed with saturated saline, dried over magnesium sulfate and filtered. The filtrate was concentrated in vacuo and the residue was purified by silica gel chromatography (chloroform/methanol=10/1) to give the titled compound (80 mg, 60%).

$^1$H NMR ($CDCl_3$, 400 MHz) δ 8.05 (d, 1H, J=8.6 Hz), 7.98 (s, 1H), 7.79 (d, 1H, J=0.7 Hz), 7.76 (s, 1H), 7.42 (dd, 1H, J=2.1 and 8.6 Hz), 7.31 (d, 1H, J=0.7 Hz), 7.27 (d, 1H, J=2.1 Hz), 4.10-3.91 (m, 2H), 3.52-3.47 (m, 1H), 2.79-2.70 (m, 1H), 2.64-2.55 (br, 4H), 2.35-2.19 (m, 2H), 2.15-1.99 (m, 2H), 1.03 (t, 6H, J=6.8 Hz).

Example 14-4

3-(2,4-dichlorophenyl)-1-[trans-3-(diethylamino)-cyclobutylmethyl]-4-trifluoromethyl-3-hydroxy-6-(2-oxazolyl)-1,3-dihydro-2H-indol-2-one hydrochloride

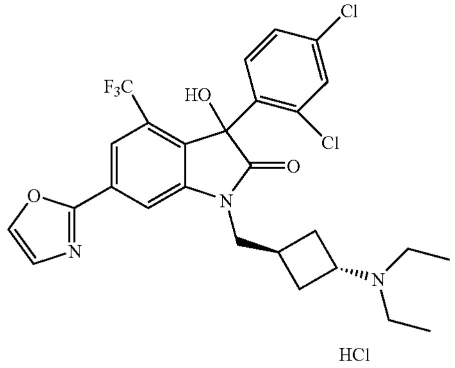

To a solution of the compound of Example 14-3 (80 mg, 0.140 mmol) in acetonitrile (1 mL) was added 4N hydrochloric acid (0.1 mL), and the mixture was concentrated in vacuo and dried to give the titled compound (80 mg, quant.).

$^1$H NMR (DMSO-$d_6$, 400 MHz) δ 10.61 (br, 1H), 8.36 (s, 1H), 8.09 (d, 1H, J=8.6 Hz), 8.02 (s, 1H), 7.84 (s, 1H), 7.60 (dd, 1H, J=2.1 and 8.6 Hz), 7.53-5.48 (m, 3H), 4.15-4.08 (m, 3H), 3.06-2.91 (m, 4H), 2.75-2.68 (m, 1H), 2.63-2.50 (m, 2H), 2.16-2.12 (m, 2H), 1.16 (t, 6H, J=6.2 HZ).

Example 15

3-(2,4-dichlorophenyl)-1-[trans-3-(diethylamino)-cyclobutylmethyl]-4-trifluoromethyl-3-hydroxy-6-(2-furyl)-1,3-dihydro-2H-indol-2-one Hydrochloride Example 15-1

3-(2,4-dichlorophenyl)-1-[trans-3-(diethylamino)-cyclobutylmethyl]-4-trifluoromethyl-3-triethylsilyloxy-6-(2-furyl)-1,3-dihydro-2H-indol-2-one

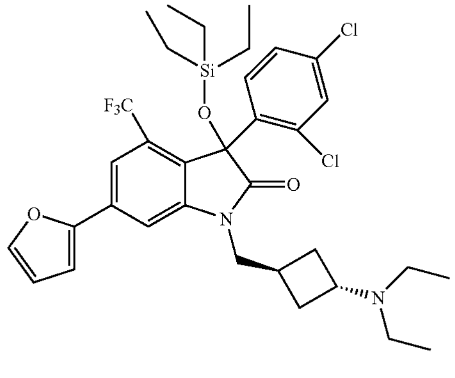

A solution of the compound of Example 14-1 (140 mg, 0.188 mmol), 2-tributyltinfuran (80 mg, 0.224 mmol) and tetrakistriphenylphosphine palladium (20 mg, 0.017 mmol) in toluene (5 mL) was stirred at 100° C. under nitrogen for 3 hours. To the reaction solution was added water, and the mixture was extracted with ethyl acetate, and then the organic layer was washed with saturated saline, dried over magnesium sulfate and filtered. The filtrate was concentrated in vacuo and the residue was purified by silica gel chromatography (chloroform/methanol=20/1) to give the titled compound (80 mg, 63%).

LC-MS m/z 681 (M+H$^+$).

Example 15-2

3-(2,4-dichlorophenyl)-1-[trans-3-(diethylamino)-cyclobutylmethyl]-4-trifluoromethyl-3-hydroxy-6-(2-furyl)-1,3-dihydro-2H-indol-2-one hydrochloride

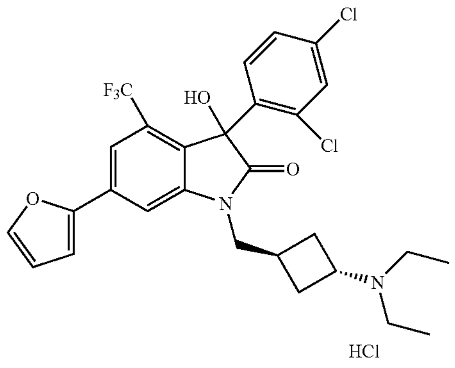

The compound of Example 15-1 was used in a similar manner to Example 14-3 to 14-4 to give the titled compound.

$^1$H NMR (DMSO-$d_6$, 400 MHz) δ 10.37 (br, 1H), 8.07 (d, 1H, J=8.6 Hz), 7.86 (d, 1H, J=1.6 Hz), 7.80 (s, 1H), 7.59-7.51 (m, 2H), 7.49 (d, 1H, J=2.1 Hz), 7.29-7.18 (m, 2H), 6.70 (dd, 1H, J=1.6 and 2.1 Hz), 4.15-4.05 (m, 3H), 3.16-2.91 (m, 4H), 2.75-2.68 (m, 1H), 2.61-2.48 (m, 2H), 2.17-2.12 (m, 2H), 1.16 (t, 6H, J=6.1 Hz).

Example 16-1

3-(2,4-dichlorophenyl)-1-[trans-3-(diethylamino)-cyclobutylmethyl]-4-trifluoromethyl-3-hydroxy-6-(1-triazolyl)-1,3-dihydro-2H-indol-2-one

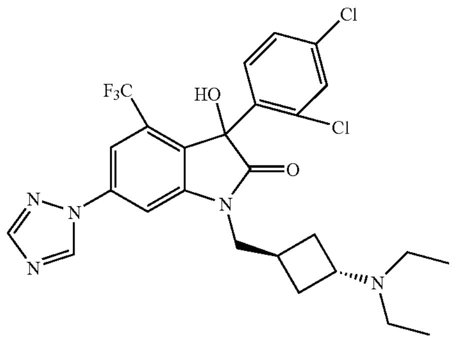

To a solution of the compound of Example 14-1 (75 mg, 0.101 mmol) in N,N-dimethylformamide (1 mL) were added triazole (7.0 mg, 0.101 mmol), potassium phosphate (43 mg, 0.202 mmol), N,N'-dimethylethylenediamine (15 mg, 0.170 mmol) and copper iodide (I) (1.0 mg, 0.01 mmol) under nitrogen, and the mixture was stirred at 100° C. for 8 hours. To the reaction solution was added water, and the mixture was extracted with ethyl acetate, and then the organic layer was washed with saturated saline, dried over magnesium sulfate and filtered. The filtrate was concentrated in vacuo and the residue was purified by silica gel chromatography (chloroform/methanol/28% ammonia water=100/5/1) to give the titled compound (20 mg, 63%).

LC-MS m/z 568 ($M+H^+$).

Example 16-2

3-(2,4-dichlorophenyl)-1-[trans-3-(diethylamino)-cyclobutylmethyl]-4-trifluoromethyl-3-hydroxy-6-(1-triazolyl)-1,3-dihydro-2H-indol-2-one hydrochloride

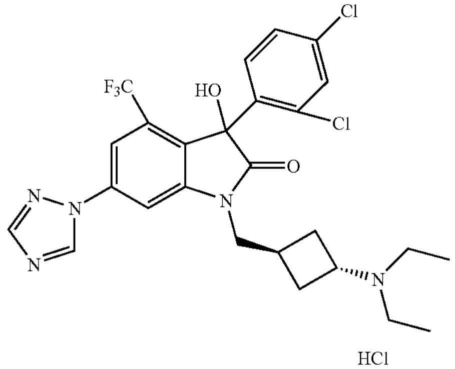

To a solution of the compound of Example 16-1 in acetonitrile was added 4N hydrochloric acid water, and the mixture was concentrated in vacuo and dried to give the titled compound.

$^1$H NMR (DMSO-$d_6$, 400 MHz) δ 10.59 (br, 1H), 9.61 (s, 1H), 8.34 (s, 1H), 8.09 (s, 1H), 8.07 (d, 1H, J=8.6 Hz), 7.78 (s, 1H), 7.59 (dd, 1H, J=2.1 and 8.6 Hz), 7.52-7.46 (m, 2H), 4.16-4.04 (m, 3H), 3.06-2.90 (m, 4H), 2.76-2.71 (m, 1H), 2.56-2.49 (m, 2H), 2.15-2.11 (m, 2H), 1.16 (t, 6H, J=6.1 Hz).

Example 17-1

3-(2,4-dichlorophenyl)-1-[trans-3-(diethylamino)-cyclobutylmethyl]-4-trifluoromethyl-3-hydroxy-6-(2-tetrazolyl)-1,3-dihydro-2H-indol-2-one

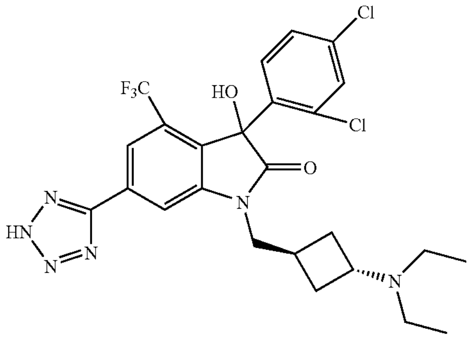

To a solution of the compound of Example 1-3 (40 mg, 0.076 mmol) in toluene (2 mL) were added triethylamine hydrochloride (10.8 mg, 0.076 mmol) and sodium azide (10.0 mg, 0.154 mmol) under nitrogen, and the mixture was stirred at 100° C. for 5 hours. The reaction solution was concentrated in vacuo and the residue was purified by preparative liquid chromatography to give the titled compound (15 mg).

LC-MS m/z 569 ($M+H^+$).

Example 17-2

3-(2,4-dichlorophenyl)-1-[trans-3-(diethylamino)-cyclobutylmethyl]-4-trifluoromethyl-3-hydroxy-6-(2-tetrazolyl)-1,3-dihydro-2H-indol-2-one hydrochloride

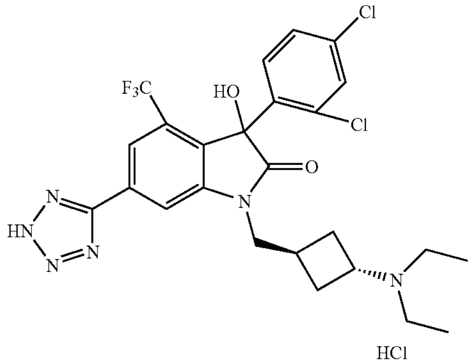

To a solution of the compound of Example 17-1 in acetonitrile was added 4N hydrochloric acid water, and then the mixture was concentrated in vacuo and dried to give the titled compound.

$^1$H NMR (DMSO-$d_6$, 400 MHz) δ 10.14 (br, 1H), 8.31 (s, 1H), 8.09 (d, 1H, J=8.6 Hz), 7.99 (s, 1H), 7.60 (dd, 1H, J=2.1 and 8.6 Hz), 7.54 (s, 1H), 7.52 (d, 1H, J=2.1 Hz), 4.23-4.07 (m, 3H), 3.18-2.95 (m, 4H), 2.78-2.72 (m, 1H), 2.53-2.43 (m, 2H), 2.18-2.07 (m, 2H), 1.15 (t, 6H, J=6.1 Hz).

Example 18

3-(2,4-dichlorophenyl)-1-[trans-3-(diethylamino)-cyclobutyl]-4-trifluoromethyl-3-hydroxy-2-oxoindoline-6-carboxamide Hydrochloride Example 18-1

3-(2,4-dichlorophenyl)-1-[trans-3-(diethylamino)-cyclobutyl]-4-trifluoromethyl-3-hydroxy-6-iodo-1,3-dihydro-2H-indol-2-one

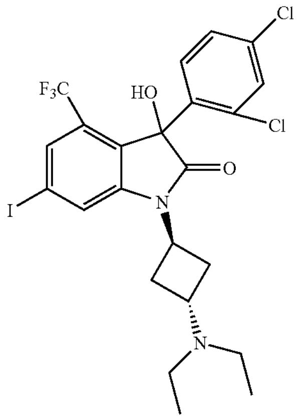

To a solution of the compound of Reference example 1-4 (240 mg, 0.40 mmol), the compound of Reference example 2-3 (57 mg, 0.40 mmol) and triphenylphosphine (210 mg, 0.80 mmol) in tetrahydrofuran (2 mL) was added diisopropyl diazocarboxylate (161 mg, 0.80 mmol) under an ice-cooled bath under nitrogen, and the mixture was stirred at room temperature for 3 hours. To the reaction solution was added water, and the mixture was extracted with ethyl acetate, and then the organic layer was washed with saturated saline, dried over magnesium sulfate and filtered. The filtrate was concentrated in vacuo. The residue was dissolved in THF (5 mL), and thereto was added tetra-n-butylammonium fluoride (100 mg, 0.383 mmol), and the mixture was stirred at room temperature for 2 hours. To the reaction solution was added water, and the mixture was extracted with ethyl acetate, and then the organic layer was washed with saturated saline, dried over magnesium sulfate and filtered. The filtrate was concentrated in vacuo and the residue was purified by silica gel chromatography (chloroform/methanol 20/1) and crystallized from ethyl acetate/hexane to give the titled compound (45 mg, 18%).

$^1$H NMR ($CDCl_3$, 400 MHz) δ 8.09 (d, 1H, J=8.6 Hz), 7.62 (s, 1H), 7.61 (s, 1H), 7.41 (dd, 1H, J=2.1 and 8.6 Hz), 7.26 (d, 1H, J=2.1 Hz), 4.85-4.81 (m, 1H), 4.25-4.21 (m, 1H), 3.35-2.87 (m, 8H), 1.29 (br, 6H).

Example 18-2

3-(2,4-dichlorophenyl)-1-[trans-3-(diethylamino)-cyclobutyl]-4-trifluoromethyl-3-hydroxy-2-oxoindoline-6-carboxamide hydrochloride

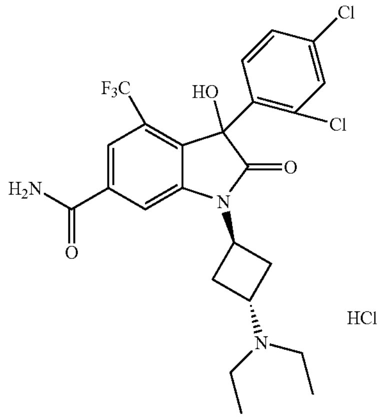

The compound of Example 18-1 was treated in a similar manner to Example 1-3 to Example 1-4 to give the titled compound.

$^1$H NMR (DMSO-$d_6$, 400 MHz) δ 10.61 (br, 1H), 8.36 (s, 1H), 8.08 (d, 1 H, J=8.6 Hz), 7.87 (s, 1H), 7.85 (s, 1H), 7.76 (s, 1H), 7.60 (dd, 1H, J=2.1 and 8.6 Hz), 7.52 (d, 1H, J=2.1 Hz), 7.51 (s, 1H), 4.95-4.91 (m, 1H), 4.21-4.17 (m, 1H), 3.16-2.93 (m, 8H), 1.20-1.13 (m, 6 Hz).

Example 19

3-(2,4-dichlorophenyl)-1-[trans-3-(dicyclopropylmethylamino)-cyclobutylmethyl]-4-trifluoromethyl-3-hydroxy-6-(2-oxazolyl)-1,3-dihydro-2H-indol-2-one hydrochloride

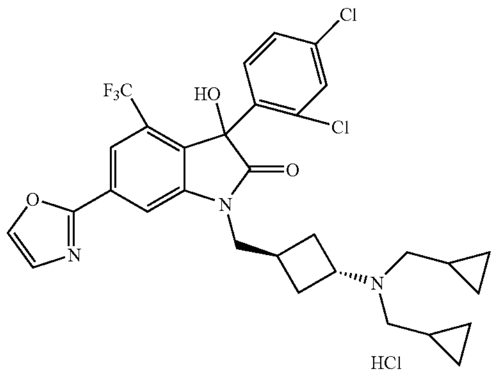

3-(2,4-dichlorophenyl)-1-[trans-3-(dicyclopropylamino)-cyclobutylmethyl]-4-trifluoromethyl-3-hydroxy-6-iodo-1,3-dihydro-2H-indol-2-one was treated in a similar manner to Example 14-2 to give 3-(2,4-dichlorophenyl)-1-[trans-3-(dicyclopropylmethylamino)-cyclobutylmethyl]-4-trifluoromethyl-3-hydroxy-6-(2-oxazolyl)-1,3-dihydro-2H-indol-2-one, and to a solution thereof in acetonitrile was added 4N hydrochloric acid water, and then the mixture was concentrated in vacuo and dried to give the titled compound.

$^1$H NMR (DMSO-$d_6$, 400 MHz) δ 10.05 (br, 1H), 8.36 (s, 1H), 8.08 (d, 1H, J=8.6 Hz), 8.02 (s, 1H), 7.83 (s, 1H), 7.60 (dd, 1H, J=2.1 and 8.6 Hz), 7.52-7.47 (m, 3H), 4.30-4.18 (m, 1H), 4.09 (d, 2H, J=7.8 Hz), 3.04-2.94 (m, 4H) 2.75-2.65 (m, 1H), 2.60-2.45 (m, 2H), 2.24-2.10 (m, 2H), 1.13-1.03 (m, 2H), 0.67-0.56 (m, 4H), 0.43-0.32 (m, 4H).

Example 20

3-(2,4-dichlorophenyl)-1-[trans-3-(diethylamino)-cyclobutylmethyl]-4-trifluoromethyl-3-hydroxy-2-oxoindoline-6-carboxamide Example 20-1

(trans-3-di-n-propylaminocyclobutyl)-methanol

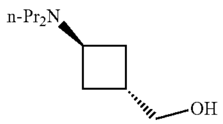

3-cis-methanesulfonyloxycyclobutane carboxylic benzyl ester and propionaldehyde were treated in a similar manner to Example 1-2 to 1-3 to give the titled compound.

$^1$H NMR ($CDCl_3$, 400 MHz) δ 3.68 (d, 2H, J=7.4 Hz), 3.20 (m, 1H), 2.35 (m, 5H), 2.08 (br, 2H), 1.89 (m, 2H), 1.44 (m, 4H), 0.86 (t, 6H, J=7.4 Hz).

Example 20-2

3-(2,4-dichlorophenyl)-1-[trans-3-(di-n-propylamino)-cyclobutylmethyl]-4-trifluoromethyl-3-hydroxy-2-oxoindoline-6-carboxamide

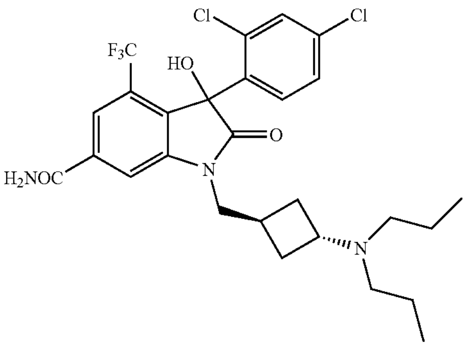

The compound of Example 20-1 was treated in a similar manner to Example 3-3 to 3-5 without the HCl salt forming step to give the titled compound.

LC-MS m/z 572 (M+H$^+$).

$^1$H NMR ($CDCl_3$, 400 MHz) δ 8.05 (d, 1H, J=8.5 Hz), 7.62 (s, 1H), 7.62 (d, 1H, J=8.5 Hz), 7.41 (dd, 1H, J=2, 8.5 Hz), 7.27 (s, 1H), 6.46 (br, 1H), 5.87 (br, 1H), 3.99 (dd, 1H, J=8.4, 14.2 Hz), 3.91 (dd, 1H, J=8.4, 14.2 Hz), 3.41 (m, 1H), 2.67 (m, 1H), 2.36 (m, 4H), 2.16-1.92 (br, 4H), 1.42 (m, 4H), 0.85 (t, 6H, J=7.3 Hz).

Example 21

3-(2,4-dichlorophenyl)-1-[trans-3-(dicyclobutylamino)-cyclobutylmethyl]-4-trifluoromethyl-3-hydroxy-2-oxoindoline-6-carboxamide

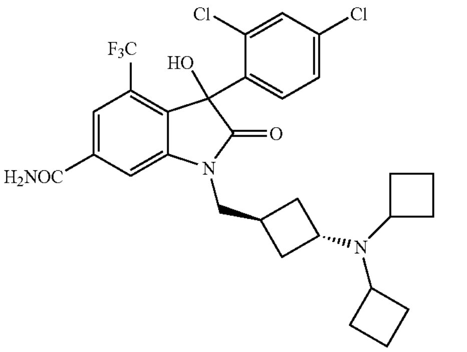

Cyclobutanone was treated as an alternative to propionaldehyde in a similar manner to Example 20-1 to 20-2 to give the titled compound.

LC-MS m/z 596 (M+H$^+$).

$^1$H NMR ($CDCl_3$, 400 MHz) δ 8.06 (d, 1H, J=8.5 Hz), 7.68 (s, 1H), 7.63 (s, 1H), 7.42 (dd, 1H, J=2, 8.5 Hz), 7.26 (d, 1H, J=2 Hz), 6.66 (br, 1H), 5.79 (br, 1H), 3.97 (d, 2H, J=8.2 Hz), 3.55 (m, 1H), 3.12 (m, 2H), 2.65 (m, 1H), 2.42 (br, 2H), 2.21 (br, 4H), 2.00 (m, 7H), 1.6 (m, 5H).

Example 22

3-(2,4-dichlorophenyl)-1-[trans-3-(dimethylamino)-cyclobutylmethyl]4-trifluoromethyl-3-hydroxy-2-oxoindoline-6-carboxamide hydrochloride

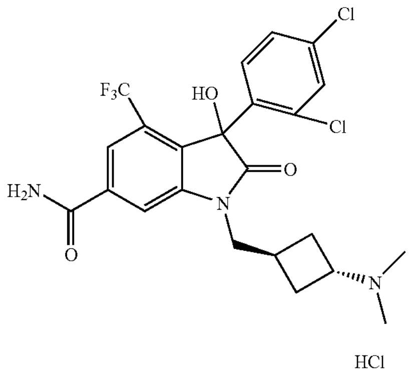

Formamide was treated as an alternative to propionaldehyde in a similar manner to Example 20-1 to 20-2 to give the titled compound.

$^1$H NMR (DMSO-$d_6$, 400 MHz) δ 10.49 (br, 1H), 8.36 (s, 1H), 8.08 (d, 1H, J=8.6 Hz), 7.93 (s, 1H), 7.83 (s, 1H), 7.76 (s, 1H), 7.59 (dd, 1H, J=2.1 and 8.6 Hz), 7.50 (d, 1H, J=2.1 Hz), 7.46 (s, 1H), 4.05-3.90 (m, 3H), 2.76-2.61 (m, 1H), 2.52 (s, 6H), 2.44-2.35 (m, 2H), 2.19-2.12 (m, 2H).

The compound of Example 23-31 was obtained according to the above method.

Example 23

3-(2,6-difluorophenyl)-1-[trans-3-(diethylamino)-cyclobutylmethyl]-4-trifluoromethyl-3-hydroxy-2-oxoindoline-6-carboxamide hydrochloride

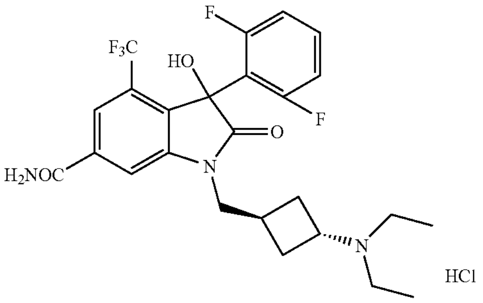

$^1$H NMR (DMSO-$d_6$, 400 MHz) δ 9.61 (brs, 1H), 8.30 (s, 1H), 7.92 (s, 1H), 7.82 (s, 1H), 7.77 (m, 1H), 7.40 (m, 1H), 7.23 (m, 1H), 7.18 (m, 1H), 7.02 (m, 2H), 4.16-3.90 (m, 3H), 3.13-3.02 (m, 2H), 3.02-2.92 (m, 2H), 2.73-2.64 (m, 1H), 2.35-2.45 (m, 2H), 2.18-2.08 (m, 2H), 1.15 (m, 6H).

Example 24

3-(2,6-difluorophenyl)-1-[trans-3-(dicyclopropylamino)-cyclobutylmethyl]-4-trifluoromethyl-3-hydroxy-2-oxoindoline-6-carboxamide hydrochloride

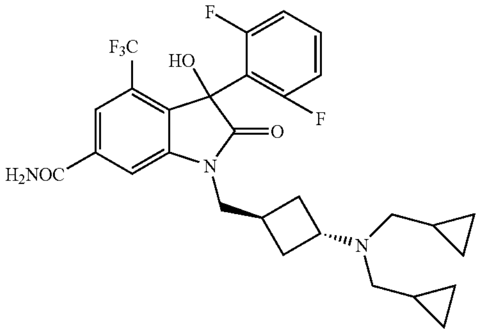

HCl

$^1$H NMR (DMSO-$d_6$, 400 MHz) δ 9.59 (brs, 1H), 8.30 (s, 1H), 7.94 (s, 1H), 7.82 (s, 1H), 7.77 (s, 1H), 7.40 (m, 1H), 7.23 (m, 1H), 7.18 (m, 1H), 7.02 (m, 2H), 4.20 (m, 1H), 4.01-3.92 (m, 2H), 3.28 (m, 4H), 3.01 (m, 1H), 2.35-2.45 (m, 2H), 2.18-2.08 (m, 2H), 1.16 (m, 2H), 0.63 (m, 4H), 0.38 (m, 4H).

Example 25

3-(2,4,6-trifluorophenyl)-1-[trans-3-(dicyclopropylamino)-cyclobutylmethyl]-4-trifluoromethyl-3-hydroxy-2-oxoindoline-6-carboxamide hydrochloride

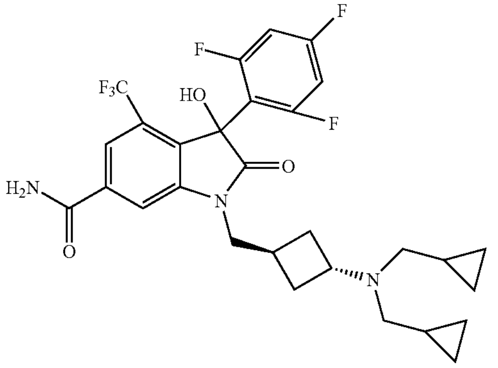

HCl

$^1$H NMR (DMSO-$d_6$, 400 MHz) δ 10.08 (br, 1H), 8.35 (s, 1H), 8.00 (s, 1H), 7.84 (s, 1H), 7.77 (s, 1H), 7.18-7.15 (m, 3H), 4.25-4.21 (m, 1H), 4.02-3.96 (m, 2H), 3.01-2.94 (m, 4H), 2.71-2.68 (m, 1H), 2.56-2.50 (m, 2H), 2.14-2.12 (m, 2H), 1.09-1.04 (m, 2H), 0.65-0.58 (m, 4H), 0.39-0.38 (m, 4H).

Example 26

3-(2-chloro-6-fluorophenyl)-1-[trans-3-(dicyclopropylamino)-cyclobutylmethyl]-4-trifluoromethyl-3-hydroxy-2-oxoindoline-6-carboxamide hydrochloride

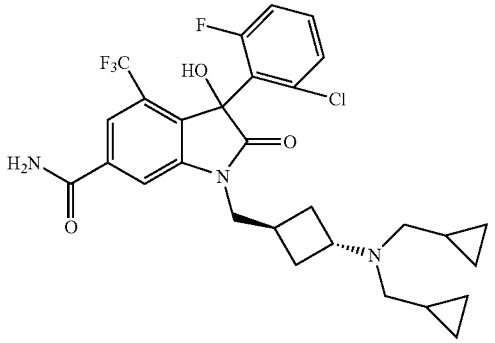

HCl

$^1$H NMR (DMSO-$d_6$, 400 MHz) δ 10.25 (br, 1H), 8.43 (s, 1H), 8.06 (s, 1H), 7.88 (s, 1H), 7.81 (s, 1H), 7.49-7.10 (m, 4H), 4.34-4.26 (m, 1H), 4.08-4.05 (m, 2H), 3.05-3.04 (m, 4H), 2.78-2.75 (m, 1H), 2.61-2.55 (m, 2H), 2.26-2.18 (m, 2H), 1.17-1.11 (m, 2H), 0.71-0.66 (m, 4H), 0.47-0.44 (m, 4H).

Example 27

3-(2-chloro-6-fluorophenyl)-1-[trans-3-(diethylamino)-cyclobutylmethyl]-4-trifluoromethyl-3-hydroxy-2-oxoindoline-6-carboxamide Hydrochloride

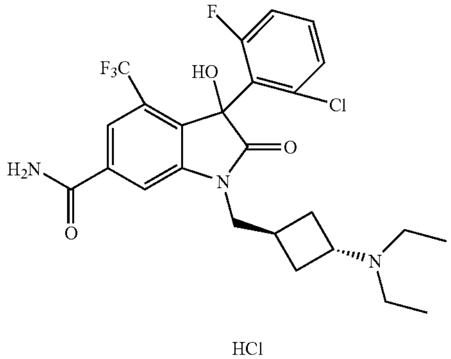

HCl

$^1$H NMR (DMSO-$d_6$, 400 MHz) δ 10.35 (br, 1H), 8.42 (s, 1H), 8.03 (s, 1H), 7.88 (s, 1H), 7.81 (s, 1H), 7.49-7.24 (m, 3H), 7.18 (s, 1H), 4.22-4.18 (m, 1H), 4.09-4.04 (m, 2H), 3.14-2.99 (m, 4H), 2.78-2.74 (m, 1H), 2.58-2.52 (m, 2H), 2.19-2.13 (m, 2H), 1.16 (t, 6H, J=6.1 Hz).

Example 28

3-(2,6-difluorophenyl)-1-[trans-3-(diethylamino)-cyclobutylmethyl]-4-trifluoromethyl-3-hydroxy-6-(2-oxazolyl)-1,3-dihydro-2H-indol-2-one hydrochloride

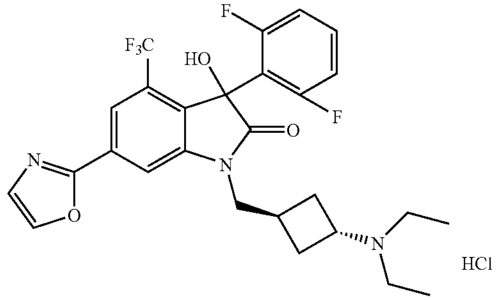

$^1$H NMR (DMSO-$d_6$, 400 MHz) δ 9.98 (brs, 1H), 8.38 (s, 1H), 8.01 (s, 1H), 7.83 (s, 1H), 7.50 (s, 1H), 7.40 (m, 1H), 7.13 (s, 1H), 7.02 (m, 2H), 4.16-4.05 (m, 3H), 3.10-3.02 (m, 2H), 3.02-2.90 (m, 2H), 2.73-2.64 (m, 1H), 2.45-2.50 (m, 2H), 2.18-2.08 (m, 2H), 1.16 (m, 6H).

Example 29

3-(2,6-difluorophenyl)-1-[trans-3-(dicyclopropylmethylamino)-cyclobutylmethyl]-4-trifluoromethyl-3-hydroxy-6-(2-oxazolyl)-1,3-dihydro-2H-indol-2-one hydrochloride

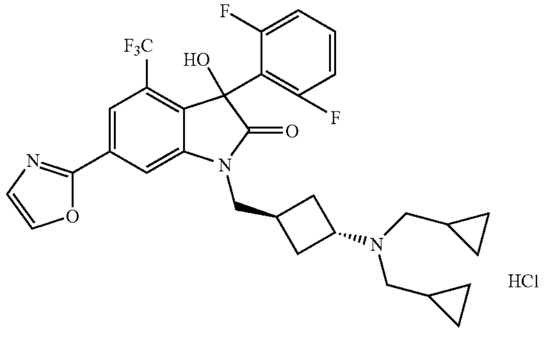

$^1$H NMR (DMSO-$d_6$, 400 MHz) δ 9.79 (brs, 1H), 8.38 (s, 1H), 8.03 (s, 1H), 7.84 (s, 1H), 7.50 (s, 1H), 7.41 (m, 1H), 7.13 (s, 1H), 7.03 (m, 2H), 4.21 (m, 1H), 4.08 (d, 2H, J=7.5 Hz), 3.00 (m, 4H), 2.71 (m, 1H), 2.35-2.45 (m, 2H), 2.10-2.20 (m, 2H), 1.10-1.00 (m, 2H), 0.63 (m, 4H), 0.38 (m, 4H).

Example 30

3-(2,4,6-trifluorophenyl)-1-[trans-3-(diethylamino)-cyclobutylmethyl]-4-trifluoromethyl-3-hydroxy-6-(2-oxazolyl)-1,3-dihydro-2H-indol-2-one hydrochloride

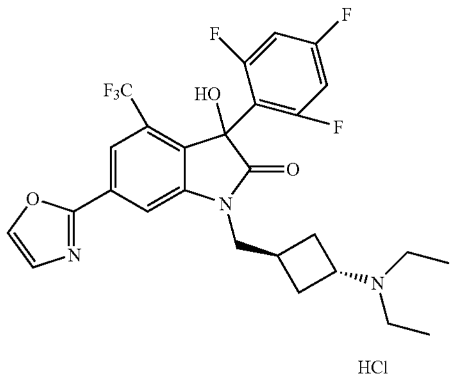

$^1$H NMR (DMSO-$d_6$, 400 MHz) δ 10.37 (br, 1H), 8.36 (s, 1H), 8.03 (s, 1H), 7.85 (s, 1H), 7.50 (d, 1H, J=0.53), 7.22 (s, 1H), 7.20-7.12 (m, 2H), 4.15-4.00 (m, 3H), 3.15-2.85 (m, 4H) 2.95-2.63 (m, 1H), 2.58-2.43 (m, 2H), 2.18-2.05 (m, 2H), 1.30-1.08 (m, 6H).

Example 31

3-(2,4,6-trifluorophenyl)-1-[trans-3-(dicyclopropylmethylamino)-cyclobutylmethyl]-4-trifluoromethyl-3-hydroxy-6-(2-oxazolyl)-1,3-dihydro-2H-indol-2-one hydrochloride

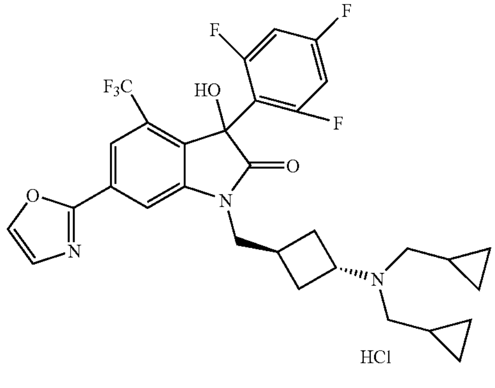

$^1$H NMR (DMSO-$d_6$, 400 MHz) δ 9.80 (br, 1H), 8.36 (d, 1H, J=0.68 Hz), 8.04 (s, 1H), 7.85 (s, 1H), 7.51 (d, 1H, J=0.68 Hz), 7.21 (s, 1H), 7.22-7.13 (m, 2H), 4.26-4.19 (m, 1H), 4.07 (d, 2H, J=7.9 Hz), 3.15-2.92 (m, 4H) 2.75-2.65 (m, 1H), 2.55-2.43 (m, 2H), 2.22-2.08 (m, 2H), 1.13-1.02 (m, 2H), 0.67-0.56 (m, 4H), 0.43-0.32 (m, 4H).

Example 32

3-(2-chloro-6-fluorophenyl)-1-[trans-3-(diethylamino)-cyclobutylmethyl]-4-trifluoromethyl-3-hydroxy-6-methylsulfonyl-1,3-dihydro-2H-indol-2-one

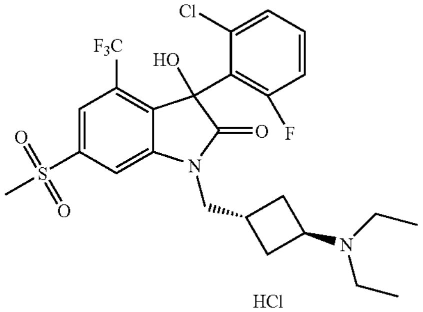

HCl

Example 32-1

Synthesis of 3-(2-chloro-6-fluorophenyl)-1-[trans-3-(diethylamino)-cyclobutylmethyl]-4-trifluoromethyl-3-hydroxy-6-methylthio-1,3-dihydro-2H-indol-2-one To a solution of 3-(2-chloro-6-fluorophenyl)-1-[trans-3-(diethylamino)-cyclobutylmethyl]-4-trifluoromethyl-3-triethylsilyloxy-6-iodo-1,3-dihydro-2H-indol-2-one (200 mg, 0.276 mmol) in toluene (1.0 mL) were added sodium thiomethoxide (193 mg, 2.76 mmol), 1,10-phenanthroline (5 mg, 0.028 mmol) and copper iodide (5 mg, 0.028 mmol), and the mixture was stirred at 100° C. for 3 hours. To the reaction solution was added water, and the mixture was extracted with ethyl acetate, dried over anhydrous magnesium sulfate, and then filtered, concentrated and purified by silica gel column chromatography (chloroform/methanol=10/1). To a solution of the resulting oil in tetrahydrofuran (1 mL) was added tetrabutylammonium fluoride (excess amount). The mixture was stirred at room temperature for 3 hours, and then the reaction solution was concentrated and purified by silica gel column chromatography (chloroform/methanol=10/1) to give the titled compound (122 mg) as a colorless oil.

Example 32-2

Synthesis of 3-(2-chloro-6-fluorophenyl)-1-[trans-3-(diethylamino) cyclobutylmethyl]-4-trifluoromethyl-3-hydroxy-6-methylsulfonyl-1,3-dihydro-2H-indol-2-one To a solution of the compound of Example 32-1 (70 mg) in acetic acid (1 mL) were added sodium tungstate dihydrate (39 mg, 0.118 mmol) and 30% aqueous hydrogen peroxide (0.1 mL), and the mixture was stirred at room temperature for 2 hours. To the reaction solution was added aqueous sodium thiosulfate solution, and the mixture was extracted with ethyl acetate and washed with saturated saline, and the organic layer was dried over magnesium sulfate and filtered, and then the filtrate was evaporated and purified by silica gel column chromatography (chloroform/methanol=20/1 to 10/1) followed by hydrochloride salt formation to give the titled compound (29 mg, 31%).

$^1$H NMR (DMSO-$d_6$, 400 MHz) δ 10.48 (br, 1H), 8.08 (s, 1H), 7.79 (s, 1H), 7.42 (m, 1H), 7.35 (m, 2H), 7.21 (m, 1H), 4.15-4.05 (m, 3H), 3.42 (s, 3H), 3.08-2.90 (m, 4H), 2.72-2.65 (m, 1H), 2.58-2.45 (m, 2H), 2.20-2.05 (m, 2H), 1.17 (t, 6H, J 7.0 Hz).

The compounds of Example 33 to 97 were synthesized in a similar manner to Example 14, Example 15 or Example 16.

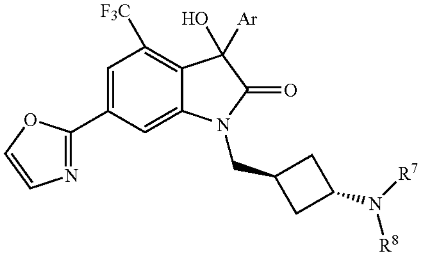

HCl

| No. | Ar | $—NR^7R^8$ |
|---|---|---|
| 33 | 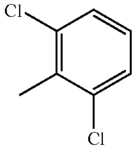 | 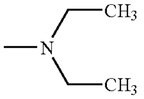 |
| 34 | 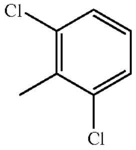 | 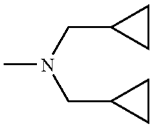 |
| 35 | 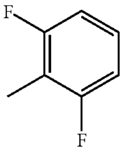 | 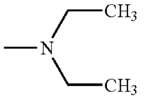 |
| 36 | 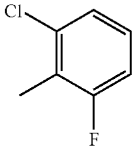 | 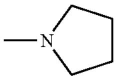 |
| 37 | 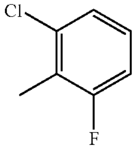 | 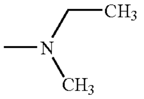 |
| 38 | 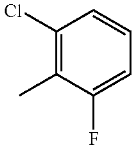 | 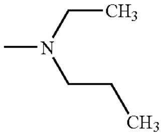 |
| 39 | 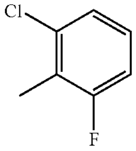 | 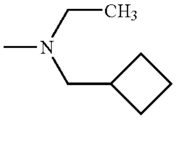 |

-continued
| | | |
|---|---|---|
| 40 | 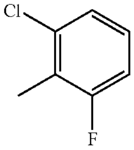 | 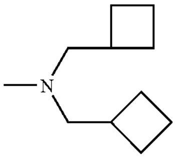 |
| 41 | 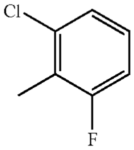 | 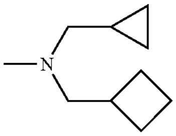 |
| 42 | 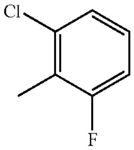 | 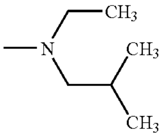 |
| 43 | 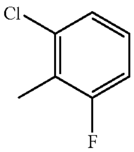 | 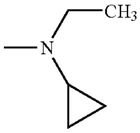 |
| 44 | 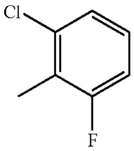 | 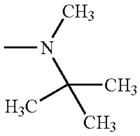 |
| 45 | 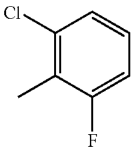 | 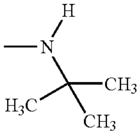 |
| 46 | 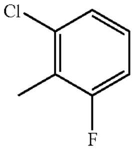 | 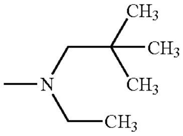 |
| 47 | 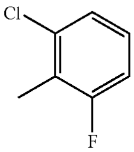 | 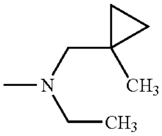 |
| 48 | 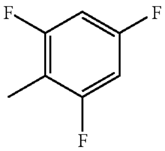 | 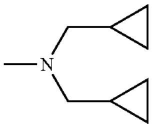 |
-continued
| | | |
|---|---|---|
| 49 | 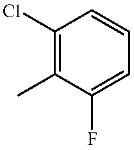 | 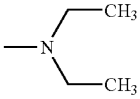 |
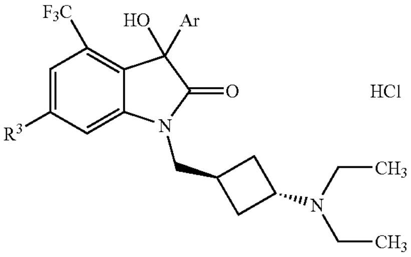
HCl
| No. | Ar | —$NR^7R^8$ |
|---|---|---|
| 50 | 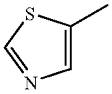 | 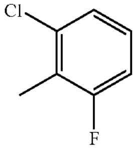 |
| 51 | 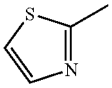 | 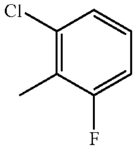 |
| 52 | 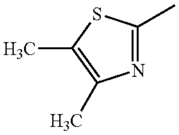 | 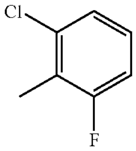 |
| 53 | 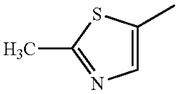 | 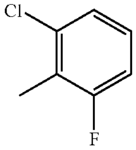 |
| 54 | 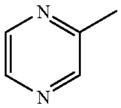 | 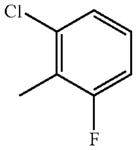 |
| 55 | 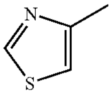 | 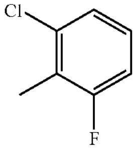 |
| 56 | 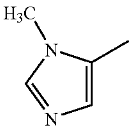 | 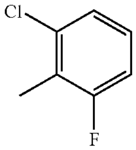 |

-continued
57 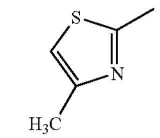 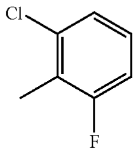
58 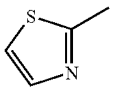 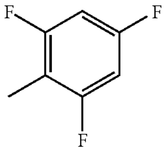
59 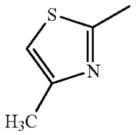 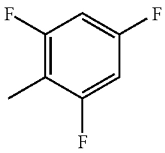
60 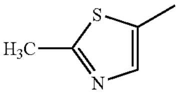 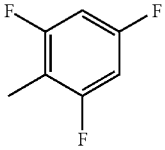
61 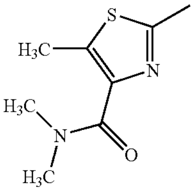 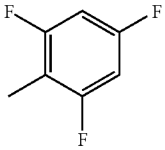
62 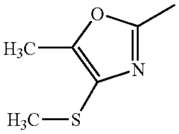 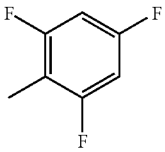
63 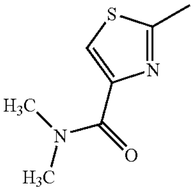 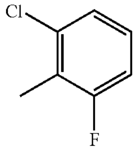
64 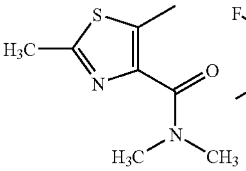 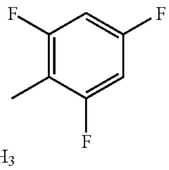
65 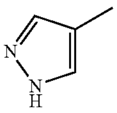 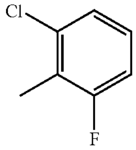
-continued
66 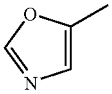 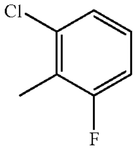
67 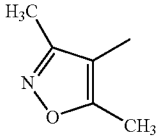 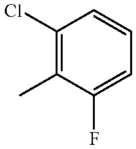
68 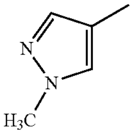 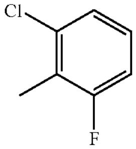
69 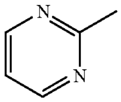 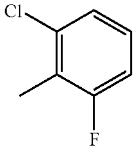
70 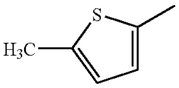 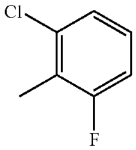
71 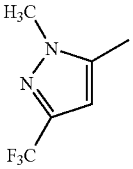 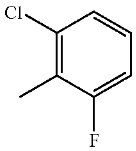
72 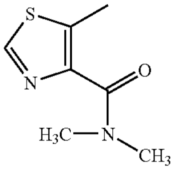 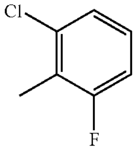
73 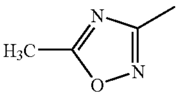 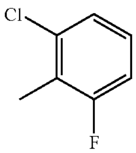
74 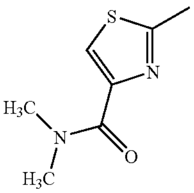 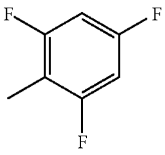

-continued

| | | |
|---|---|---|
| 75 | 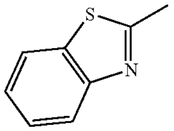 | 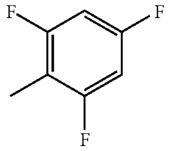 |
| 76 | 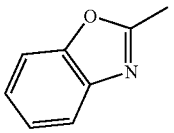 | 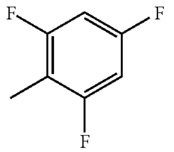 |
| 77 | 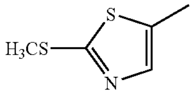 | 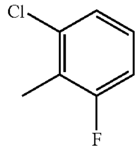 |
| 78 | 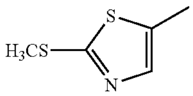 | 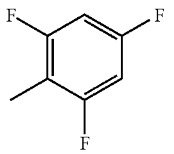 |
| 79 | 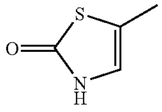 | 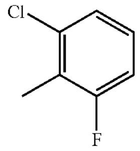 |
| 80 | 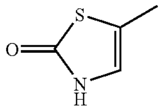 | 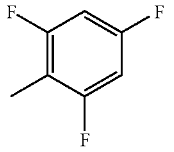 |
| 81 | 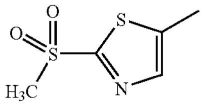 | 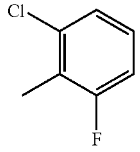 |
| 82 | 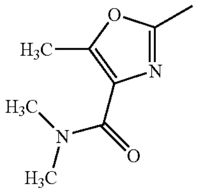 | 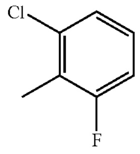 |
| 83 | 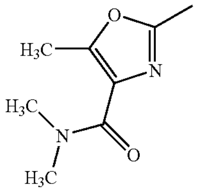 | 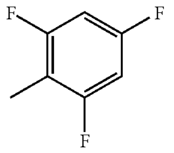 |

Example 33

$^1$H NMR (DMSO-$d_6$, 400 MHz) δ 10.02 (br, 1H), 8.37 (s, 1H), 7.99 (s, 1H), 7.81 (s, 1H), 7.52 (t, 1H, J=5.2 Hz), 7.51 (s, 1H), 7.34 (d, 2H, J=5.2 Hz), 7.28 (s, 1H), 4.15-4.05 (m, 3H), 3.10-2.90 (m, 4H), 2.75-2.62 (m, 1H), 2.50-2.41 (m, 2H), 2.20-2.09 (m, 2H), 1.17 (t, 6H, J=7.0 Hz)

Example 34

$^1$H NMR (DMSO-$d_6$, 400 MHz) δ 9.93 (br, 1H), 8.37 (s, 1H), 8.01 (s, 1H), 7.81 (s, 1H), 7.52 (t, 1H, J=5.2 Hz, 7.51 (s, 1H), 7.34 (d, 2H, J=5.2 Hz, 7.28 (s, 1H), 4.28-4.05 (m, 3H), 3.05-2.95 (m, 4H), 2.75-2.65 (m, 1H), 2.50-2.45 (m, 2H), 2.25-2.12 (m, 2H), 1.10-1.03 (m, 2H), 0.67-0.58 (m, 4H), 0.40-0.34 (m, 4H)

Example 35

$^1$H NMR (DMSO-$d_6$, 400 MHz) δ 10.01 (br, 1H), 8.37 (s, 1H), 8.02 (s, 1H), 7.82 (s, 1H), 7.51 (s, 1H), 7.44-7.18 (m, 1H), 7.13 (s, 1H), 7.09-7.00 (m, 2H), 4.16-4.05 (m, 3H), 3.12-2.90 (m, 4H), 2.74-2.64 (m, 1H), 2.50-2.39 (m, 2H), 2.18-2.08 (m, 2H), 1.16 (t, 6H, J=7.2 Hz)

Example 36

$^1$H NMR (DMSO-$d_6$, 400 MHz) δ 11.24 (br, 1H), 8.37 (s, 1H), 7.99 (s, 1H), 7.83 (s, 1H), 7.50 (s, 1H), 7.45-7.16 (m, 4H), 4.07-3.90 (m, 3H), 3.45-3.35 (m, 2H), 2.92-2.78 (m, 3H), 2.48-2.36 (m, 2H), 2.26-2.11 (m, 2H), 2.02-1.80 (m, 4H)

Example 37

$^1$H NMR (DMSO-$d_6$, 400 MHz) δ 10.59 (br, 1H), 8.36 (s, 1H), 7.98 (s, 1H), 7.83 (s, 1H), 7.48 (s, 1H), 7.42-7.01 (m, 4H), 4.13-3.89 (m, 3H), 3.15-3.02 (m, 1H), 2.90-2.80 (m, 1H), 2.78-2.62 (m, 1H), 2.57 (s, 3H), 2.50-2.40 (m, 2H), 2.23-2.05 (m, 2H), 1.18 (t, 3H, J=7.2 Hz)

Example 38

$^1$H NMR (DMSO-$d_6$, 400 MHz) δ 10.46 (br, 1H), 8.33 (s, 1H), 8.02 (s, 1H), 7.82 (s, 1H), 7.50 (s, 1H), 7.45-7.12 (m, 4H), 4.16-4.05 (m, 3H), 3.10-2.80 (m, 5H), 2.73-2.64 (m, 1H), 2.58-2.48 (m, 1H), 2.23-2.07 (m, 2H), 1.67-1.58 (m, 2H), 1.19-1.12 (m, 3H), 0.90 ft, 3H, J=7.3 Hz

Example 39

LC-MS m/z 592 ($M+H^+$)

Example 40

$^1$H NMR (DMSO-$d_6$, 400 MHz) δ 10.59 (br, 1H), 8.36 (s, 1H), 8.00 (s, 1H), 7.83 (s, 1H), 7.50 (s, 1H), 7.43-7.13 (m, 4H), 4.12-4.00 (m, 3H), 2.92-2.78 (m, 4H), 2.66-2.48 (m, 6H), 2.22-2.20 (m, 5H), 1.90-1.70 (m, 5H), 1.20-1.14 (m, 3H)

Example 41

$^1$H NMR (DMSO-$d_6$, 400 MHz) δ 10.20 (br, 1H), 8.36 (s, 1H), 8.01 (s, 1H), 7.83 (s, 1H), 7.51 (s, 1H), 7.48-7.16 (m, 4H), 4.13-4.05 (m, 3H), 3.12-3.07 (m, 2H), 2.88-2.80 (m, 2H), 2.75-2.64 (m, 2H), 2.58-2.49 (m, 2H), 2.24-2.00 (m, 4H), 1.90-1.69 (m, 4H), 1.01 (m, 1H), 0.64-0.57 (m, 2H), 0.39-0.32 (m, 2H)

Example 42

$^1$H NMR (DMSO-$d_6$, 400 MHz) δ 10.11 (br, 1H), 8.37 (s, 1H), 8.00 (s, 1H), 7.83 (s, 1H), 7.51 (s, 1H), 7.46-7.13 (m, 4H), 4.16-4.05 (m, 3H), 3.12-2.96 (m, 2H), 2.87-2.78 (m, 1H), 2.78-2.65 (m, 3H), 2.58-2.55 (m, 1H), 2.28-1.90 (m, 3H), 1.16 (t, 3H, J=7.2 Hz), 1.01 (d, 3H, J=8 Hz), 0.97 (d, 3H, J=8 Hz)

Example 43

$^1$H NMR (DMSO-$d_6$, 400 MHz) δ 10.70 (br, 1H), 8.36 (s, 1H), 7.99 (m, 1H), 7.83 (s, 1H), 7.50 (s, 1H), 7.42-7.16 (m, 4H), 4.36-4.22 (m, 1H), 4.13-4.05 (m, 2H), 3.16-2.97 (m, 2H), 2.77-2.53 (m, 4H), 2.28-2.05 (m, 2H), 1.26 (t, 3H, J=7.2 Hz), 1.25-1.16 (m, 1H), 0.96-0.87 (m, 1H), 0.86-0.73 (m, 2H)

Example 44

$^1$H NMR (DMSO-$d_6$, 400 MHz) δ 10.07 (br, 1H), 8.37 (s, 1H), 8.02 (s, 1H), 7.83 (s, 1H), 7.51 (s, 1H), 7.42-7.18 (m, 4H), 4.49-4.30 (m, 1H), 4.17-4.05 (m, 2H), 2.75-2.65 (m, 2H), 2.55 (br, 3H), 2.50-2.33 (m, 1H), 2.28-2.09 (m, 2H), 1.31 (s, 6H), 1.29 (s, 3H)

Example 45

$^1$H NMR (DMSO-$d_6$, 400 MHz) δ 8.78 (br, 2H), 8.36 (s, 1H), 7.99 (s, 1H), 7.83 (s, 1H), 7.51 (s, 1H), 7.46-7.18 (m, 4H), 4.25-4.08 (m, 3H), 2.82-2.75 (m, 1H), 2.50-2.35 (m, 2H), 2.28-2.11 (m, 2H), 1.25 (s, 9H)

Example 46

$^1$H NMR (DMSO-$d_6$, 400 MHz) δ 9.52 (br, 1H), 3.37 (s, 1H), 8.01 (s, 1H), 7.83 (s, 1H), 7.50 (s, 1H), 7.42-7.16 (m, 4H), 4.19-4.05 (m, 3H), 3.22-3.13 (m, 1H), 3.10-2.96 (m, 2H), 2.84-2.60 (m, 3H), 2.50-2.38 (m, 1H), 2.30-2.15 (m, 1H), 2.15-1.97 (m, 1H), 1.21 (t, 3H, J=7.2 Hz), 1.07 (s, 9H)

Example 47

$^1$H NMR (DMSO-$d_6$, 400 MHz) δ 9.24 (br, 1H), 8.37 (s, 1H), 7.98 (s, 1H), 7.83 (s, 1H), 7.51 (s, 1H), 7.46-7.17 (m, 4H), 4.13-4.03 (m, 3H), 3.20-3.12 (m, 2H), 3.18-2.95 (m, 1H), 2.90-2.79 (m, 1H), 2.79-2.64 (m, 1H), 2.60-2.40 (m, 2H), 2.28-2.04 (m, 2H), 1.20-1.14 (m, 3H), 1.16 (s, 3H), 0.66-0.37 (m, 4H)

Example 48

$^1$H NMR (DMSO-$d_6$, 400 MHz) δ 9.80 (br, 1H), 8.36 (d, 1H, J=0.68 Hz), 8.04 (s, 1H), 7.85 (s, 1H), 7.51 (d, 1H, J=0.68 Hz), 7.21 (s, 1H), 7.22-7.13 (m, 2H), 4.26-4.19 (m, 1H), 4.07 (d, 2H, J=7.9 Hz), 3.15-2.92 (m, 4H) 2.75-2.65 (m, 1H), 2.55-2.43 (m, 2H), 2.22-2.08 (m, 2H), 1.13-1.02 (m, 2H), 0.67-0.56 (m, 4H), 0.43-0.32 (m, 4H)

Example 49

$^1$H NMR (DMSO-$d_6$, 400 MHz) δ 10.09 (br, 1H), 8.34 (s, 1H), 7.97 (s, 1H), 7.81 (s, 1H), 7.48 (s, 1H), 7.42-7.16 (m, 4H), 4.11-4.05 (m, 3H), 3.05-2.90 (m, 4H), 2.71-2.64 (m, 1H), 2.48-2.41 (m, 2H), 2.16-2.09 (m, 2H), 1.12 (t, 6H, J=7.2 Hz)

Example 50

$^1$H NMR (DMSO-$d_6$, 400 MHz) δ 10.37 (br, 1H), 9.21 (s, 1H), 8.61 (s, 1H), 7.86 (s, 1H), 7.50 (s, 1H), 7.46-6.98 (m, 4H), 4.20-4.00 (m, 3H), 3.12-2.90 (m, 4H), 2.78-2.65 (m, 1H), 2.58-2.45 (m, 2H), 2.23-2.08 (m, 2H), 1.18-1.11 (m, 6H)

Example 51

$^1$H NMR (DMSO-$d_6$, 400 MHz) δ 10.37 (br, 1H), 8.03 (d, 1H, J=3.2 Hz), 7.99 (s, 1H), 7.97 (d, 1H, J=3.2 Hz), 7.81 (s, 1H), 7.44-7.01 (m, 4H), 4.20-4.00 (m, 3H), 3.12-2.88 (m, 4H), 2.78-2.65 (m, 1H), 2.58-2.42 (m, 2H), 2.26-2.05 (m, 2H), 1.19-1.11 (m, 6H)

Example 52

$^1$H NMR (DMSO-$d_6$, 400 MHz) δ 10.54 (br, 1H), 7.82 (s, 1H), 7.68 (s, 1H), 7.45-7.02 (m, 4H), 4.18-4.00 (m, 3H), 3.10-2.87 (m, 4H), 2.75-2.64 (m, 1H), 2.59-2.48 (m, 2H), 2.43 (s, 3H), 2.36 (s, 3H), 2.22-2.02 (m, 2H), 1.19-1.10 (m, 6H)

Example 53

$^1$H NMR (DMSO-$d_6$, 400 MHz) δ 10.58 (br, 1H), 8.36 (s, 1H), 7.80 (s, 1H), 7.39 (s, 1H), 7.42-7.02 (m, 4H), 4.15-3.96 (m, 3H), 3.12-2.87 (m, 4H), 2.77-2.65 (m, 1H), 2.59-2.45 (m, 2H), 2.27 (s, 3H), 2.28-2.02 (m, 2H), 1.18-1.08 (m, 6H)

Example 54

$^1$H NMR (DMSO-$d_6$, 400 MHz) δ 10.37 (br, 1H), 9.52 (s, 1H), 8.83-8.76 (m, 1H), 8.73 (d, 1H, J=2.5 Hz), 8.22 (s, 1H), 8.08 (s, 1H), 7.73-7.00 (m, 4H), 4.18-3.92 (m, 3H), 3.10-2.85 (m, 4H), 2.81-2.69 (m, 1H), 2.51-2.40 (m, 2H), 2.28-2.02 (m, 2H), 1.18-1.11 (m, 6H)

Example 55

$^1$H NMR (DMSO-$d_6$, 400 MHz) δ 10.14 (br, 1H), 9.27 (d, 1H, J=1.8 Hz), 8.60 (d, 1H, J=1.8 Hz, 8.06 (s, 1H), 7.95 (s, 1H), 7.45-7.12 (m, 3H), 7.06 (br, 1H), 4.19-4.02 (m, 3H), 3.12-2.88 (m, 4H), 2.79-2.65 (m, 1H), 2.58-2.41 (m, 2H), 2.26-2.05 (m, 2H), 1.18-1.10 (m, 6H)

Example 56

$^1$H NMR (DMSO-$d_6$, 400 MHz) δ 10.69 (br, 1H), 8.73 (br, 1H), 7.78 (s, 1H), 7.76 (s, 1H), 7.46 (s, 1H), 7.45-7.03 (m, 4H), 7.18 (s, 1H), 4.16-3.97 (m, 3H), 3.86 (s, 3H), 3.09-2.82 (m, 4H), 2.72-2.59 (m, 1H), 2.59-2.51 (m, 2H), 2.19-2.02 (m, 2H), 1.18-1.08 (m, 6H)

Example 57

$^1$H NMR (DMSO-$d_6$, 400 MHz) δ 10.52 (br, 1H), 7.92 (s, 1H), 7.77 (s, 1H), 7.52 (s, 1H), 7.45-7.07 (m, 4H), 4.14-4.08 (m, 3H), 3.05-2.92 (m, 4H), 2.77-2.69 (m, 1H), 2.54-2.48 (m, 2H), 2.47 (s, 3H), 2.21-2.08 (m, 2H), 1.18-1.11 (m, 6H)

Example 58

$^1$H NMR (DMSO-$d_6$, 400 MHz) δ 10.44 (hr, 1H), 8.03 (d, 1H, J=3.2 Hz), 8.02 (s, 1H), 7.98 (d, 1H, J=3.2 Hz), 7.83 (s, 1H), 7.25-7.08 (m, 3H), 4.16-4.04 (m, 3H), 3.12-2.86 (m, 4H), 2.75-2.63 (m, 1H), 2.58-2.42 (m, 2H), 2.18-2.03 (m, 2H), 1.15 (t, 6H, J=7.0 Hz)

Example 59

$^1$H NMR (DMSO-$d_6$, 400 MHz) δ 10.56 (br, 1H), 7.94 (s, 1H), 7.79 (s, 1H), 7.52 (s, 1H), 7.17 (m, 3H), 4.20-3.95 (m,

3H), 3.18-2.82 (m, 4H), 2.73-2.62 (m, 1H), 2.59-2.45 (m, 2H), 2.47 (s, 3H), 2.16-2.04 (m, 2H), 1.19-1.10 (m, 6H)

Example 60

$^1$H NMR (DMSO-$d_6$, 400 MHz) δ 10.33 (br, 1H), 8.35 (s, 1H), 7.82 (s, 1H), 7.41 (s, 1H), 7.16 (m, 3H), 4.40-3.95 (m, 3H), 3.19-2.84 (m, 4H), 2.71 (s, 3H), 2.74-2.62 (m, 1H), 2.56-2.42 (m, 2H), 2.14-2.04 (m, 2H), 1.19-1.10 (m, 6H)

Example 61

$^1$H NMR (DMSO-$d_6$, 400 MHz) δ 9.95 (br, 1H), 7.96 (s, 1H), 7.81 (s, 1H), 7.23-7.08 (m, 3H), 4.18-4.07 (m, 3H), 3.12-2.88 (m, 4H), 3.02 (s, 6H), 2.72-2.63 (m, 1H), 2.50-2.39 (m, 2H), 2.43 (s, 3H), 2.18-2.05 (m, 2H), 1.15 (t, 6H, J=7.1 Hz)

Example 62

$^1$H NMR (DMSO-$d_6$, 400 MHz) δ 10.33 (br, 1H), 7.96 (s, 1H), 7.79 (s, 1H), 7.22 (s, 1H), 7.18 (t, 2H, J=9.9 Hz), 4.18-4.02 (m, 3H), 3.11-2.87 (m, 4H), 2.72-2.60 (m, 1H), 2.55-2.43 (m, 2H), 2.45 (s, 3H), 2.41 (s, 3H), 2.16-2.05 (m, 2H), 1.16 (t, 6H, J=7.2 Hz)

Example 63

$^1$H NMR (DMSO-$d_6$, 400 MHz) δ 10.23 (br, 1H), 8.25 (s, 1H), 7.98 (s, 1H), 7.83 (s, 1H), 7.44-7.15 (m, 4H), 4.13-4.09 (m, 3H), 3.14 (s, 3H), 3.10-2.96 (m, 7H), 2.73-2.67 (m, 1H), 2.49-2.44 (m, 2H), 2.20-2.12 (m, 2H), 1.18-1.14 (m, 6H).

Example 64

$^1$H NMR (DMSO-$d_6$, 400 MHz) δ 10.03 (br, 1H), 7.51 (s, 1H), 7.32 (s, 1H), 7.20-7.10 (m, 3H), 4.14-3.89 (m, 3H), 3.12-2.88 (m, 7H), 2.80 (s, 3H), 2.73 (s, 3H), 2.70-2.58 (m, 1H), 2.53-2.39 (m, 2H), 2.16-2.05 (m, 2H), 1.16 (t, 6H, J=7.0 Hz)

Example 65

$^1$H NMR (DMSO-$d_6$, 400 MHz) δ 10.03 (br, 1H), 8.34 (s, 2H), 7.75 (s, 1H), 7.52 (s, 1H), 7.45-7.17 (m, 4H), 4.17-4.12 (m, 1H), 4.03-4.01 (m, 2H), 3.07-2.93 (m, 4H), 2.76-2.70 (m, 1H), 2.49-2.41 (m, 2H), 2.20-2.08 (m, 2H), 1.19-1.13 (m, 6H)

Example 66

$^1$H NMR (DMSO-$d_6$, 400 MHz) δ 10.16 (hr, 1H), 8.56 (s, 1H), 8.04 (s, 1H), 7.86 (s, 1H), 7.62 (s, 1H), 7.42-7.11 (m, 4H), 4.17-4.04 (m, 3H), 3.06-2.94 (m, 4H), 2.75-2.71 (m, 1H), 2.52-2.49 (m, 2H), 2.19-2.10 (m, 2H), 1.17-1.10 (m, 6H)

Example 67

$^1$H NMR (DMSO-$d_6$, 400 MHz) δ 10.21 (br, 1H), 7.60 (s, 1H), 7.41-7.18 (m, 4H), 7.06 (s, 1H), 4.17-4.00 (m, 3H), 3.06-2.94 (m, 4H), 2.70-2.66 (m, 1H), 2.51-2.49 (m, 2H), 2.45 (s, 3H), 2.29 (s, 3H), 2.17-2.10 (m, 2H), 1.17-1.14 (m, 6H)

Example 68

$^1$H NMR (DMSO-$d_6$, 400 MHz) δ 10.31 (br, 1H), 8.44 (s, 1H), 8.14 (s, 1H), 7.71 (s, 1H), 7.47 (s, 1H), 7.42-7.03 (m, 4H), 4.17-4.11 (m, 1H), 4.02-3.99 (m, 2H), 3.89 (s, 3H), 3.06-2.92 (m, 4H), 2.72-2.69 (m, 1H), 2.50-2.46 (m, 2H), 2.19-2.09 (m, 2H), 1.19-1.11 (m, 6H)

Example 69

$^1$H NMR (DMSO-$d_6$, 400 MHz) δ 10.02 (br, 1H), 9.01 (d, 1H, J=4.7 Hz), 8.33 (d, 1H, J=4.7 Hz), 7.62-7.56 (m, 2H), 7.43-7.00 (m, 5H), 4.15-3.99 (m, 3H), 3.07-2.93 (m, 4H), 2.72-2.68 (m, 1H), 2.52-2.43 (m, 2H), 2.19-2.09 (m, 2H), 1.18-1.13 (m, 6H)

Example 70

$^1$H NMR (DMSO-$d_6$, 400 MHz) δ 10.01 (br, 1H), 7.71 (s, 1H), 7.65 (d, 1H, J=3.6 Hz), 7.42-7.37 (m, 1H), 7.36 (s, 1H), 7.30-7.18 (m, 2H), 7.00 (s, 1H), 6.92 (d, 1H, J=3.6 Hz), 4.17-4.03 (m, 3H), 3.06-2.96 (m, 4H), 2.72-2.67 (m, 1H), 2.52 (s, 3H), 2.51-2.44 (m, 2H), 2.20-2.12 (m, 2H), 1.18-1.10 (m, 6H)

Example 71

$^1$H NMR (DMSO-$d_6$, 400 MHz) δ 10.43 (br, 1H), 7.88 (s, 1H), 7.58 (s, 1H), 7.49-7.17 (m, 5H), 4.19-3.98 (m, 6H), 3.12-2.98 (m, 4H), 2.72-2.67 (m, 1H), 2.53-2.46 (m, 2H), 2.20-2.12 (m, 2H), 1.18-1.10 (m, 6H)

Example 72

$^1$H NMR (DMSO-$d_6$, 400 MHz) δ 10.27 (br, 1H), 9.21 (s, 1H), 7.49 (s, 1H), 7.37-7.31 (m, 1H), 7.49 (s, 1H), 7.24-7.18 (m, 1H), 7.14-7.11 (m, 1H), 7.07 (s, 1H), 4.03-3.92 (m, 3H), 3.00-2.87 (m, 7H), 2.68 (s, 3H), 2.55-2.49 (m, 1H), 2.51-2.48 (m, 2H), 2.05-2.01 (m, 2H), 1.13-1.08 (m, 6H)

Example 73

$^1$H NMR (DMSO-$d_6$, 400 MHz) δ 10.01 (br, 1H), 8.01 (s, 1H), 7.86 (s, 1H), 7.44-7.18 (m, 4H), 4.11-4.08 (m, 3H), 3.05-2.93 (m, 4H), 2.73 (s, 3H), 2.73-2.68 (m, 1H), 2.49-2.41 (m, 2H), 2.16-2.11 (m, 2H), 1.18-1.14 (m, 6H)

Example 74

$^1$H NMR (DMSO-$d_6$, 400 MHz) δ 10.42 (br, 1H), 8.26 (s, 1H), 8.01 (s, 1H), 7.85 (s, 1H), 7.21-7.16 (m, 3H), 4.12-4.09 (m, 3H), 3.14 (s, 3H), 3.07-2.93 (m, 7H), 2.70-2.67 (m, 1H), 2.52-2.49 (m, 2H), 2.12-2.10 (m, 2H), 1.16 (t, 6H, J=6.9 Hz)

Example 75

$^1$H NMR (DMSO-$d_6$, 400 MHz) δ 9.98 (br, 1H), 8.24 (d, 1H, J=7.6 Hz), 8.17 (d, 1H, J=8.16 Hz), 8.14 (s, 1H), 7.96 (s, 1H), 7.63 (dd, 1H, J=7.2 and 8.1 Hz), 7.56 (dd, 1H, J=7.2 and 7.6 Hz), 7.26 (s, 1H), 7.23-7.17 (m, 2H), 4.16-4.13 (m, 3H), 3.07-2.97 (m, 4H), 2.74-2.72 (m, 1H), 2.51-2.45 (m, 2H), 2.16-2.14 (m, 2H), 1.17 (t, 6H, J=7.1 Hz)

Example 76

$^1$H NMR (DMSO-$d_6$, 400 MHz) δ 9.99 (br, 1H), 8.21 (s, 1H), 8.04 (s, 1H), 7.86-7.81 (m, 2H), 7.50-7.42 (m, 2H), 7.17 (s, 1H), 7.15-7.11 (m, 2 H), 4.05-3.99 (m, 3H), 3.02-2.94 (m, 4H), 2.73-2.68 (m, 1H), 1, 2.51-2.45 (m, 2H), 2.11-2.09 (m, 2H), 1.15 (t, 6H, J=7.1 Hz)

Example 77

$^1$H NMR (DMSO-$d_6$, 400 MHz) δ 10.76 (hr, 1H), 8.43 (s, 1H), 7.80 (s, 1H), 7.44-7.05 (m, 5H), 4.14-4.05 (m, 3H), 3.07-2.90 (m, 4H), 2.76 (s, 3H), 2.74-2.69 (m, 1H), 2.54-2.49 (m, 2H), 2.17-2.09 (m, 2H), 1.17 (t, 6H, J=7.1 Hz)

Example 78

$^1$H NMR (DMSO-$d_6$, 400 MHz) δ 10.94 (br, 1H), 8.43 (s, 1H), 7.82 (s, 1H), 7.43 (s, 1H), 7.16-7.08 (m, 3H), 4.29-4.08 (m, 3H), 3.04-2.92 (m, 4H), 2.75 (s, 3H), 2.74-2.71 (m, 1H), 2.57-2.51 (m, 2H), 2.12-2.08 (m, 2H), 1.16 (t, 6H, J=7.1 Hz)

Example 79

$^1$H NMR (DMSO-$d_6$, 400 MHz) δ 10.22 (br, 1H), 7.86 (s, 1H), 7.62 (s, 1H), 7.43-7.09 (m, 4H), 7.01 (s, 1H), 4.13-4.01 (m, 4H), 3.06-2.95 (m, 4H), 2.71-2.67 (m, 1H), 2.51-2.48 (m, 2H), 2.18-2.09 (m, 2H), 1.16 (t, 6H, J=7.1 Hz)

Example 80

$^1$H NMR (DMSO-$d_6$, 400 MHz) δ 10.48 (br, 1H), 7.86 (s, 1H), 7.65 (s, 1H), 7.17-7.12 (m, 3H), 7.04 (s, 1H), 4.12-4.00 (m, 4H), 3.07-2.91 (m, 4H), 2.73-2.68 (m, 1H), 2.51-2.48 (m, 2H), 2.11-2.06 (m, 2H), 1.16 (t 6H, J=7.1 Hz)

Example 81

$^1$H NMR (DMSO-$d_6$, 400 MHz) δ 9.96 (br, 1H), 8.78 (s, 1H), 7.86 (s, 1H), 7.67 (s, 1H), 7.38-7.07 (m, 4H), 4.08-3.98 µm, 3H), 3.46 (s, 3H), 3.04-2.89 (m, 4H), 2.72-2.67 (m, 1H), 2.47-2.41 (m, 2H), 2.12-2.06 (m, 2H), 1.14 (t, 6H, J=7.1 Hz)

Example 82

$^1$H NMR (DMSO-$d_6$, 400 MHz) δ 10.32 (br, 1H), 7.98 (s, 1H), 7.82 (s, 1H), 7.43-7.17 (m, 4H), 4.12-4.10 (m, 3H), 3.20 (s, 3H), 3.03-2.94 (m, 7H), 2.70-2.68 (m, 1H), 2.51-2.49 (m, 2H), 2.36 (s, 3H), 2.18-2.12 (m, 2H), 1.16 (t, 6H, J=6.9 Hz)

Example 83

$^1$H NMR (DMSO-$d_6$, 400 MHz) δ 10.18 (br, 1H), 8.01 (s, 1H), 7.84 (s, 1H), 7.24 (s, 1H), 7.20-7.15 (m, 2H), 4.12-4.09 (m, 3H), 3.21 (s, 3H), 3.02-2.91 (m, 7H), 2.69-2.67 (m, 1H), 2.50-2.48 (m, 2H), 2.36 (s, 3H), 2.15-2.10 (m, 2H), 1.16 (t, 6H, J=7.0 Hz)

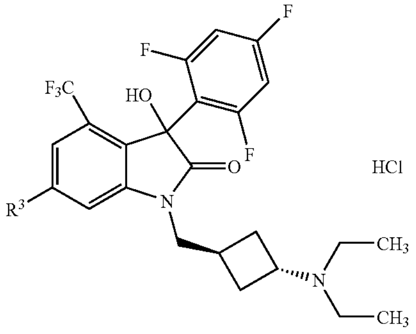

HCl

| No. | $R^3$ |
|---|---|
| 84 | 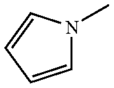 |
| 85 | 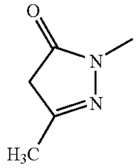 |

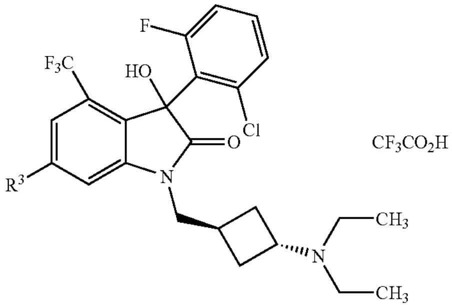

$CF_3CO_2H$

| No. | $R^3$ |
|---|---|
| 86 | 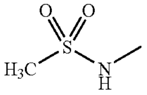 |
| 87 | 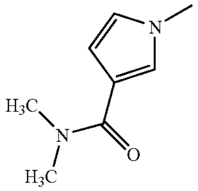 |
| 88 | 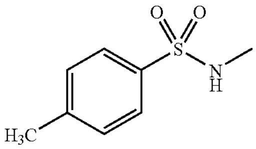 |

-continued
| No. | | |
|---|---|---|
| 89 | 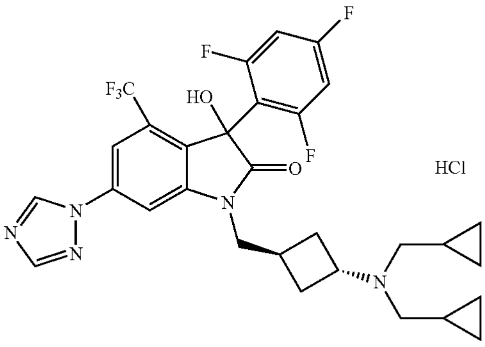 | HCl |
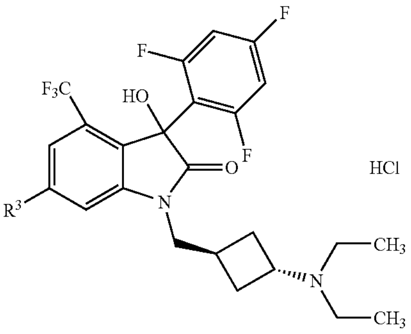
HCl
| No. | $R^3$ |
|---|---|
| 90 | 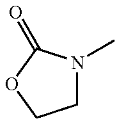 |
| 91 | 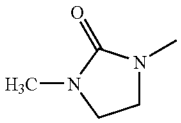 |
| 92 | 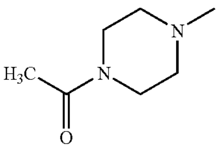 |
| 93 | 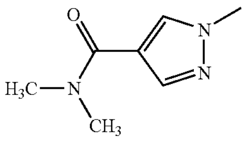 |
-continued
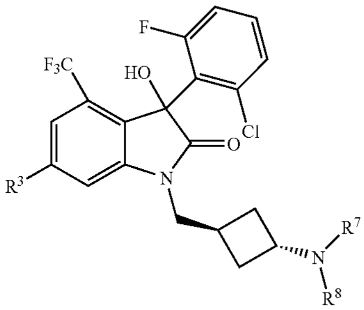
HCl
| No. | $R^3$ | $—NR^7R^8$ |
|---|---|---|
| 94 | 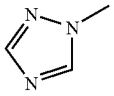 | 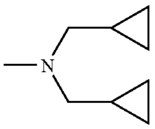 |
| 95 | 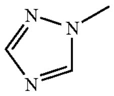 | 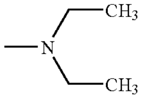 |
| 96 | 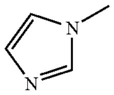 | 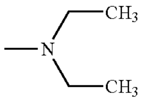 |
| 97 | 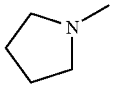 | 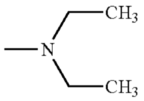 |
Example 84
$^1$H NMR (DMSO-$d_6$, 400 MHz) δ 10.39 (br, 1H), 7.77 (s, 1H), 7.64 (m, 2H), 7.47 (s, 1H), 7.16 (m, 2H), 7.05 (s, 1H), 6.34 (m, 2H), 4.16-3.96 (m, 3H), 3.10-2.90 (m, 4H), 2.75-2.62 (m, 1H), 2.48-2.41 (m, 2H), 2.16-2.04 (m, 2H), 1.16 (t, 6H, J=7.2 Hz)
Example 85
LC-MS m/z 583 ($M+H^+$)
Example 86
LC-MS m/z 578 ($M+H^+$)
Example 87
LC-MS m/z 621 ($M+H^+$)
Example 88
LC-MS m/z 654 ($M+H^+$)
Example 89
$^1$H NMR (DMSO-$d_6$, 400 MHz) δ 9.80 (br, 1H), 9.54 (s, 1H), 8.34 (s, 1H), 8.06 (s, 1H), 7.81 (s, 1H), 7.20 (s, 1H), 7.28-7.13 (m, 2H), 4.26-4.16 (m, 1H), 4.15-3.90 (m, 2H), 3.15-2.85 (m, 4H) 2.75-2.65 (m, 1H), 2.56-2.45 (m, 2H), 2.20-2.05 (m, 2H), 1.13-1.02 (m, 2H), 0.67-0.56 (m, 4H), 0.45-0.32 (m, 4H)

Example 90

$^1$H NMR (DMSO-$d_6$, 400 MHz) δ 10.50 (br, 1H), 7.57 (s, 1H), 7.56 (s, 1H), 7.13 (t, 2H, J=9.7 Hz), 7.01 (s, 1H), 4.49 (t, 2H, J=7.9 Hz), 4.18 (t, 2H, J=7.9 Hz), 4.11-3.87 (m, 3H), 3.11-2.85 (m, 4H), 2.68-2.58 (m, 1H), 2.57-2.40 (m, 2H), 2.17-2.03 (m, 2H), 1.15 (t, 6H, J=7.2 Hz)

Example 91

$^1$H NMR (DMSO-$d_6$, 400 MHz) δ 10.07 (br, 1H), 7.63 (s, 1H), 7.52 (s, 1H), 7.28-7.05 (m, 2H), 6.90 (s, 1H), 4.12-3.85 (m, 5H), 3.52-3.45 (m, 2H), 3.11-2.89 (m, 4H), 2.80 (s, 3H), 2.70-2.58 (m, 1H), 2.52-2.38 (m, 2H), 2.19-2.02 (m, 2H), 1.18-1.12 (m, 6H)

Example 92

$^1$H NMR (DMSO-$d_6$, 400 MHz) δ 10.25 (br, 1H), 7.17-7.03 (m, 3H), 6.75 (s, 1H), 6.67 (s, 1H), 4.12-3.86 (m, 3H), 3.62-3.55 (m, 4H), 3.40-3.25 (m, 4H), 3.12-2.88 (m, 4H), 2.70-2.57 (m, 1H), 2.56-2.38 (m, 2H), 2.12-2.00 (m, 5H), 1.18-1.12 (m, 6H)

Example 93

$^1$H NMR (DMSO-$d_6$, 400 MHz) δ 9.88 (br, 1H), 9.12 (s, 1H), 8.11 (s, 1H), 8.05 (s, 1H), 7.86 (s, 1H), 7.21-7.09 (m, 3H), 4.19-3.98 (m, 3H), 3.30-2.89 (m, 10H), 2.80-2.64 (m, 1H), 2.51-2.37 (m, 2H), 2.19-2.05 (m, 2H), 1.18-1.12 (m, 6H)

Example 94

$^1$H NMR (DMSO-$d_6$, 400 MHz) δ 10.16 (br, 1H), 9.59 (s, 1H), 8.34 (s, 1H), 8.08 (s, 1H), 7.79 (s, 1H), 7.44-7.12 (m, 4H), 4.27-4.22 (m, 1H), 4.07-4.05 (m, 2H), 2.99-2.94 (m, 4H), 2.75-2.72 (m, 1H), 2.57-2.51 (m, 2H), 2.22-2.14 (m, 2H), 1.09-1.07 (m, 2H), 0.65-0.60 (m, 4H), 0.41-0.37 (m, 4H)

Example 95

$^1$H NMR (DMSO-$d_6$, 400 MHz) δ 10.46 (hr, 1H), 9.59 (s, 1H), 8.34 (s, 1H), 8.08 (s, 1H), 7.79 (s, 1H), 7.45-7.14 (m, 4H), 4.16-4.05 (m, 3H), 3.07-2.93 (m, 4H), 2.81-2.74 (m, 1H), 2.56-2.49 (m, 2H), 2.26-2.11 (m, 2H), 1.18-1.14 (m, 6H)

Example 96

$^1$H NMR (DMSO-$d_6$, 400 MHz) δ 10.09 (br, 1H), 9.16 (br, 1H), 8.24 (s, 1H), 7.95 (s, 1H), 7.70 (s, 1H), 7.55 (br, 1H), 7.45-7.12 (m, 4H), 4.16-4.03 (m, 3H), 3.16-2.92 (m, 4H), 2.78-2.73 (m, 1H), 2.51-2.41 (m, 2H), 2.21-2.08 (m, 2H), 1.17-1.13 (m, 6H)

Example 97

$^1$H NMR (DMSO-$d_6$, 400 MHz) δ 10.42 (br, 1H), 7.44-7.05 (m, 4H), 6.53 (s, 1H), 6.22 (s, 1H), 4.10-4.07 (m, 1H), 3.95-3.92 (m, 2H), 3.49-3.46 (m, 2H), 3.36-3.31 (m, 2H), 3.05-2.89 (m, 4H), 2.69-2.65 (m, 1H), 2.50-2.46 (m, 2H), 2.16-2.09 (m, 2H), 1.99-1.95 (m, 4H), 1.18-1.13 (m, 6H)

The compounds of Example 98 to 118 were synthesized in a similar manner to Example 1, 8 or 9.

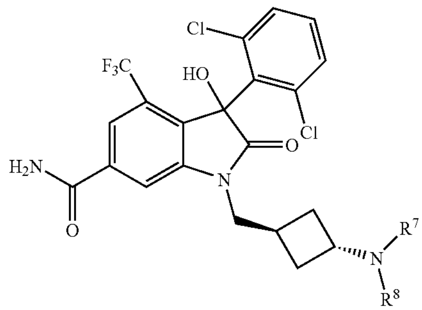

HCl

| No. | —$NR^7R^8$ |
|---|---|
| 98 | 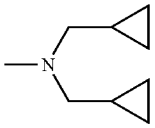 |
| 99 | 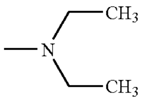 |

| No | |
|---|---|
| 100 | 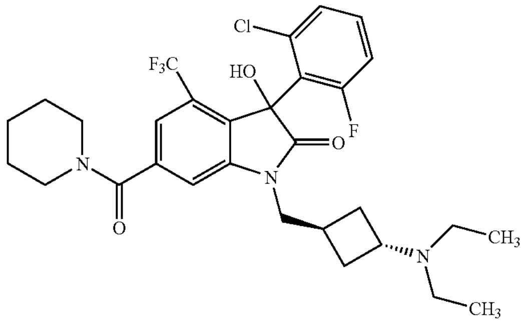 |

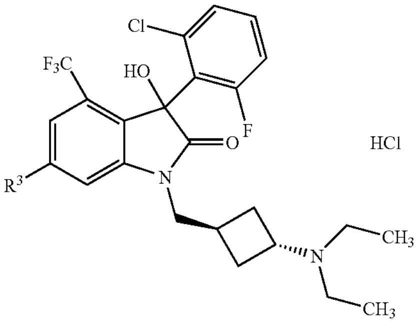

HCl

| No. | $R^3$ |
|---|---|
| 101 | 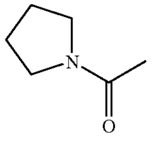 |

-continued
| | |
|---|---|
| 102 | 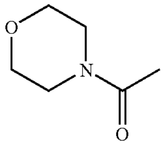 |
| 103 | 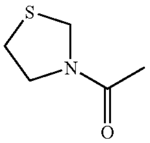 |
| 104 | 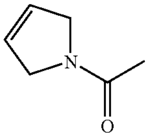 |
| 105 | 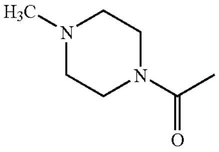 |
| 106 | 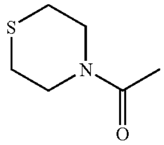 |
| 107 | 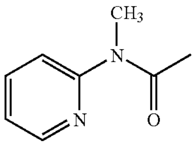 |
| 108 | 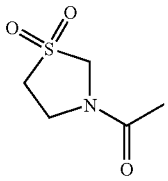 |
| 109 | 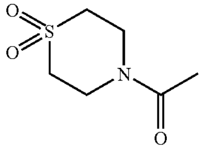 |
| 110 | 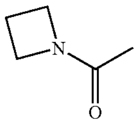 |
| 111 | 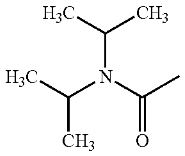 |
-continued
| | |
|---|---|
| 112 | 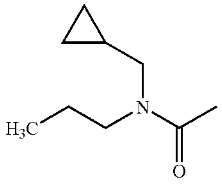 |
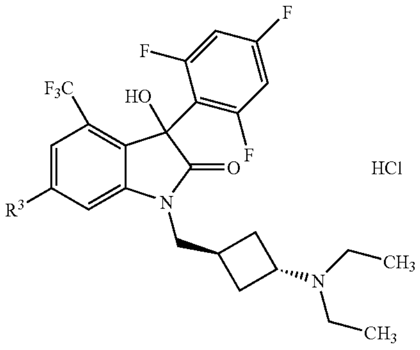
HCl
| No. | $R^3$ |
|---|---|
| 113 | 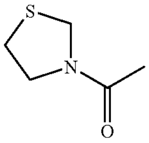 |
| 114 | 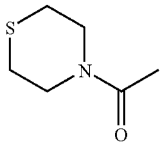 |
| 115 | 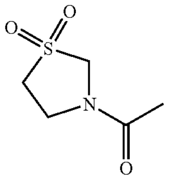 |
| 116 | 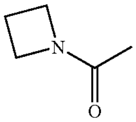 |
| 117 | 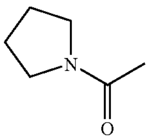 |
| 118 | 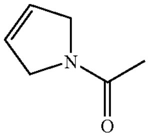 |

Example 98

$^1$H NMR (DMSO-$d_6$, 400 MHz) δ 10.10 (br, 1H), 8.36 (s, 1H), 7.98 (s, 1H), 7.81 (s, 1H), 7.74 (s, 1H), 7.52-7.48 (m, 1H), 7.36-7.32 (m, 2H), 7.19 (s, 1H), 4.27-4.20 (m, 1H), 4.05-3.94 (m, 2H), 3.05-2.90 (m, 4H), 2.70-2.59 (m, 1H), 2.55-2.40 (m, 2H), 2.25-2.01 (m, 2H), 1.13-0.98 (m, 2H), 0.67-0.54 (m, 4H), 0.42-0.32 (m, 4H)

Example 99

$^1$H NMR (DMSO-$d_6$, 400 MHz) δ 10.30 (br, 1H), 8.36 (s, 1H), 7.96 (s, 1 H), 7.81 (s, 1H), 7.74 (s, 1H), 7.52-7.48 (m, 1H), 7.36-7.15 (m, 2H), 7.20 (s, 1H), 4.33-4.17 (m, 1H), 4.16-3.92 (m, 2H), 3.05-2.83 (m, 4H), 2.75-2.60 (m, 1H), 2.54-2.38 (m, 2H), 2.25-2.00 (m, 2H), 1.27-1.00 (m, 6H)

Example 100

$^1$H NMR ($CDCl_3$, 400 MHz) δ 7.35-7.05 (m, 5H), 4.19-3.80 (m, 3H), 3.72 (br, 2H), 3.45-3.30 (m, 3H), 2.51-2.46 (m, 5H), 2.20-1.95 (m, 4H), 1.89-1.47 (m, 6H), 0.98 (t, 6H, J=7.0 Hz)

Example 101

$^1$H NMR (DMSO-$d_6$, 400 MHz) δ 10.16 (br, 1H), 7.70 (s, 1H), 7.44-7.05 (m, 5H), 4.16-4.09 (m, 1H), 4.00 (d, 2H, J=7.7 Hz), 3.51-3.47 (m, 2H), 3.39-3.36 (m, 2H), 3.05-2.91 (m, 4H), 2.69-2.64 (m, 1H), 2.50-2.44 (m, 2H), 2.17-2.05 (m, 2H), 1.92-1.82 (m, 4H), 1.16 (t, 6H, J=7.2 Hz)

Example 102

$^1$H NMR (DMSO-$d_6$, 400 MHz) δ 10.10 (br, 1H), 7.62 (s, 1H), 7.44-7.10 (m, 5H), 4.13-4.07 (m, 1H), 3.99 (d, 2H, J=7.7 Hz), 3.66-3.57 (m, 6H), 3.31-3.29 (m, 2H), 3.05-2.93 (m, 4H), 2.69-2.64 (m, 1H), 2.50-2.43 (m, 2H), 2.15-2.06 (m, 2H), 1.16 (t, 6H, J=7.2 Hz)

Example 103

$^1$H NMR (DMSO-$d_6$, 400 MHz) δ 9.95 (br, 1H), 7.71 (s, 1H), 7.44-7.05 (m, 5H), 4.65 (br, 1H), 4.51 (br, 1H), 4.13-4.09 (m, 1H), 4.00 (d, 2H, J=7.7 Hz), 3.85 (br, 1H), 3.68 (br, 1H), 3.06-2.92 (m, 6H), 2.68-2.64 (m, 1H), 2.50-2.42 (m, 2H), 2.17-2.07 (m, 2H), 1.16 (t, 6H, J=6.9 Hz)

Example 104

$^1$H NMR (DMSO-$d_6$, 400 MHz) δ 10.38 (br, 1H), 7.76 (s, 1H), 7.43-7.04 (m, 5H), 6.00-5.98 (m, 1H), 5.89-5.86 (m, 1H), 4.32 (br, 2H), 4.22 (br, 2H), 4.15-4.08 (m, 1H), 4.00 (d, 2H, J=7.7 Hz), 3.07-2.89 (m, 4H), 2.69-2.64 (m, 1H), 2.51-2.43 (m, 2H), 2.15-2.06 (m, 2H), 1.16 (t, 6H, J=7.2 Hz)

Example 105

$^1$H NMR (DMSO-$d_6$, 400 MHz) δ 10.98 (br, 1H), 10.40 (br, 1H), 7.66 (s, 1H), 7.44-7.10 (m, 5H), 4.14-4.11 (m, 1H), 3.99 (d, 2H, J=7.8 Hz), 3.61-3.31 (m, 4H), 3.15-2.92 (m, 8H), 2.77 (s, 3H), 2.66-2.63 (m, 1H), 2.50-2.48 (m, 2H), 2.15-2.06 (m, 2H), 1.16 (t, 6H, J=7.2 Hz)

Example 106

$^1$H NMR (DMSO-$d_6$, 400 MHz) δ 10.35 (br, 1H), 7.62 (s, 1H), 7.44-7.18 (m, 4H), 7.10 (s, 1H), 4.13-4.07 (m, 1H), 3.98 (d, 2H, J=7.7 Hz), 3.89 (br, 2H), 3.51 (br, 2H), 3.04-2.91 (m, 4H), 2.74-2.62 (m, 5H), 2.49-2.47 (m, 2H), 2.15-2.06 (m, 2H), 1.15 (t, 6H, J=7.2 Hz)

Example 107

$^1$H NMR (DMSO-$d_6$, 400 MHz) δ 10.80 (br, 1H), 8.39 (d, 1H, J=4.8 Hz), 7.74 (dd, 1H, J=7.7 and 7.8 Hz), 7.40-7.35 (m, 2H), 7.27-7.14 (m, 5H), 7.11 (s, 1H), 4.09-4.03 (m, 1H), 3.75-3.70 (m, 2H), 3.47 (s, 3H), 3.06-2.86 (m, 4H), 2.51-2.49 (m, 2H), 2.42-2.37 (m, 1H), 2.05-2.00 (m, 2H), 1.18-1.08 (m, 6H)

Example 108

$^1$H NMR (DMSO-$d_6$, 400 MHz) δ 10.00 (br, 1H), 7.71 (s, 1H), 7.44-7.05 (m, 5H), 4.70 (br, 2H), 4.10-3.98 (m, 5H), 3.53-3.49 (m, 2H), 3.06-2.93 (m, 4H), 2.68-2.64 (m, 1H), 2.49-2.41 (m, 2H), 2.16-2.08 (m, 2H), 1.19-1.15 (m, 6H)

Example 109

$^1$H NMR (DMSO-$d_6$, 400 MHz) δ 10.22 (br, 1H), 7.66 (s, 1H), 7.48 (s, 1H), 7.44-7.18 (m, 3H), 7.13 (s, 1H), 4.13-3.92 (m, 5H), 3.65 (br, 2H), 3.04-2.91 (m, 4H), 2.68-2.63 (m, 1H), 2.50-2.47 (m, 6H), 2.17-2.07 (m, 2H), 1.19-1.15 (m, 6H)

Example 110

$^1$H NMR (DMSO-$d_6$, 400 MHz) δ 10.24 (br, 1H), 7.80 (s, 1H), 7.46 (s, 1H), 7.20-7.15 (m, 3H), 7.15 (s, 1H), 4.34-4.30 (m, 2H), 4.13-4.01 (m, 5H), 3.05-2.92 (m, 4H), 2.67-2.63 (m, 1H), 2.50-2.43 (m, 2H), 2.30-2.26 (m, 2H), 2.16-2.08 (m, 2H), 1.16 (t, 6H, J=7.1 Hz)

Example 111

$^1$H NMR (DMSO-$d_6$, 400 MHz) δ 10.17 (br, 1H), 7.52 (s, 1H), 7.45-7.04 (m, 3H), 7.13 (s, 1H), 7.08 (s, 1H), 4.18-3.95 (m, 3H), 3.68-3.53 (m, 2H), 3.10-2.88 (m, 4H), 2.67-2.53 (m, 1H), 2.50-2.38 (m, 2H), 2.20-2.00 (m, 2H), 1.56-1.00 (m, 18H)

Example 112

$^1$H NMR (DMSO-$d_6$, 400 MHz) δ 10.71 (br, 1H), 7.60 (s, 1H), 7.45-7.08 (m, 3H), 7.19 (s, 1H), 7.11 (s, 1H), 4.17-3.94 (m, 3H), 3.52-3.26 (m, 2H), 3.24-2.83 (m, 6H), 2.67-2.42 (m, 3H), 2.18-1.97 (m, 2H), 1.72-1.60 (m, 1H), 1.59-1.42 (m, 1H), 1.20-1.15 (m, 6H), 0.98-0.87 (m, 3H), 0.72-0.61 (m, 1H), 0.57-0.42 (m, 2H), 0.35-0.28 (m, 1H), 0.08-0.01 (m, 1H)

Example 113

$^1$H NMR (DMSO-$d_6$, 400 MHz) δ 10.63 (br, 1H), 7.76 (s, 1H), 7.44 (s, 1H), 7.22-7.08 (m, 3H), 4.65 (br, 1H), 4.52 (br, 1H), 4.13-3.90 (m, 3H), 3.84 (br, 1H), 3.69 (br, 1H), 3.15-2.85 (m, 6H), 2.68-2.58 (m, 1H), 2.58-2.44 (m, 2H), 2.12-2.01 (m, 2H), 1.19-1.08 (m, 6H)

Example 114

$^1$H NMR (DMSO-$d_6$, 400 MHz) δ 10.55 (br, 1H), 7.66 (s, 1H), 7.35 (s, 1H), 7.16 (t, 2H, J=9.7 Hz), 7.11 (s, 1H), 4.14-3.82 (m, 5H), 3.50 (br, 2H), 3.08-2.75 (m, 4H), 2.78-2.58 (m, 5H), 2.57-2.45 (m, 2H), 2.11-2.02 (m, 2H), 1.19-1.05 (m, 6H)

Example 115

$^1$H NMR (DMSO-$d_6$, 400 MHz) δ 9.83 (br, 1H), 7.72 (s, 1H), 7.45 (s, 1H), 7.21-7.08 (m, 3H), 4.70 (s, 2H), 4.18-3.86

(m, 5H), 3.58-3.45 (m, 2H), 3.11-2.87 (m, 4H), 2.72-2.59 (m, 1H), 2.50-2.34 (m, 2H), 2.16-2.06 (m, 2H), 1.15 (t, 6H, J=7.1 Hz)

Example 116

$^1$H NMR (DMSO-$d_6$, 400 MHz) δ 10.77 (br, 1H), 7.69 (s, 1H), 7.46 (s, 1H), 7.19-7.12 (m, 3H), 4.35-4.30 (t, 2H, J=8.0 Hz), 4.08 (t, 2H, J=8.0 Hz), 4.05-3.97 (m, 3H), 3.05-2.86 (m, 4H), 2.65-2.47 (m, 3H), 2.33-2.21 (m, 2H), 2.12-2.01 (m, 2H), 1.14-1.11 (m, 6H)

Example 117

$^1$H NMR (DMSO-$d_6$, 400 MHz) δ 10.23 (br, 1H), 7.72 (s, 1H), 7.40 (s, 1H), 7.20-7.15 (m, 3H), 4.14-3.93 (m, 3H), 3.51-3.47 (m, 2H), 3.39-3.34 (m, 2H), 3.05-2.92 (m, 4H), 2.66-2.62 (m, 1H), 2.50-2.43 (m, 2H), 2.11-2.07 (m, 2H), 1.92-1.82 (m, 4H), 1.16 (t, 6H, J=7.2 Hz)

Example 118

$^1$H NMR (DMSO-$d_6$, 400 MHz) δ 10.24 (br, 1H), 7.80 (s, 1H), 7.46 (s, 1H), 7.20-7.15 (m, 2H), 7.15 (s, 1H), 6.00-5.97 (m, 1H), 5.89-5.86 (m, 1H), 4.31 (br, 2H), 4.22 (br, 2H), 4.16-4.08 (m, 1H), 4.01-3.95 (m, 2H), 3.07-2.91 (m, 4H), 2.68-2.62 (m, 1H), 2.50-2.43 (m, 2H), 2.09-2.04 (m, 2H), 1.15 (t, 6H, J=7.2 Hz)

Example 119

1-{[trans-3-(diethylamino)-cyclobutyl]-methyl}-3-hydroxy-6-[3-(2-oxoimidazolidin-1-yl)-prop-1-yn-1-yl]-4-(trifluoromethyl)-3-(2,4,6-trifluorophenyl)-1,3-dihydro-2H-indol-2-one Hydrochloride

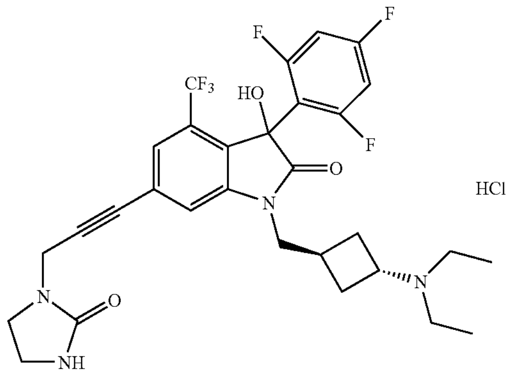

HCl

To a mixture of 1-{[trans-3-(diethylamino)-cyclobutyl]-methyl}-3-hydroxy-6-iodo-4-(trifluoromethyl)-3-(2,4,6-trifluorophenyl)-1,3-dihydro-2H-indol-2-one (45 mg, 0.073 mmol) synthesized in a similar manner to Example 1 and the compound of Reference example 18 (23 mg, 0.184 mmol) was added triethylamine (1.0 mL) under nitrogen, and the mixture was heated to 50° C. Thereto were added dichloro bistriphenylphosphine palladium (10 mg, 0.015 mmol) and copper iodide (6.0 mg, 0.029 mmol), and the mixture was stirred at 50° C. for 9 hours. Thereto were added water and saturated aqueous sodium bicarbonate, and the mixture was extracted with ethyl acetate, dried over magnesium sulfate and filtered. The filtrate was concentrated in vacuo and the residue was purified by silica gel chromatography (chloroform/methanol=20/1) to give a salt-free compound. Subsequently, the salt-free compound was dissolved in dioxane, and thereto were added 4N hydrochloric acid in dioxane and toluene, and then the mixture was evaporated to give the titled compound (40 mg, 80%).

$^1$H NMR (DMSO-$d_6$, 400 MHz) δ 10.33 (br, 1H), 7.69 (s, 1H), 7.38 (s, 1H), 7.20-7.05 (m, 3H), 6.63 (br, 1H), 4.18 (s, 2H), 4.16-3.89 (m, 3H), 3.50-3.38 (m, 2H), 3.32-3.26 (m, 2H), 3.10-2.85 (m, 4H), 2.70-2.58 (m, 1H), 2.55-2.40 (m, 2H), 2.11-2.00 (m, 2H), 1.18-1.06 (m, 6H).

The compounds of Example 120 to 122 were synthesized in a similar manner to Example 119,

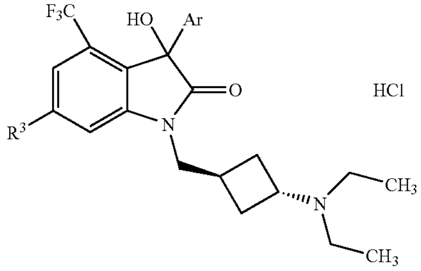

HCl

| No. | $R^3$ | Ar |
|---|---|---|
| 120 | 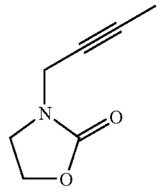 | 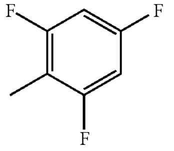 |
| 121 | 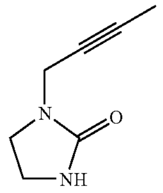 | 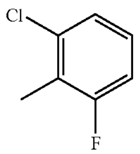 |
| 122 | 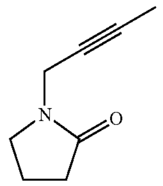 | 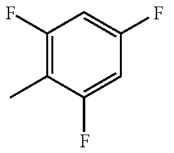 |

Example 120

$^1$H NMR (DMSO-$d_6$, 400 MHz) δ 10.49 (br, 1H), 7.71 (s, 1H), 7.42 (s, 1H), 7.16 (t, 2H, J=10.0 Hz), 7.10 (s, 1H), 4.38-4.30 (m, 4H), 4.12-3.85 (m, 3H), 3.67 (d, 1H, J=8.1 Hz), 3.69 (d, 1H, J=8.1 Hz), 3.10-2.85 (m, 4H), 2.70-2.58 (m, 1H), 2.57-2.41 (m, 2H), 2.12-2.00 (m, 2H), 1.57 (t, 6H, J=7.2 Hz)

Example 121

$^1$H NMR (DMSO-$d_6$, 400 MHz) δ 10.30 (br, 1H), 7.64 (s, 1H), 7.43-7.14 (m, 3H), 7.06 (s, 1H), 6.62 (s, 1H), 4.18 (s, 2H), 4.16-4.00 (m, 1H), 3.99-3.90 (m, 2H), 3.50-3.21 (m, 4H), 3.10-2.86 (m, 4H), 2.70-2.58 (m, 1H), 2.55-2.40 (m, 2H), 2.18-2.00 (m, 2H), 1.18-1.09 (m, 6H)

Example 122

$^1$H NMR (DMSO-$d_6$, 400 MHz) δ 10.44 (br, 1H), 7.70 (s, 1H), 7.40 (s, 1 H), 7.14 (t, 2H, J=9.8 Hz), 7.09 (s, 1H), 4.32 (s, 2H), 4.12-3.86 (m, 3H), 3.48 (t, 2H, J=7.0 Hz), 3.10-2.85 (m, 4H), 2.70-2.58 (m, 1H), 2.55-2.40 (m, 2H), 2.28 (t, 2H, J=8.0 Hz), 2.10-1.05 (m, 4H), 1.16 (t, 6H, J=7.1 Hz)

Example 123

N'-[1-{[trans-3-(diethylamino)-cyclobutyl]-methyl}-3-hydroxy-2-oxo-4-(trifluoromethyl)-3-(2,4,6-trifluorophenyl)-1,3-dihydro-2H-indol-6-yl]-N,N-dimethylurea hydrochloride

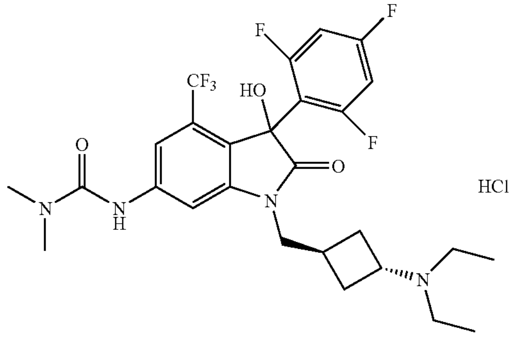

HCl

To a suspension of the compound of Example 8 (122 mg, 0.20 mmol) in toluene (0.3 mL) were added diphenylphosphoryl azide (55 mg, 0.20 mmol) and triethylamine (55 μL, 0.40 mmol) at 0° C. under nitrogen, and the mixture was heated to 110° C. and stirred for 4 hours. To the reaction solution was added a mixture of dimethylamine hydrochloride (60 mg, 0.60 mmol) and triethylamine (84 μL, 0.60 mmol), and the mixture was stirred at 90° C. for 12 hours. Thereto was added water, and the mixture was extracted with ethyl acetate, dried over magnesium sulfate and filtered. The filtrate was concentrated in vacuo and the residue was purified by silica gel chromatography (chloroform/methanol=10/1) to give a salt-free compound. Subsequently, the salt-free compound was dissolved in dioxane, and thereto were added 4N hydrochloric acid in dioxane and toluene, and then the mixture was evaporated to give the titled compound (17 mg, 13%).

$^1$H NMR (DMSO-$d_6$, 400 MHz) δ 9.95 (br, 1H), 7.96 (s, 1H), 7.81 (s, 1H), 7.23-7.08 (m, 3H), 4.18-4.07 (m, 3H), 3.12-2.88 (m, 4H), 3.02 (s, 6H), 2.72-2.63 (m, 1H), 2.50-2.39 (m, 2H), 2.43 (s, 3H), 2.18-2.05 (m, 2H), 1.15 (t, 6H, J=7.1 Hz).

The compounds of Example 124 to 125 were synthesized in a similar manner to Example 11.

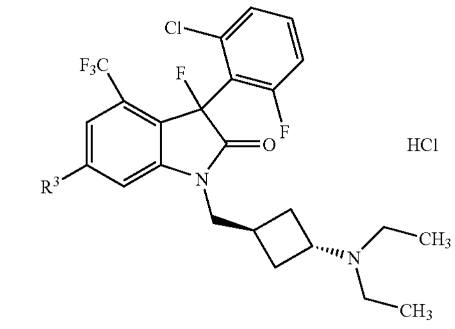

HCl

| No. | $R^3$ |
| --- | --- |
| 124 | 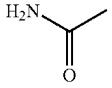 |
| 125 | 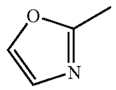 |

Example 124

$^1$H NMR (DMSO-$d_6$, 400 MHz) δ 10.15 (br, 1H), 8.63 (s, 1H), 8.30 (s, 1H), 8.10 (s, 1H), 8.06 (s, 1H), 7.80-7.54 (m, 3H), 4.32-4.27 (m, 3H), 3.38-3.18 (m, 4H), 2.94-2.88 (m, 1H), 2.71-2.53 (m, 2H), 2.36-2.27 (m, 2H), 1.44-1.35 (m, 6H)

Example 125

$^1$H NMR (DMSO-$d_6$, 400 MHz) δ 10.15 (br, 1H), 8.42 (s, 1H), 8.16 (s, 1H), 7.96 (s, 1H), 7.58 (s, 1H), 7.57-7.27 (m, 3H), 4.19-4.10 (m, 3H), 3.05-2.89 (m, 4H), 2.76-2.72 (m, 1H), 2.53-2.46 (m, 2H), 2.16-2.09 (m, 2H), 1.18-1.14 (m, 6H)

Example 126

(3S)-3-(2-chloro-6-fluorophenyl)-1-[trans-3-(diethylamino)-cyclobutylmethyl]-4-trifluoromethyl-3-hydroxy-6-iodo-1,3-dihydro-2H-indol-2-one

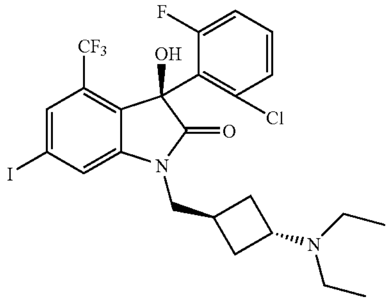

To a solution of 3-(2-chloro-6-fluorophenyl)-1-[trans-3-(diethylamino)-cyclobutylmethyl]-4-trifluoromethyl-3-hydroxy-6-iodo-1,3-dihydro-2H-indol-2-one (3.60 g, 5.89 mmol) in ethyl acetate (50 mL) was added (S)-α-methoxyphenylacetic acid (550 mg), and the mixture was heated to 6° C. and stirred for 1 hour. Then, the mixture was stirred at room temperature for 1 hour, and thereto was added hexane (10 mL), and the mixture was stirred for additional 30 minutes at room temperature. The precipitated solid was filtered (1.41 g). The solid was recrystallized from ethyl acetate (20 mL)/hexane (3.0 ml) to give (S)-methoxyphenylacetate of 3-(2-chloro-6-fluorophenyl)-1-[trans-3-(diethylamino)-cyclobutylmethyl]-4-trifluoromethyl-3-hydroxy-6-iodo-1,3-dihydro-2H-indol-2-one (970 mg). The resulting compound was converted to its nonsalt form. Thus, the titled compound (650 mg, 98% ee, 18% y.) was obtained.

Example 127

(3S)-3-(2-chloro-6-fluorophenyl)-1-[trans-3-(diethylamino)-cyclobutylmethyl]-4-trifluoromethyl-3-hydroxy-6 (2-oxazolyl)-1,3-dihydro-2H-indol-2-one hydrochloride

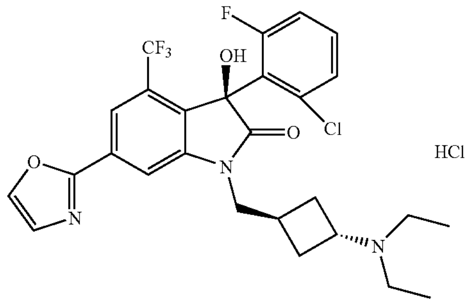

HCl

The titled compound was synthesized from the compound of Example 126 in a similar manner to Example 14.

$^1$H NMR (DMSO-$d_6$, 400 MHz) δ 10.09 (br, 1H), 8.34 (s, 1H), 7.97 (s, 1H), 7.81 (s, 1H), 7.48 (s, 1H), 7.42-7.16 (m, 4H), 4.11-4.05 (m, 3H), 3.05-2.90 (m, 4H), 2.71-2.64 (m, 1H), 2.48-2.41 (m, 2H), 2.16-2.09 (m, 2H), 1.12 (t, 6H, J=7.2 Hz).

Optical Rotation

[α]=+91.50

(C=0.094 in $CHCl_3$)

The compounds of Example 128 to 139 were synthesized in a similar manner to the above,

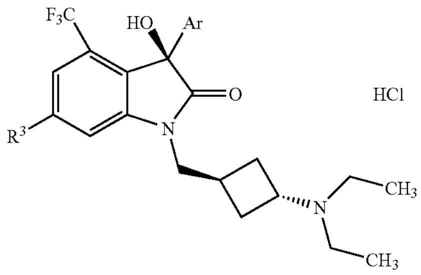

HCl

| No. | $R^3$ | Ar |
|---|---|---|
| 128 | 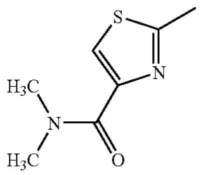 | 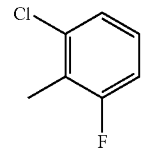 |
| 129 | 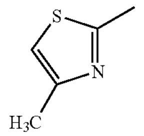 | 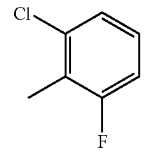 |
| 130 | 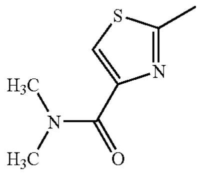 | 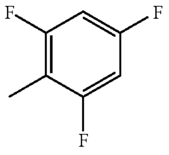 |
| 131 | 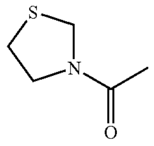 | 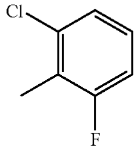 |
| 132 | 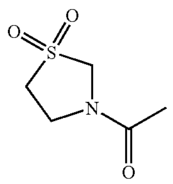 | 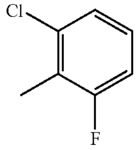 |
| 133 | 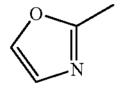 | 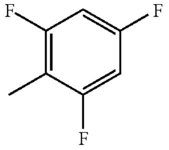 |
| 134 | 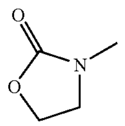 | 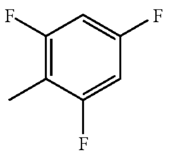 |

-continued

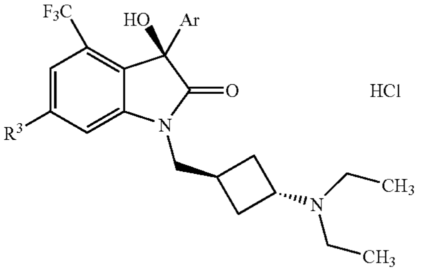

HCl

| No. | $R^3$ | Ar |
|---|---|---|
| 135 | 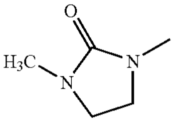 | 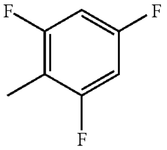 |
| 136 | 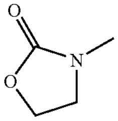 | 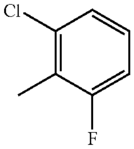 |
| 137 | 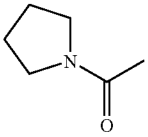 | 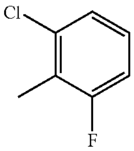 |
| 138 | 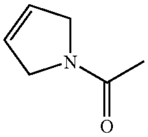 | 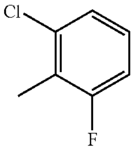 |
| 139 | 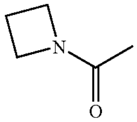 | 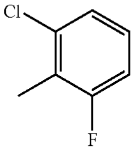 |

Example 128

$^1$H NMR (DMSO-$d_6$, 400 MHz) δ 10.18 (br, 1H), 8.25 (s, 1H), 7.99 (s, 1H), 7.83 (s, 1H), 7.44-7.15 (m, 4H), 4.13-4.09 (m, 3H), 3.14 (s, 3H), 3.10-2.96 (m, 7H), 2.73-2.67 (m, 1H), 2.49-2.44 (m, 2H), 2.20-2.12 (m, 2H), 1.19-1.13 (m, 6H)

Example 129

$^1$H NMR (DMSO-$d_6$, 400 MHz) δ 10.52 (br, 1H), 7.92 (s, 1H), 7.77 (s, 1H), 7.52 (s, 1H), 7.45-7.07 (m, 4H), 4.14-4.08 (m, 3H), 3.05-2.92 (m, 4H), 2.77-2.69 (m, 1H), 2.54-2.48 (m, 2H), 2.47 (s, 3H), 2.21-2.08 (m, 2H), 1.18-1.11 (m, 6H)

Example 130

$^1$H NMR (DMSO-$d_6$, 400 MHz) δ 10.42 (br, 1H), 8.26 (s, 1H), 8.01 (s, 1H), 7.85 (s, 1H), 7.21-7.16 (m, 3H), 4.12-4.09 (m, 3H), 3.14 (s, 3H), 3.07-2.93 (m, 7H), 2.70-2.67 (m, 1H), 2.52-2.49 (m, 2H), 2.12-2.10 (m, 2H), 1.16 (t, 6H, J=6.9 Hz)

Example 131

$^1$H NMR (DMSO-$d_6$, 400 MHz) δ 10.20 (br, 1H), 7.71 (s, 1H), 7.44-7.05 (m, 5H), 4.65 (br, 1H), 4.51 (br, 1H), 4.13-4.09 (m, 1H), 4.00 (d, 2H, J=7.7 Hz), 3.85 (br, 1H), 3.68 (br, 1H), 3.06-2.92 (m, 6H), 2.68-2.64 (m, 1H), 2.50-2.42 (m, 2H), 2.17-2.07 (m, 2H), 1.16 (t, 6H, J=6.9 Hz)

Example 132

$^1$H NMR (DMSO-$d_6$, 400 MHz) δ 10.21 (br, 1H), 7.71 (s, 1H), 7.44-7.05 (m, 5H), 4.70 (br, 2H), 4.10-3.98 (m, 5H), 3.53-3.49 (m, 2H), 3.06-2.93 (m, 4H), 2.68-2.64 (m, 1H), 2.49-2.41 (m, 2H), 2.16-2.08 (m, 2H), 1.19-1.15 (m, 6H)

Example 133

$^1$H NMR (DMSO-$d_6$, 400 MHz) δ 10.38 (br, 1H), 8.36 (s, 1H), 8.03 (s, 1H), 7.85 (s, 1H), 7.50 (d, 1H, J=0.53 Hz), 7.22 (s, 1H), 7.20-7.12 (m, 2H), 4.15-4.00 (m, 3H), 3.15-2.85 (m, 4H), 2.95-2.63 (m, 1H), 2.58-2.43 (m, 2H), 2.18-2.05 (m, 2H), 1.30-1.08 (m, 6H)

Example 134

$^1$H NMR (DMSO-$d_6$, 400 MHz) δ 10.15 (br, 1H), 7.58 (s, 1H), 7.55 (s, 1H), 7.14 (t, 2H, J=9.7 Hz), 7.01 (s, 1H), 4.49 (t, 2H, J=7.9 Hz), 4.18 (t, 2H, J=7.9 Hz), 4.11-3.87 (m, 3H), 3.11-2.85 (m, 4H), 2.68-2.58 (m, 1H), 2.57-2.40 (m, 2H), 2.17-2.03 (m, 2H), 1.15 (t, 6H, J=7.2 Hz)

Example 135

$^1$H NMR (DMSO-$d_6$, 400 MHz) δ 9.98 (br, 1H), 7.63 (s, 1H), 7.52 (s, 1H), 7.28-7.05 (m, 2H), 6.90 (s, 1H), 4.12-3.85 (m, 5H), 3.52-3.45 (m, 2H), 3.11-2.89 (m, 4H), 2.80 (s, 3H), 2.70-2.58 (m, 1H), 2.52-2.38 (m, 2H), 2.19-2.02 (m, 2H), 1.18-1.12 (m, 6H)

Example 136

$^1$H NMR (DMSO-$d_6$, 400 MHz) δ 10.56 (br, 1H), 7.56 (s, 1H), 7.54 (s, 1H), 7.42-7.15 (m, 3H), 6.98 (s, 1H), 4.49 (t, 2H, J=7.9 Hz), 4.19 (t, 2H, J=7.9 Hz), 4.11-3.92 (m, 3H), 3.11-2.85 (m, 4H), 2.71-2.60 (m, 1H), 2.60-2.45 (m, 2H), 2.21-2.01 (m, 2H), 1.20-1.10 (m, 6H)

Example 137

$^1$H NMR (DMSO-$d_6$, 400 MHz) δ 10.16 (br, 1H), 7.70 (s, 1H), 7.44-7.05 (m, 5H), 4.16-4.09 (m, 1H), 4.00 (d, 2H, J=7.7 Hz), 3.51-3.47 (m, 2H), 3.39-3.36 (m, 2H), 3.05-2.91 (m, 4H), 2.69-2.64 (m, 1H), 2.50-2.44 (m, 2H), 2.17-2.05 (m, 2H), 1.92-1.82 (m, 4H), 1.16 (t, 6H, J=7.2 Hz)

Example 138

$^1$H NMR (DMSO-$d_6$, 400 MHz) δ 10.38 (br, 1H), 7.76 (s, 1H), 7.43-7.04 (m, 5H), 6.00-5.98 (m, 1H), 5.89-5.86 (m, 1H), 4.32 (br, 2H), 4.22 (br, 2H), 4.15-4.08 (m, 1H), 4.00 (d, 2H, J=7.7 Hz), 3.07-2.89 (m, 4H), 2.69-2.64 (m, 1H), 2.51-2.43 (m, 2H), 2.15-2.06 (m, 2H), 1.16 (t, 6H, J=7.2 Hz)

Example 139

$^1$H NMR (DMSO-$d_6$, 400 MHz) δ 10.07 (br, 1H), 7.66 (s, 1H), 7.44 (s, 1H), 7.44-7.13 (m, 4H), 4.34-4.30 (m, 2H), 4.13-4.01 (m, 5H), 3.05-2.92 (m, 4H), 2.67-2.63 (m, 1H), 2.50-2.43 (m, 2H), 2.30-2.26 (m, 2H), 2.16-2.08 (m, 2H), 1.16 (t, 6H, J=7.1 Hz)

Example 140

(3R)-3-(2-chloro-6-fluorophenyl)-1-[trans-3-(diethylamino)-cyclobutylmethyl]-4-trifluoromethyl-3-hydroxy-6-(2-oxazolyl)-1,3-dihydro-2H-indol-2-one hydrochloride was obtained similarly using (R)-α-methoxyphenylacetic acid as a resolving agent.

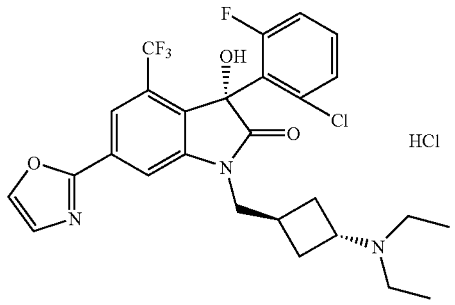

HCl $^1$H NMR (DMSO-$d_6$, 400 MHz) δ 10.09 (br, 1H), 8.34 (s, 1H), 7.97 (s, 1H), 7.81 (s, 1H), 7.48 (s, 1H), 7.42-7.16 (m, 4H), 4.11-4.05 (m, 3H), 3.05-2.90 (m, 4H), 2.71-2.64 (m, 1H), 2.48-2.41 (m, 2H), 2.16-2.09 (m, 2H), 1.12 (t, 6H, J=7.2 Hz).

Optical Rotation

[α]=−100.00

(C=0.106 in $CHCl_3$)

The compound of Example 141 was synthesized in a similar manner to the above.

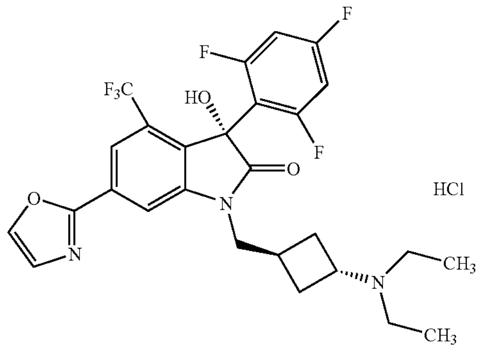

HCl $^1$H NMR (DMSO-$d_6$, 400 MHz) δ 10.38 (br, 1H), 8.36 (s, 1H), 8.03 (s, 1H), 7.85 (s, 1H), 7.50 (d, 1H, J=0.53 Hz), 7.22 (s, 1H), 7.20-7.12 (m, 2H), 4.15-4.00 (m, 3H), 3.15-2.85 (m, 4H), 2.95-2.63 (m, 1H), 2.58-2.43 (m, 2H), 2.18-2.05 (m, 2H), 1.30-1.08 (m, 6H).

Experiment 1

Assessment of Ghrelin Antagonism Using Human GHSR Stably Expressing Cells

By using cells wherein human GHSR (growth hormone secretagogue receptor) is stably expressed, the effects of compounds of the Examples on elevation of cellular calcium ion concentrations were evaluated when endogenous ligand Ghrelin was added to the cells.

Human GHSR stably expressing CHO-K1 cells (EUROSCREEN) were seeded on 96-well assay plate (Black plate, Clear Bottom (Corning)) in $2\times10^4$ cells/100 μl/well, and incubated in cell culture device for 1 day at 37° C. under 5% $CO_2$. The culture medium was Ham's F12 medium containing 10% fetal bovine serum, 100 IU/ml penicillin, 100 μg/ml streptomycin, 400 μg/ml G418 and 250 μg/ml Zeocin.

One hour before the assay, calcium fluorescent indicator was incorporated into the culture medium. Commercially available Calcium Screening Kit (Fluo 3)(Dojindo) was used as the calcium fluorescent indicator. Cells were washed, and then thereto was added Hanks/Hepes (pH7.4) in 200 μl/well.

Ghrelin was combined with an equal amount of the test compound which was prepared with Hanks/Hepes (pH7.4) in a concentration of 10-times of the final concentration, and the mixture was added to the cells in 50 μl/well. Immediately after that, excitation wavelength in 488 nm was measured by FLIPR (Molecular Devices) 80 times at 1 second interval. Ghrelin antagonistic ratio (%) of the compound in the concentration of 1 μM was calculated according to the following equation wherein the values of fluorescence intensity means those obtained by deducting the minimum value from the maximum value.

Ghrelin antagonistic ratio (%)={1−(A−B)/(C−B)}×100

A: Fluorescence intensity in case of adding 1 μM of the compound and 10 nM of Ghrelin B: Fluorescence intensity in case of no addition of the compound and Ghrelin C: Fluorescence intensity in case of adding only 10 nM of Ghrelin Ghrelin antagonistic ratio of the compound of Example 1 was 82%, Ghrelin antagonistic ratio of the compound of Example 14 was 74%, Ghrelin antagonistic ratio of the compound of Example 85 was 96%, and Ghrelin antagonistic ratio of the compound of Example 136 was 96%. It was observed that the present compound antagonized the action of Ghrelin and inhibited elevation of cellular calcium ion.

Experiment 2

Assessment of Feeding in Mice

The effects of compounds of the Examples on the feeding amount in intraperitoneally administering the compound were evaluated using Ghrelin-induced feeding increasing mice.

ICR mice (male, 7-week-old, Charles River Laboratories) were fed in 5 mice in each cage. Food (CE-2, Oriental Yeast Co., Ltd.) and sterile tap water were intaken freely.

ICR mice were intraperitoneally administered the compound (12.5, 25, 50 mg/kg) miscible in 10% polyethylene glycol #400, and immediately after that, intravenously administered Ghrelin (250 nmol/kg) dissolved in saline.

The food weight was measured 4 times in total: just before the administration of Ghrelin, and 1, 2 and 4 hours after the administration. The inhibition ratio was calculated according to the following equation and the integrated feeding amount until each measuring time point. Each treatment group consisted of 10 mice.

Inhibition ratio (%)=(B−C)/(B−A)×100

A: Feeding amount (g) in group administered with only vehicle

B: Feeding amount (g) in group administered with only Ghrelin

C: Feeding amount (g) in group administered with Ghrelin and test compound

Significant antifeeding was observed in the group administered with the compound of Example 1 at the maximum of 110%.

Experiment 3

Assessment of Ghrelin Antagonism in Ghrelin-Induced Feeding Increasing Test

The feeding-increasing and -inhibiting effects of compounds of the Examples on increase of feeding were evaluated in mice where the Ghrelin was intravenously administered.

The lighting cycle in feeding room was set such that the light was turned on during 8:00 to 20:00 and turned off during 20:00 to 8:00, and food and sterile tap water were intaken freely. 7-week-old male ICR mice were intraperitoneally administered the compound dissolved in 10% polyethyleneglycol (PEG) at 9:00. 30 minutes after that, they were intravenously administered Ghrelin in 250 nmol/kg dissolved in saline (raw diet). One hour after the administration of Ghrelin, feed intake was measured.

Feed intake and inhibition ratio one hour after the administration of Ghrelin were shown in Table 1. It was observed that the present compound of Example 49 antagonized the action of Ghrelin and inhibited feeding increasing activity.

TABLE 1

| Group | Feed intake (g) | Inhibition ratio (%) |
|---|---|---|
| PEG + raw diet | 0.09 | 100 |
| PEG + Ghrelin | 0.61 | 0 |
| Compound (3 mg/kg) + Ghrelin | 0.53 | 15 |
| Compound (30 mg/kg) + Ghrelin | 0.30 | 60 |

No statistical processing was carried out.

Experiment 4

Assessment of Antiobesity Activity in Diet-Induced Obese Mice

The antiobesity activities of compounds of the Examples were evaluated using diet-induced obese (DIO) mice.

The lighting cycle in feeding room was set such that the light was turned on during 8:00 to 20:00 and turned off during 20:00 to 8:00, and food and sterile tap water were intaken freely. Four-week-old male C57BL/6 mice were fed fatty food (60 kcal %) for 6 months to produce DIO mice. DIO mice were administered the compound suspended in 0.5% methylcellulose solution (MC) by gavage every day at 9:00 and 17:00. 3 weeks after that, they were vivisected and collected organ and blood.

Cumulative feed intake, inhibition ratio of weight gain, hepatic triglyceride (TG), epididymal fat weight, casual blood glucose levels and total cholesterol (T-chol) values were shown in Table 2. It was observed that the present compound of Example 49 has antiobesity activity.

TABLE 2

| Group | Cumulative feed intake[1] (g) | Inhibition ratio of weight gain (%) | Epididymal fat (g) | Hepatic TG (mg/mg liver) | Casual blood glucose level (mg/dl) | T-chol (mg/dl) |
|---|---|---|---|---|---|---|
| MC | 52.3 | 0.0 | 2.92 | 0.20 | 182 | 216 |
| Compound (3 mg/kg) | 48.9 | 4.6 | 2.74 | 0.21 | 157* | 219 |
| Compound (10 mg/kg) | 52.0 | 2.6 | 2.70 | 0.19 | 148** | 194 |
| Compound (30 mg/kg) | 40.5 | 11.9** | 2.42** | 0.11** | 124** | 154** |

*, **p < 0.05, p < 0.01

[1]No statistical processing was carried out in cumulative feed intake.

INDUSTRIAL APPLICABILITY

The compound of the formula (1) or its prodrug, or a pharmaceutically acceptable salt thereof can be utilized as an effective feeding control agent for treating, preventing or improving diabetes mellitus, obesity, etc.

The invention claimed is:

1. A compound of the formula (1):

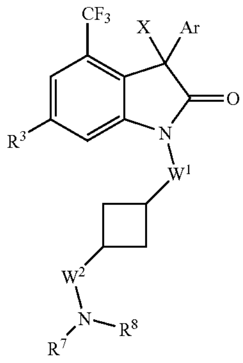

(1)

wherein $R^3$ is hydrogen, optionally substituted alkyl, optionally substituted alkenyl, optionally substituted alkynyl, optionally substituted aryl, optionally substituted heteroaryl, optionally substituted saturated heterocycle, halogen, cyano, nitro, carboxy, hydroxyl, optionally substituted amino, optionally substituted alkoxy, optionally substituted alkanoyl, optionally substituted alkoxycarbonyl, optionally substituted sulfamoyl, optionally substituted carbamoyl, optionally substituted ureido, optionally substituted alkylthio, optionally substituted alkylsulfinyl, optionally substituted alkylsulfonyl, optionally substituted alkylsulfonylamino, optionally substituted arylsulfonylamino, or optionally substituted alkanoylamino;

X is hydrogen, hydroxyl, halogen, $C_1$-$C_4$ alkoxy, or $C_1$-$C_4$ alkanoyloxy optionally substituted by fluorine;

$W^1$ and $W^2$ are each independently a single bond or methylene;

$R^7$ and $R^8$ are each independently hydrogen, optionally substituted alkyl or optionally substituted cycloalkyl, or $R^7$ and $R^8$ are combined together with the adjacent nitrogen atom to form optionally substituted saturated heterocycle;

Ar is optionally substituted aryl or optionally substituted heteroaryl; or a pharmaceutically acceptable salt thereof.

2. The compound of claim 1, wherein Ar is phenyl substituted by 1 or more substituent(s) in which the substituent is selected from alkyl optionally substituted by fluorine, halogen atom or cyano; or a pharmaceutically acceptable salt thereof.

3. The compound of claim 2, wherein Ar is substituted phenyl in which at least one substituent is present at 2-position; or a pharmaceutically acceptable salt thereof.

4. The compound of claim 2, wherein Ar is substituted phenyl in which at least two substituents are present at 2- and 4-positions or 2- and 6-positions; or a pharmaceutically acceptable salt thereof.

5. The compound of claim 2, wherein Ar is substituted phenyl in which at least three substituents are present at 2-, 4- and 6-positions; or a pharmaceutically acceptable salt thereof.

6. The compound of claim 1, wherein $R^3$ is hydrogen, alkyl optionally substituted by halogen, optionally substituted carbamoyl, carboxy, halogen, alkoxy optionally substituted by halogen, optionally substituted heteroaryl, hydroxyl, optionally substituted amino, optionally substituted saturated heterocycle, alkylsulfonyl, sulfamoyl optionally substituted by alkyl, alkanoylamino, alkylsulfonylamino, or $-C \equiv C-(CH_2)_p-Q$ in which p is 1 or 2 and Q is hydroxyl, optionally substituted amino, optionally substituted carbamoyl, optionally substituted saturated heterocycle, alkylsulfonyl, alkanoylamino, alkylsulfonylamino or alkylureido; or a pharmaceutically acceptable salt thereof.

7. The compound of claim 1, wherein $R^3$ is optionally substituted 5-membered heteroaryl, optionally substituted 5-membered saturated heterocycle, optionally substituted carbamoyl or carboxy; or a pharmaceutically acceptable salt thereof.

8. The compound of claim 1, wherein $R^3$ is oxazolyl, substituted oxazolyl, thiazolyl, substituted thiazolyl, triazolyl, imidazolyl, carbamoyl, methylcarbamoyl, dimethylcarbamoyl or carboxy; or a pharmaceutically acceptable salt thereof.

9. The compound of claim 1, wherein $W^1$ and $W^2$ are in trans position in a partial structural formula (Y) of the formula (1):

(Y)

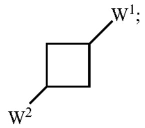

or a pharmaceutically acceptable salt thereof.

10. The compound of claim 9, wherein $W^1$ is methylene and $W^2$ is a single bond; or a pharmaceutically acceptable salt thereof.

11. The compound of claim 1, wherein $R^7$ and $R^8$ are each independently $C_1$-$C_4$ alkyl; or a pharmaceutically acceptable salt thereof.

12. The compound of claim 1, wherein $R^7$ and $R^8$ are each independently cyclopropyl-substituted $C_1$-$C_4$ alkyl; or a pharmaceutically acceptable salt thereof.

13. The compound of claim 1, wherein $R^7$ and $R^8$ are each independently $C_3$-$C_6$ cycloalkyl; or a pharmaceutically acceptable salt thereof.

14. An optically active isomer of the compound of claim 1 in the configuration of the formula (2):

(2)

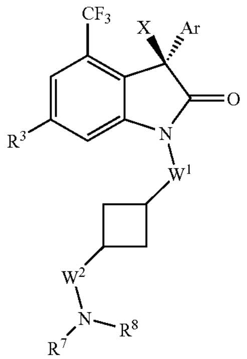

wherein $R^3$, $R^7$, $R^8$, X, Ar, $W^1$ and $W^2$ are the same as defined in claim 1; or a pharmaceutically acceptable salt thereof.

15. A pharmaceutical composition comprising as an active ingredient the compound of claim 1, or a pharmaceutically acceptable salt thereof.

16. A method for treating diabetes, obesity or hyperlipidemia or feed-controlling, comprising administering an effective amount of the compound of claim 1 or a pharmaceutically acceptable salt thereof, to a patient in need of such treatment.

* * * * *